(12) United States Patent
Barnscheid et al.

(10) Patent No.: US 9,872,835 B2
(45) Date of Patent: Jan. 23, 2018

(54) MULTIPARTICLES SAFEGUARDED AGAINST ETHANOLIC DOSE-DUMPING

(71) Applicant: GRÜNENTHAL GMBH, Aachen (DE)

(72) Inventors: Lutz Barnscheid, Mönchengladbach (DE); Klaus Wening, Köln (DE); Jana Pätz, Bornheim (DE); Anja Geissler, Stolberg (DE)

(73) Assignee: GRÜNENTHAL GMBH, Aachen (DE)

( * ) Notice: Subject to any disclaimer, the term of this patent is extended or adjusted under 35 U.S.C. 154(b) by 0 days.

(21) Appl. No.: 14/719,351

(22) Filed: May 22, 2015

(65) Prior Publication Data

US 2015/0335592 A1    Nov. 26, 2015

(30) Foreign Application Priority Data

May 26, 2014  (EP) .................................... 14169801

(51) Int. Cl.
*A61K 31/135*    (2006.01)
*A61K 9/16*    (2006.01)
*A61K 9/48*    (2006.01)
*A61K 31/485*    (2006.01)

(52) U.S. Cl.
CPC .......... *A61K 9/1652* (2013.01); *A61K 9/1623* (2013.01); *A61K 9/1682* (2013.01); *A61K 9/4866* (2013.01); *A61K 31/135* (2013.01); *A61K 31/485* (2013.01)

(58) Field of Classification Search
CPC ... A61K 31/135; A61K 9/1682; A61K 9/4866
See application file for complete search history.

(56) References Cited

U.S. PATENT DOCUMENTS

| | | |
|---|---|---|
| 2,524,855 A | 10/1950 | Schnider et al. |
| 2,806,033 A | 9/1957 | Lewenstein et al. |
| 2,987,445 A | 6/1961 | Levesque |
| 3,332,950 A | 7/1967 | Blumberg et al. |
| 3,370,035 A | 2/1968 | Ogura et al. |
| 3,652,589 A | 3/1972 | Flick et al. |
| 3,806,603 A | 4/1974 | Gaunt et al. |
| 3,865,108 A | 2/1975 | Hartop |
| 3,941,865 A | 3/1976 | Miller et al. |
| 3,966,747 A | 6/1976 | Monkovic et al. |
| 3,980,766 A | 9/1976 | Shaw et al. |
| 4,002,173 A | 1/1977 | Manning et al. |
| 4,014,965 A | 3/1977 | Stube et al. |
| 4,070,494 A | 1/1978 | Hoffmeister et al. |
| 4,070,497 A | 1/1978 | Wismer et al. |
| 4,175,119 A | 11/1979 | Porter |
| 4,200,704 A | 4/1980 | Stanley et al. |
| 4,207,893 A | 6/1980 | Michaels |
| 4,262,017 A | 4/1981 | Kuipers et al. |
| 4,343,789 A | 8/1982 | Kawata et al. |
| 4,353,887 A | 10/1982 | Hess et al. |
| 4,404,183 A | 9/1983 | Kawata et al. |
| 4,427,681 A | 1/1984 | Munshi et al. |
| 4,427,778 A | 1/1984 | Zabriskie |
| 4,457,933 A | 7/1984 | Gordon et al. |
| 4,462,941 A | 7/1984 | Lee et al. |
| 4,473,640 A | 9/1984 | Combie et al. |
| 4,483,847 A | 11/1984 | Augart |
| 4,485,211 A | 11/1984 | Okamoto |
| 4,529,583 A | 7/1985 | Porter |
| 4,599,342 A | 7/1986 | La Hann |
| 4,603,143 A | 7/1986 | Schmidt |
| 4,612,008 A | 9/1986 | Wong et al. |
| 4,629,621 A | 12/1986 | Snipes |
| 4,667,013 A | 5/1987 | Reichle |
| 4,690,822 A | 9/1987 | Uemura |
| 4,713,243 A | 12/1987 | Schiraldi et al. |
| 4,744,976 A | 5/1988 | Snipes et al. |
| 4,764,378 A | 8/1988 | Keitn et al. |
| 4,765,989 A | 8/1988 | Wong et al. |
| 4,774,074 A | 9/1988 | Snipes |
| 4,774,092 A | 9/1988 | Hamilton |

(Continued)

FOREIGN PATENT DOCUMENTS

| AR | 046994 A1 | 12/2004 |
|---|---|---|
| AR | 045353 A1 | 10/2005 |

(Continued)

OTHER PUBLICATIONS

Chibuzor et al. (Hindawi Publ. Corporation ISRN Pharmaceutics, vol. 2013, Article ID 838403, 8 pages.*
Sathish et al. (International J. of Pharmaceutical sciences; 5(4) (2013).*
Verhoeven et al (European Journal of Pharmaceutics and Biopharmaceutics, 63(3) 320-330; (2006).*
2.9 Methoden der pharmazeutischen Technologie, European Pharmacopeia, 143-144, 1997, (Full English translation attached).
Albertini, B. "New spray congealing atomizer for the microencapsulation of highly concentrated solid and liquid substances" European Journal of Pharmaceutics and Biopharmaceutics 69 (2008) 348-357.
Almeida, A. et al., Ethylene vinyl acetate as matrix for oral sustained release dosage forms produced via hot-melt extrusion, European Journal of Pharmaceutics and Biopharmaceutics 77 (2011) 297-305.
Almeida, A. et al., Sustained release from hot-melt extruded matrices based on ethylene vinyl acetate and polyethylene oxide, European Journal of Pharmaceutics and Biopharmaceutics 82 (2012) 526-533.

(Continued)

Primary Examiner — Shirley V Gembeh
(74) Attorney, Agent, or Firm — Norris McLaughlin & Marcus, P.A.

(57) ABSTRACT

The invention relates to an oral pharmaceutical dosage form providing resistance against dose dumping in aqueous ethanol and comprising a pharmacologically active ingredient embedded in a matrix material,
 wherein the matrix material comprises an alkyl cellulose and a heteropolysaccharide; and
 wherein the relative weight ratio of heteropolysaccharide to alkyl cellulose is within the range of from 1:20 to 20:1; and
wherein the total content of alkyl cellulose and heteropolysaccharide is at least 35 wt.-%, relative to the total weight of the dosage form. A process of producing the dosage form and methods of using the dosage form, for example to treat pain, are also disclosed.

16 Claims, 5 Drawing Sheets

(56) References Cited

U.S. PATENT DOCUMENTS

| | | |
|---|---|---|
| 4,783,337 A | 11/1988 | Wong et al. |
| 4,806,337 A | 2/1989 | Snipes et al. |
| RE33,093 E | 10/1989 | Schiraldi et al. |
| 4,880,585 A | 11/1989 | Klimesch et al. |
| 4,892,778 A | 1/1990 | Theeuwes et al. |
| 4,892,889 A | 1/1990 | Kirk |
| 4,940,556 A | 7/1990 | MacFarlane et al. |
| 4,954,346 A | 9/1990 | Sparta et al. |
| 4,957,668 A | 9/1990 | Plackard et al. |
| 4,957,681 A | 9/1990 | Klimesch et al. |
| 4,960,814 A | 10/1990 | Wu et al. |
| 4,992,278 A | 2/1991 | Khanna |
| 4,992,279 A | 2/1991 | Palmer et al. |
| 5,004,601 A | 4/1991 | Snipes |
| 5,051,261 A | 9/1991 | McGinty |
| 5,073,379 A | 12/1991 | Klimesch et al. |
| 5,082,668 A | 1/1992 | Wong et al. |
| 5,126,151 A | 6/1992 | Bodor et al. |
| 5,139,790 A | 8/1992 | Snipes |
| 5,145,944 A | 9/1992 | Steinmann |
| 5,149,538 A | 9/1992 | Granger et al. |
| 5,169,645 A | 12/1992 | Shukla et al. |
| 5,190,760 A | 3/1993 | Baker |
| 5,198,226 A | 3/1993 | MacFarlane et al. |
| 5,200,197 A | 4/1993 | Wright et al. |
| 5,211,892 A | 5/1993 | Gueret |
| 5,225,417 A | 7/1993 | Dappen |
| 5,227,157 A | 7/1993 | Mc Ginity et al. |
| 5,229,164 A | 7/1993 | Pins et al. |
| 5,273,758 A | 12/1993 | Royce |
| 5,326,852 A | 7/1994 | Fujikake |
| 5,350,741 A | 9/1994 | Takada |
| 5,378,462 A | 1/1995 | Boedecker et al. |
| 5,387,420 A | 2/1995 | Mitchell |
| 5,427,798 A | 6/1995 | Ludwig et al. |
| RE34,990 E | 7/1995 | Khanna et al. |
| 5,458,887 A | 10/1995 | Chen |
| 5,460,826 A | 10/1995 | Merrill et al. |
| 5,472,943 A | 12/1995 | Crain et al. |
| 5,508,042 A | 4/1996 | Oshlack et al. |
| 5,552,159 A | 9/1996 | Mueller et al. |
| 5,556,640 A | 9/1996 | Ito et al. |
| 5,562,920 A | 10/1996 | Demmer et al. |
| 5,591,452 A | 1/1997 | Miller et al. |
| 5,593,694 A | 1/1997 | Hayashida et al. |
| 5,601,842 A | 2/1997 | Bartholomaeus |
| 5,620,697 A | 4/1997 | Tormala et al. |
| 5,679,685 A | 10/1997 | Cincotta et al. |
| 5,681,517 A | 10/1997 | Metzger |
| 5,707,636 A | 1/1998 | Rodriguez et al. |
| 5,741,519 A | 4/1998 | Rosenberg et al. |
| 5,792,474 A | 8/1998 | Rauchfuss |
| 5,801,201 A | 9/1998 | Gradums et al. |
| 5,811,126 A | 9/1998 | Krishnamurthy |
| 5,849,240 A | 12/1998 | Miller et al. |
| 5,866,164 A | 2/1999 | Kuczynski et al. |
| 5,900,425 A | 5/1999 | Kanikanti et al. |
| 5,908,850 A | 6/1999 | Zeitlin et al. |
| 5,916,584 A | 6/1999 | O'Donoghue et al. |
| 5,928,739 A | 7/1999 | Pophusen et al. |
| 5,939,099 A | 8/1999 | Grabowski et al. |
| 5,945,125 A | 8/1999 | Kim |
| 5,948,787 A | 9/1999 | Merrill et al. |
| 5,962,488 A | 10/1999 | Lang |
| 5,965,161 A | 10/1999 | Oshlack et al. |
| 5,968,925 A | 10/1999 | Knidlberger |
| 6,001,391 A | 12/1999 | Zeidler et al. |
| 6,009,390 A | 12/1999 | Gupta et al. |
| 6,009,690 A | 1/2000 | Rosenberg et al. |
| 6,051,253 A | 4/2000 | Zettler et al. |
| 6,071,970 A | 6/2000 | Mueller et al. |
| 6,077,538 A | 6/2000 | Merrill et al. |
| 6,090,411 A | 7/2000 | Pillay et al. |
| 6,093,420 A * | 7/2000 | Baichwal .............. A61K 9/205 424/464 |
| 6,096,339 A | 8/2000 | Ayer et al. |
| 6,117,453 A | 9/2000 | Seth et al. |
| 6,120,802 A | 9/2000 | Breitenbach et al. |
| 6,133,241 A | 10/2000 | Bok et al. |
| 6,183,781 B1 | 2/2001 | Burke |
| 6,228,863 B1 | 5/2001 | Palermo et al. |
| 6,235,825 B1 | 5/2001 | Yoshida et al. |
| 6,238,697 B1 | 5/2001 | Kumar et al. |
| 6,245,357 B1 | 6/2001 | Edgren et al. |
| 6,248,737 B1 | 6/2001 | Buschmann et al. |
| 6,254,887 B1 | 7/2001 | Miller et al. |
| 6,261,599 B1 | 7/2001 | Oshlack |
| 6,290,990 B1 | 9/2001 | Grabowski et al. |
| 6,306,438 B1 | 10/2001 | Oshlack et al. |
| 6,309,668 B1 | 10/2001 | Bastin et al. |
| 6,318,650 B1 | 11/2001 | Breitenbach et al. |
| 6,322,819 B1 | 11/2001 | Burnside et al. |
| 6,326,027 B1 | 12/2001 | Miller et al. |
| 6,335,035 B1 | 1/2002 | Drizen et al. |
| 6,337,319 B1 | 1/2002 | Wang |
| 6,340,475 B2 | 1/2002 | Shell et al. |
| 6,344,215 B1 | 2/2002 | Bettman et al. |
| 6,344,535 B1 | 2/2002 | Timmermann et al. |
| 6,348,469 B1 | 2/2002 | Seth |
| 6,355,656 B1 | 3/2002 | Zeitlin et al. |
| 6,375,957 B1 | 4/2002 | Kaiko et al. |
| 6,375,963 B1 | 4/2002 | Repka et al. |
| 6,387,995 B1 | 5/2002 | Sojka |
| 6,399,100 B1 | 6/2002 | Clancy et al. |
| 6,419,954 B1 | 7/2002 | Chu et al. |
| 6,436,441 B1 | 8/2002 | Sako et al. |
| 6,461,644 B1 | 10/2002 | Jackson et al. |
| 6,488,939 B1 | 12/2002 | Zeidler et al. |
| 6,488,962 B1 | 12/2002 | Berner et al. |
| 6,488,963 B1 | 12/2002 | McGinity et al. |
| 6,534,089 B1 | 3/2003 | Ayer et al. |
| 6,547,977 B1 | 4/2003 | Yan et al. |
| 6,547,997 B1 | 4/2003 | Breithenbach et al. |
| 6,562,375 B1 | 5/2003 | Sako et al. |
| 6,569,506 B1 | 5/2003 | Jerdee et al. |
| 6,572,889 B1 | 6/2003 | Guo |
| 6,592,901 B2 | 7/2003 | Durig et al. |
| 6,623,754 B2 | 9/2003 | Guo et al. |
| 6,635,280 B2 | 10/2003 | Shell et al. |
| 6,696,088 B2 | 2/2004 | Oshlack et al. |
| 6,699,503 B1 | 3/2004 | Sako et al. |
| 6,723,340 B2 | 4/2004 | Gusler et al. |
| 6,723,343 B2 | 4/2004 | Kugelmann |
| 6,733,783 B2 | 5/2004 | Oshlack et al. |
| 6,753,009 B2 | 6/2004 | Luber et al. |
| 6,821,588 B1 | 11/2004 | Hammer et al. |
| 6,979,722 B2 | 12/2005 | Hamamoto et al. |
| 7,074,430 B2 | 7/2006 | Miller et al. |
| 7,129,248 B2 | 10/2006 | Chapman et al. |
| 7,141,250 B2 | 11/2006 | Oshlack et al. |
| 7,157,103 B2 | 1/2007 | Sackler |
| 7,176,251 B1 | 2/2007 | Bastioli et al. |
| RE39,593 E | 4/2007 | Buschmann et al. |
| 7,201,920 B2 | 4/2007 | Kumar et al. |
| 7,214,385 B2 | 5/2007 | Gruber |
| 7,230,005 B2 | 6/2007 | Shafer et al. |
| 7,300,668 B2 | 11/2007 | Pryce et al. |
| 7,332,182 B2 | 2/2008 | Sackler |
| 7,388,068 B2 | 6/2008 | Falk et al. |
| 7,399,488 B2 | 7/2008 | Hirsh et al. |
| 7,510,726 B2 | 3/2009 | Kumar et al. |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,776,314 B2 | 8/2010 | Bartholomaus et al. |
| 7,842,307 B2 | 11/2010 | Oshlack et al. |
| 7,851,482 B2 | 12/2010 | Dung et al. |
| 7,939,543 B2 | 5/2011 | Kupper |
| 7,968,119 B2 | 6/2011 | Farrell |
| 7,994,364 B2 | 8/2011 | Fischer et al. |
| 8,075,872 B2 | 12/2011 | Arkenau-Maric |
| 8,101,630 B2 | 1/2012 | Kumar et al. |
| 8,114,383 B2 | 2/2012 | Bartholomaeus et al. |
| 8,114,384 B2 | 2/2012 | Arkenau et al. |

(56) References Cited

U.S. PATENT DOCUMENTS

| | | |
|---|---|---|
| 8,114,838 B2 | 2/2012 | Marchionni |
| 8,192,722 B2 | 6/2012 | Arkenau-Maric et al. |
| 8,202,542 B1 | 6/2012 | Mehta et al. |
| 8,309,060 B2 | 11/2012 | Bartholomeus et al. |
| 8,309,122 B2 | 11/2012 | Kao et al. |
| 8,323,889 B2 | 12/2012 | Arkenau-Maric et al. |
| 8,329,216 B2 | 12/2012 | Kao et al. |
| 8,337,888 B2 | 12/2012 | Wright et al. |
| 8,383,152 B2 | 2/2013 | Jans et al. |
| 8,420,056 B2 | 4/2013 | Arkenau-Maric et al. |
| 8,445,023 B2 | 5/2013 | Guimberteau et al. |
| 8,722,086 B2 | 5/2014 | Arkenau-Maric et al. |
| 8,858,963 B1 | 10/2014 | Devarakonda et al. |
| 9,192,578 B2 | 11/2015 | McGinity et al. |
| 2001/0038852 A1 | 11/2001 | Kolter et al. |
| 2002/0012701 A1 | 1/2002 | Kolter et al. |
| 2002/0015730 A1 | 2/2002 | Hoffmann et al. |
| 2002/0187192 A1 | 2/2002 | Joshi et al. |
| 2002/0051820 A1 | 5/2002 | Shell et al. |
| 2002/0114838 A1 | 8/2002 | Ayer et al. |
| 2002/0132359 A1 | 9/2002 | Waterman |
| 2002/0132395 A1 | 9/2002 | Iyer et al. |
| 2002/0176888 A1 | 11/2002 | Bartholomaeus et al. |
| 2002/0192277 A1 | 12/2002 | Oshlack et al. |
| 2003/0008409 A1 | 1/2003 | Spearman et al. |
| 2003/0015814 A1 | 1/2003 | Krull et al. |
| 2003/0017532 A1 | 1/2003 | Biswas et al. |
| 2003/0021546 A1 | 1/2003 | Sato |
| 2003/0044458 A1 | 3/2003 | Wright et al. |
| 2003/0044464 A1 | 3/2003 | Ziegler et al. |
| 2003/0064099 A1 | 4/2003 | Oshlack et al. |
| 2003/0068276 A1 | 4/2003 | Hughes et al. |
| 2003/0068370 A1 | 4/2003 | Sackler et al. |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0069263 A1 | 4/2003 | Breder et al. |
| 2003/0077297 A1 | 4/2003 | Chen et al. |
| 2003/0091630 A1 | 5/2003 | Louie-Helm et al. |
| 2003/0092724 A1 | 5/2003 | Huaihung et al. |
| 2003/0104052 A1 | 6/2003 | Berner et al. |
| 2003/0104053 A1 | 6/2003 | Gusler et al. |
| 2003/0118641 A1 | 6/2003 | Maloney et al. |
| 2003/0124185 A1 | 7/2003 | Oshlack et al. |
| 2003/0125347 A1 | 7/2003 | Anderson et al. |
| 2003/0129230 A1 | 7/2003 | Baichwal et al. |
| 2003/0133985 A1 | 7/2003 | Louie-Helm et al. |
| 2003/0143269 A1 | 7/2003 | Oshlack et al. |
| 2003/0152622 A1 | 8/2003 | Louie-Helm et al. |
| 2003/0158242 A1 | 8/2003 | Kugelmann |
| 2003/0175326 A1 | 9/2003 | Thombre |
| 2003/0198677 A1 | 10/2003 | Pryce Lewis et al. |
| 2003/0215508 A1 | 11/2003 | Davis et al. |
| 2003/0232895 A1 | 12/2003 | Omidian et al. |
| 2004/0010000 A1 | 1/2004 | Ayer et al. |
| 2004/0011806 A1 | 1/2004 | Luciano et al. |
| 2004/0052731 A1 | 3/2004 | Hirsh et al. |
| 2004/0052844 A1 | 3/2004 | Hsiao et al. |
| 2004/0081694 A1 | 4/2004 | Oshlack |
| 2004/0091528 A1 | 5/2004 | Rogers et al. |
| 2004/0126428 A1 | 7/2004 | Hughes et al. |
| 2004/0131671 A1 | 7/2004 | Zhang et al. |
| 2004/0156899 A1 | 8/2004 | Louie-Helm et al. |
| 2004/0170567 A1 | 9/2004 | Sackler |
| 2004/0170680 A1 | 9/2004 | Oshlack et al. |
| 2004/0185105 A1 | 9/2004 | Berner et al. |
| 2004/0213845 A1 | 10/2004 | Sugihara |
| 2004/0213848 A1 | 10/2004 | Li et al. |
| 2005/0015730 A1 | 1/2005 | Gunturi et al. |
| 2005/0031546 A1 | 2/2005 | Bartholomaeus et al. |
| 2005/0058706 A1 | 3/2005 | Bartholomaeus et al. |
| 2005/0063214 A1 | 3/2005 | Takashima |
| 2005/0089475 A1 | 4/2005 | Gruber |
| 2005/0089569 A1 | 4/2005 | Bar-Shalom |
| 2005/0095291 A1 | 5/2005 | Oshlack et al. |
| 2005/0106249 A1 | 5/2005 | Hwang et al. |
| 2005/0112067 A1 | 5/2005 | Kumar et al. |
| 2005/0127555 A1 | 6/2005 | Gusik et al. |
| 2005/0152843 A1 | 7/2005 | Bartholomaeus et al. |
| 2005/0181046 A1 | 8/2005 | Oshlack et al. |
| 2005/0186139 A1 | 8/2005 | Bartholomaus et al. |
| 2005/0191244 A1 | 9/2005 | Bartholomaeus et al. |
| 2005/0191352 A1 | 9/2005 | Hayes |
| 2005/0192333 A1 | 9/2005 | Hinze et al. |
| 2005/0214223 A1 | 9/2005 | Bartholomaeus et al. |
| 2005/0220877 A1 | 10/2005 | Patel |
| 2005/0222188 A1 | 10/2005 | Chapman et al. |
| 2005/0236741 A1 | 10/2005 | Arkenau et al. |
| 2005/0245556 A1 | 11/2005 | Brogman et al. |
| 2005/0266084 A1 | 12/2005 | Li et al. |
| 2006/0002859 A1 | 1/2006 | Arkenau et al. |
| 2006/0002860 A1 | 1/2006 | Bartholomaus et al. |
| 2006/0004034 A1 | 1/2006 | Hinze et al. |
| 2006/0009478 A1 | 1/2006 | Friedman et al. |
| 2006/0012701 A1 | 1/2006 | Sung-Bin |
| 2006/0017916 A1 | 1/2006 | Clarke et al. |
| 2006/0039864 A1 | 2/2006 | Bartholomaus et al. |
| 2006/0073102 A1 | 4/2006 | Huaihung et al. |
| 2006/0099250 A1 | 5/2006 | Tian et al. |
| 2006/0104909 A1 | 5/2006 | Vaghefi |
| 2006/0182801 A1 | 8/2006 | Breder et al. |
| 2006/0188447 A1 | 8/2006 | Arkenau-Maric et al. |
| 2006/0193782 A1 | 8/2006 | Bartholomaus et al. |
| 2006/0193914 A1 | 8/2006 | Ashworth et al. |
| 2006/0194759 A1 | 8/2006 | Edelson |
| 2006/0194826 A1 | 8/2006 | Oshlack et al. |
| 2006/0240105 A1 | 10/2006 | Devane et al. |
| 2006/0240110 A1 | 10/2006 | Kiick et al. |
| 2006/0269603 A1 | 11/2006 | Brown Miller et al. |
| 2007/0003616 A1 | 1/2007 | Arkenau-Maric et al. |
| 2007/0003617 A1 | 1/2007 | Fischer et al. |
| 2007/0020188 A1 | 1/2007 | Sackler |
| 2007/0020335 A1 | 1/2007 | Chen et al. |
| 2007/0042044 A1 | 2/2007 | Fischer et al. |
| 2007/0048228 A1 | 3/2007 | Arkenau-Maric et al. |
| 2007/0065365 A1 | 3/2007 | Kugelmann et al. |
| 2007/0092573 A1 | 4/2007 | Joshi et al. |
| 2007/0183979 A1 | 8/2007 | Arkenau-Maric et al. |
| 2007/0183980 A1 | 8/2007 | Arkenau-Maric et al. |
| 2007/0184117 A1 | 8/2007 | Gregory et al. |
| 2007/0190142 A1 | 8/2007 | Breitenbach et al. |
| 2007/0196396 A1 | 8/2007 | Pilgaonkar et al. |
| 2007/0196481 A1 | 8/2007 | Amidon et al. |
| 2007/0224129 A1 | 9/2007 | Guimberteau et al. |
| 2007/0231268 A1 | 10/2007 | Emigh et al. |
| 2007/0259045 A1 | 11/2007 | Mannion et al. |
| 2007/0264327 A1 | 11/2007 | Kumar et al. |
| 2007/0269505 A1 | 11/2007 | Flath et al. |
| 2007/0292508 A1 | 12/2007 | Szamosi et al. |
| 2008/0020032 A1 | 1/2008 | Crowley et al. |
| 2008/0063725 A1 | 3/2008 | Guimberteau et al. |
| 2008/0069871 A1 | 3/2008 | Vaughn et al. |
| 2008/0075669 A1 | 3/2008 | Soscia et al. |
| 2008/0075768 A1* | 3/2008 | Vaughn ............... A61K 9/2013 424/456 |
| 2008/0081290 A1 | 3/2008 | Wada et al. |
| 2008/0085304 A1 | 4/2008 | Baichwal et al. |
| 2008/0131503 A1 | 6/2008 | Holm et al. |
| 2008/0145429 A1 | 6/2008 | Leyenecker et al. |
| 2008/0152595 A1 | 6/2008 | Emigh et al. |
| 2008/0181932 A1 | 7/2008 | Bortz et al. |
| 2008/0220079 A1 | 9/2008 | Chen |
| 2008/0233178 A1 | 9/2008 | Reidenberg et al. |
| 2008/0234352 A1 | 9/2008 | Fischer et al. |
| 2008/0247959 A1 | 10/2008 | Bartholomaus et al. |
| 2008/0248113 A1 | 10/2008 | Bartholomaus et al. |
| 2008/0280975 A1 | 11/2008 | Badul et al. |
| 2008/0311049 A1 | 12/2008 | Arkenau-Maric et al. |
| 2008/0311187 A1 | 12/2008 | Ashworth et al. |
| 2008/0311197 A1 | 12/2008 | Arkenau-Maric et al. |
| 2008/0311205 A1 | 12/2008 | Habib et al. |
| 2008/0312264 A1 | 12/2008 | Arkenau-Maric et al. |
| 2008/0317695 A1 | 12/2008 | Everaert et al. |
| 2008/0317854 A1 | 12/2008 | Arkenau et al. |

(56) References Cited

U.S. PATENT DOCUMENTS

| | | |
|---|---|---|
| 2009/0004267 A1 | 1/2009 | Arkenau-Maric et al. |
| 2009/0005408 A1 | 1/2009 | Arkenau-Maric et al. |
| 2009/0011016 A1 | 1/2009 | Cailly-Dufestel et al. |
| 2009/0017121 A1 | 1/2009 | Berner et al. |
| 2009/0022798 A1 | 1/2009 | Rosenberg et al. |
| 2009/0081287 A1 | 3/2009 | Wright et al. |
| 2009/0081290 A1 | 3/2009 | McKenna et al. |
| 2009/0117191 A1 | 5/2009 | Brown Miller et al. |
| 2009/0202634 A1 | 8/2009 | Jans et al. |
| 2009/0215808 A1 | 8/2009 | Yum et al. |
| 2009/0232887 A1 | 9/2009 | Odidi et al. |
| 2009/0253730 A1 | 10/2009 | Kumar et al. |
| 2009/0317355 A1 | 12/2009 | Roth et al. |
| 2009/0318395 A1 | 12/2009 | Schramm et al. |
| 2010/0015223 A1 | 1/2010 | Cailly-Deufestel et al. |
| 2010/0035886 A1 | 2/2010 | Cincotta et al. |
| 2010/0047345 A1 | 2/2010 | Crowley et al. |
| 2010/0092553 A1 | 4/2010 | Guimberteau et al. |
| 2010/0098758 A1 | 4/2010 | Bartholomaus et al. |
| 2010/0099696 A1 | 4/2010 | Soscia et al. |
| 2010/0104638 A1 | 4/2010 | Dai et al. |
| 2010/0151028 A1 | 6/2010 | Ashworth et al. |
| 2010/0168148 A1 | 7/2010 | Wright et al. |
| 2010/0172989 A1 | 7/2010 | Roth et al. |
| 2010/0203129 A1 | 8/2010 | Anderson et al. |
| 2010/0221322 A1 | 9/2010 | Bartholomaus et al. |
| 2010/0249045 A1 | 9/2010 | Babul |
| 2010/0260833 A1 | 10/2010 | Bartholomaus et al. |
| 2010/0280047 A1 | 11/2010 | Kolter et al. |
| 2010/0291205 A1 | 11/2010 | Downie et al. |
| 2010/0297229 A1 | 11/2010 | Sesha |
| 2011/0020451 A1 | 1/2011 | Bartholomaus et al. |
| 2011/0020454 A1 | 1/2011 | Lamarca Casado |
| 2011/0038930 A1 | 2/2011 | Barnscheid et al. |
| 2011/0082214 A1 | 4/2011 | Faure et al. |
| 2011/0092515 A1 | 4/2011 | Qiu et al. |
| 2011/0097404 A1 | 4/2011 | Oshlack et al. |
| 2011/0129535 A1 | 6/2011 | Mantelle |
| 2011/0159100 A1 | 6/2011 | Anderson et al. |
| 2011/0187017 A1 | 8/2011 | Haupts |
| 2011/0245783 A1 | 10/2011 | Stinchcomb |
| 2011/0262496 A1 | 10/2011 | Desai |
| 2012/0034171 A1 | 2/2012 | Arkenau-Maric et al. |
| 2012/0059065 A1 | 3/2012 | Barnscheid et al. |
| 2012/0065220 A1 | 3/2012 | Barnscheid et al. |
| 2012/0077879 A1 | 3/2012 | Vasanthavada et al. |
| 2012/0107250 A1 | 5/2012 | Bartholomaus et al. |
| 2012/0108622 A1 | 5/2012 | Wright et al. |
| 2012/0135071 A1 | 5/2012 | Bartholomaus et al. |
| 2012/0136021 A1 | 5/2012 | Barnscheid et al. |
| 2012/0141583 A1 | 6/2012 | Mannion et al. |
| 2012/0202838 A1 | 8/2012 | Ghosh et al. |
| 2012/0225901 A1 | 9/2012 | Leyendecker et al. |
| 2012/0231083 A1 | 9/2012 | Carley et al. |
| 2012/0251637 A1 | 10/2012 | Bartholomaus et al. |
| 2012/0321716 A1 | 12/2012 | Vachon et al. |
| 2013/0028970 A1 | 1/2013 | Schwier et al. |
| 2013/0090349 A1 | 4/2013 | Gei Ler et al. |
| 2013/0129825 A1 | 5/2013 | Billoet et al. |
| 2013/0129826 A1 | 5/2013 | Gei Ler et al. |
| 2013/0171075 A1 | 7/2013 | Arkenau-Maric et al. |
| 2013/0209557 A1 | 8/2013 | Barnscheid |
| 2013/0225625 A1 | 8/2013 | Barnscheid et al. |
| 2013/0251643 A1 | 9/2013 | Bartholomäus et al. |
| 2013/0289062 A1 | 10/2013 | Kumar et al. |
| 2013/0303623 A1 | 11/2013 | Barnscheid et al. |
| 2013/0330409 A1 | 12/2013 | Mohammad |
| 2014/0010874 A1 | 1/2014 | Sackler |
| 2014/0079780 A1 | 3/2014 | Arkenau Maric et al. |
| 2014/0080858 A1 | 3/2014 | Bartholomäus et al. |
| 2014/0080915 A1 | 3/2014 | Bartholomäus et al. |
| 2014/0094481 A1 | 4/2014 | Fleischer et al. |
| 2014/0112984 A1 | 4/2014 | Arkenau Maric et al. |
| 2014/0112989 A1 | 4/2014 | Bartholomäus et al. |
| 2014/0170079 A1 | 6/2014 | Arkenau Maric et al. |
| 2014/0186440 A1 | 7/2014 | Han et al. |
| 2014/0356426 A1 | 12/2014 | Barnscheid et al. |
| 2014/0356428 A1 | 12/2014 | Barnscheid et al. |
| 2014/0378498 A1 | 12/2014 | Devarakonda et al. |
| 2015/0017250 A1 | 1/2015 | Wenig et al. |
| 2015/0030677 A1 | 1/2015 | Adjei et al. |
| 2015/0064250 A1 | 3/2015 | Ghebre-Sellassie et al. |
| 2015/0079150 A1 | 3/2015 | Fischer et al. |
| 2015/0118300 A1 | 4/2015 | Haswani et al. |
| 2015/0118302 A1 | 4/2015 | Haswani et al. |
| 2015/0118303 A1 | 4/2015 | Haswani et al. |
| 2015/0374630 A1 | 12/2015 | Arkenau Maric et al. |
| 2016/0184297 A1 | 6/2016 | Arkenau-Maric et al. |
| 2016/0256456 A1 | 9/2016 | Caruso et al. |
| 2016/0263037 A1 | 9/2016 | Arkenau-Maric et al. |
| 2016/0361308 A1 | 12/2016 | Bartholomaeus et al. |
| 2016/0367549 A1 | 12/2016 | Bartholomaeus et al. |
| 2017/0027886 A1 | 2/2017 | Bartholomaus et al. |

FOREIGN PATENT DOCUMENTS

| | | |
|---|---|---|
| AR | 049562 A1 | 8/2006 |
| AR | 053304 A1 | 5/2007 |
| AR | 054222 A1 | 6/2007 |
| AR | 054328 A1 | 6/2007 |
| AU | 769807 B2 | 3/2001 |
| AU | 2003237944 A1 | 12/2003 |
| AU | 2003274071 A1 | 5/2004 |
| AU | 2003278133 A1 | 5/2004 |
| AU | 2003279317 A1 | 5/2004 |
| AU | 2004264666 B2 | 2/2005 |
| AU | 2004264667 A1 | 2/2005 |
| AU | 2004308653 B2 | 4/2005 |
| AU | 2005259476 B2 | 1/2006 |
| AU | 2005259478 B2 | 1/2006 |
| AU | 2006210145 32 | 8/2006 |
| AU | 2006210145 A1 | 8/2006 |
| AU | 2009207796 A1 | 7/2009 |
| AU | 2009243681 A1 | 11/2009 |
| AU | 2006311116 B2 | 1/2013 |
| BR | P10413318 A | 10/2006 |
| BR | P10413361 A | 10/2006 |
| BR | P10513300 A | 5/2008 |
| BR | P10606145 A2 | 2/2009 |
| CA | 0722109 A | 11/1965 |
| CA | 2082573 C | 5/1993 |
| CA | 2577233 A1 | 10/1997 |
| CA | 2650637 A1 | 10/1997 |
| CA | 229621 A1 | 3/1998 |
| CA | 2317747 A1 | 7/1999 |
| CA | 2343234 A1 | 3/2000 |
| CA | 2352874 A1 | 6/2000 |
| CA | 2414349 A1 | 1/2002 |
| CA | 2456322 A1 | 2/2003 |
| CA | 2502965 A1 | 5/2004 |
| CA | 2503155 A1 | 5/2004 |
| CA | 2534925 A1 | 2/2005 |
| CA | 2534932 A1 | 2/2005 |
| CA | 2489855 A1 | 4/2005 |
| CA | 2551231 A1 | 7/2005 |
| CA | 2572352 A1 | 1/2006 |
| CA | 2572491 A1 | 1/2006 |
| CA | 2595954 A1 | 7/2006 |
| CA | 2229650 C | 8/2006 |
| CA | 2594713 A1 | 8/2006 |
| CA | 2595979 A1 | 8/2006 |
| CA | 2625055 A1 | 4/2007 |
| CA | 2713128 A1 | 7/2009 |
| CA | 2723438 A1 | 11/2009 |
| CA | 2595954 C | 1/2011 |
| CH | 689109 A5 | 10/1998 |
| CL | 20162004 | 5/2005 |
| CL | 20172004 A1 | 5/2005 |
| CL | 200403308 A1 | 9/2005 |
| CL | 200500952 | 11/2005 |
| CL | 200501624 | 12/2005 |
| CL | 200501625 | 6/2006 |
| CL | 424-2013 | 3/2012 |
| CL | 437-2013 | 3/2012 |

(56) References Cited

FOREIGN PATENT DOCUMENTS

| | | |
|---|---|---|
| CN | 87102755 A | 10/1987 |
| CN | 1135175 A | 11/1996 |
| CN | 1473562 A | 2/2004 |
| CN | 1980643 A | 4/2005 |
| CN | 101010071 A | 6/2005 |
| CN | 1671475 A | 9/2005 |
| CN | 1863513 A | 11/2006 |
| CN | 1863514 A | 11/2006 |
| CN | 101022787 A | 12/2006 |
| CN | 1917862 A | 2/2007 |
| CN | 1942174 A | 4/2007 |
| CN | 101011395 A | 8/2007 |
| CN | 101027044 A | 8/2007 |
| CN | 101057849 A | 10/2007 |
| CN | 101484135 A | 11/2007 |
| CN | 101091721 | 12/2007 |
| CN | 101111232 A | 1/2008 |
| CN | 101175482 A | 2/2008 |
| CN | 101370485 A | 2/2009 |
| CN | 101394839 A | 3/2009 |
| CN | 101652128 A | 2/2010 |
| DE | 2530563 A1 | 1/1977 |
| DE | 4229085 A1 | 3/1994 |
| DE | 4309528 A1 | 9/1994 |
| DE | 4446470 A1 | 8/1996 |
| DE | 69400215 T2 | 10/1996 |
| DE | 19522899 C1 | 12/1996 |
| DE | 2808505 A1 | 1/1997 |
| DE | 19753534 A1 | 6/1999 |
| DE | 19800689 C1 | 7/1999 |
| DE | 19800698 A1 | 7/1999 |
| DE | 19822979 A1 | 12/1999 |
| DE | 69229881 T2 | 12/1999 |
| DE | 19855440 A1 | 6/2000 |
| DE | 19856147 A1 | 6/2000 |
| DE | 19940740 A1 | 3/2001 |
| DE | 19960494 A1 | 6/2001 |
| DE | 10036400 A1 | 6/2002 |
| DE | 69429710 T2 | 8/2002 |
| DE | 10250083 A1 | 12/2003 |
| DE | 10250084 A1 | 5/2004 |
| DE | 10250087 A1 | 5/2004 |
| DE | 10250088 A1 | 5/2004 |
| DE | 10336400 A1 | 3/2005 |
| DE | 10361596 A1 | 9/2005 |
| DE | 102004019916 A1 | 11/2005 |
| DE | 102004020220 A1 | 11/2005 |
| DE | 102004032049 A1 | 1/2006 |
| DE | 102004032051 A1 | 1/2006 |
| DE | 102004032103 A1 | 1/2006 |
| DE | 102005005446 A1 | 8/2006 |
| DE | 102005005449 A1 | 8/2006 |
| DE | 102007011485 A1 | 9/2008 |
| DK | 1658055 T3 | 7/2007 |
| DK | 1658054 T3 | 10/2007 |
| DK | 1515702 T3 | 1/2009 |
| EC | SP066345 A | 8/2006 |
| EP | 0008131 A1 | 2/1980 |
| EP | 0043254 A1 | 1/1982 |
| EP | 0008131 B1 | 12/1982 |
| EP | 0177893 A2 | 4/1986 |
| EP | 0216453 A2 | 4/1987 |
| EP | 0226061 A2 | 6/1987 |
| EP | 0228417 A1 | 7/1987 |
| EP | 0229652 A2 | 7/1987 |
| EP | 0232877 A2 | 8/1987 |
| EP | 0239973 A2 | 10/1987 |
| EP | 0240906 A2 | 10/1987 |
| EP | 0261616 A2 | 3/1988 |
| EP | 0261616 A3 | 3/1988 |
| EP | 0270954 A1 | 6/1988 |
| EP | 0277289 A1 | 8/1988 |
| EP | 0293066 A2 | 11/1988 |
| EP | 0328775 A1 | 8/1989 |
| EP | 0228417 | 9/1990 |
| EP | 0229652 B1 | 10/1991 |
| EP | 0477135 A1 | 3/1992 |
| EP | 0277289 B1 | 4/1992 |
| EP | 0293066 B1 | 4/1993 |
| EP | 0270954 B1 | 5/1993 |
| EP | 0544144 A1 | 6/1993 |
| EP | 0583726 A2 | 2/1994 |
| EP | 0598606 A1 | 5/1994 |
| EP | 0636370 A1 | 2/1995 |
| EP | 0641195 A1 | 3/1995 |
| EP | 0647448 A1 | 4/1995 |
| EP | 0654263 A1 | 5/1995 |
| EP | 0661045 A1 | 7/1995 |
| EP | 0675710 A1 | 10/1995 |
| EP | 0682945 A2 | 11/1995 |
| EP | 0693475 A1 | 1/1996 |
| EP | 0820693 A1 | 1/1996 |
| EP | 0696598 A1 | 2/1996 |
| EP | 0216453 B1 | 3/1996 |
| EP | 0583726 131 | 11/1996 |
| EP | 0756480 A1 | 2/1997 |
| EP | 0760654 A1 | 3/1997 |
| EP | 0761211 A1 | 3/1997 |
| EP | 0780369 A1 | 6/1997 |
| EP | 0785775 A1 | 7/1997 |
| EP | 0809488 A1 | 12/1997 |
| EP | 0820698 A1 | 1/1998 |
| EP | 0820753 A2 | 1/1998 |
| EP | 0857062 A2 | 8/1998 |
| EP | 0864324 A1 | 9/1998 |
| EP | 0598606 B1 | 6/1999 |
| EP | 0675710 B1 | 8/1999 |
| EP | 0661045 81 | 7/2002 |
| EP | 1658054 A1 | 2/2005 |
| EP | 1658055 A1 | 2/2005 |
| EP | 1515702 B1 | 3/2005 |
| EP | 1527775 A1 | 4/2005 |
| EP | 1558221 A1 | 8/2005 |
| EP | 1558257 A1 | 8/2005 |
| EP | 1560585 B1 | 8/2005 |
| EP | 1611880 A2 | 1/2006 |
| EP | 1658054 B1 | 5/2006 |
| EP | 1740161 A2 | 1/2007 |
| EP | 1658055 B1 | 3/2007 |
| EP | 1765303 A1 | 3/2007 |
| EP | 1786403 A1 | 5/2007 |
| EP | 1558221 B1 | 6/2007 |
| EP | 1842533 A2 | 10/2007 |
| EP | 1845955 A1 | 10/2007 |
| EP | 1845956 A1 | 10/2007 |
| EP | 1859789 A1 | 11/2007 |
| EP | 1980245 A1 | 10/2008 |
| EP | 1897545 A1 | 12/2008 |
| EP | 2131830 A2 | 12/2009 |
| EP | 2246063 A1 | 11/2010 |
| EP | 2249811 A1 | 11/2010 |
| EP | 2273983 A1 | 1/2011 |
| EP | 2402004 A2 | 1/2012 |
| ES | 2336571 T3 | 12/2004 |
| ES | 2260042 T3 | 11/2006 |
| ES | 2285497 T3 | 11/2007 |
| ES | 2288621 T3 | 1/2008 |
| ES | 2289542 T3 | 2/2008 |
| ES | 2315505 T3 | 4/2009 |
| GB | 1147210 A | 4/1969 |
| GB | 1567727 A | 5/1980 |
| GB | 2047095 A | 11/1980 |
| GB | 2057878 A | 4/1981 |
| GB | 2238478 A | 6/1991 |
| HR | 20070456 T3 | 6/2007 |
| HR | 20070272 T3 | 11/2007 |
| JP | S36-022895 | 11/1961 |
| JP | S55162714 | 12/1980 |
| JP | S5659708 A | 5/1981 |
| JP | S56169622 A | 12/1981 |
| JP | S62240061 A | 10/1987 |
| JP | H0249719 A | 2/1990 |
| JP | 03-501737 A | 4/1991 |
| JP | H0517566 A | 1/1993 |

(56) References Cited

FOREIGN PATENT DOCUMENTS

| | | |
|---|---|---|
| JP | H06507645 A | 9/1994 |
| JP | 08053331 A | 2/1996 |
| JP | 8-505076 A | 6/1996 |
| JP | H09508410 A | 8/1997 |
| JP | H1057450 A | 3/1998 |
| JP | H10251149 A | 9/1998 |
| JP | 2002524150 A | 8/2002 |
| JP | 2002-275175 A | 9/2002 |
| JP | 2003125706 A | 5/2003 |
| JP | 2005506965 A | 3/2005 |
| JP | 2005515152 A | 5/2005 |
| JP | 2005534664 A | 11/2005 |
| JP | 2007501201 A | 1/2007 |
| JP | 2007501202 A | 1/2007 |
| JP | 2007513147 A | 5/2007 |
| JP | 2007533692 A | 11/2007 |
| JP | 2008024603 A | 2/2008 |
| JP | 2008504327 A | 2/2008 |
| JP | 2008528654 A | 7/2008 |
| JP | 2009523833 A | 6/2009 |
| JP | 2009531453 A | 9/2009 |
| JP | 2009537456 A | 10/2009 |
| JP | 2011504455 A | 2/2011 |
| JP | 2011506493 A | 3/2011 |
| JP | 2013536810 A | 9/2013 |
| JP | 2014505736 A | 3/2014 |
| JP | 2014528437 A | 10/2014 |
| KR | 1020060069832 A | 6/2006 |
| KR | 20070039041 A | 4/2007 |
| KR | 20070111510 A | 11/2007 |
| KR | 20090085312 A | 8/2009 |
| KR | 20100111303 A | 10/2010 |
| KR | 20110016921 A | 2/2011 |
| MX | 2007000008 A | 3/2007 |
| MX | 2007000009 A | 3/2007 |
| MX | 2007009393 A | 8/2007 |
| MX | 2010008138 A | 8/2010 |
| MX | 2010012039 A | 11/2010 |
| NO | 20061054 A | 3/2006 |
| NO | 20070578 A | 1/2007 |
| NO | 20074412 A | 11/2007 |
| NZ | 528302 A | 2/2007 |
| PT | 1699440 E | 12/2004 |
| PT | 1658054 E | 5/2006 |
| PT | 1658055 E | 7/2007 |
| PT | 1515702 E | 12/2008 |
| RU | 2131244 C1 | 6/1999 |
| RU | 2198197 C2 | 2/2003 |
| RU | 2396944 C2 | 7/2004 |
| RU | 2220715 C2 | 11/2004 |
| RU | 2326654 02 | 9/2005 |
| RU | 2339365 C2 | 12/2007 |
| RU | 2354357 C2 | 12/2007 |
| RU | 2007103712 A | 9/2008 |
| RU | 2007103707 A | 11/2008 |
| RU | 2007132975 A | 4/2009 |
| RU | 2567723 C2 | 11/2015 |
| SI | 1515702 T1 | 4/2009 |
| SI | 1699440 T1 | 11/2009 |
| SK | 10612003 A3 | 1/2004 |
| SU | 1759445 A1 | 9/1992 |
| TW | 1254634 B | 5/2006 |
| WO | WO 1980/000841 A1 | 5/1980 |
| WO | WO 1989/005624 A1 | 6/1989 |
| WO | WO 1990/003776 A1 | 4/1990 |
| WO | WO 1993/006723 A1 | 4/1993 |
| WO | WO 93/10765 a1 | 6/1993 |
| WO | WO 1993/010758 A1 | 6/1993 |
| WO | WO 1993/011749 A1 | 6/1993 |
| WO | WO 1993/023017 A1 | 11/1993 |
| WO | wo 1994/006414 A1 | 3/1994 |
| WO | WO 1994/008567 A1 | 4/1994 |
| WO | WO 1995/017174 A1 | 6/1995 |
| WO | WO 1995/020947 A1 | 8/1995 |
| WO | WO 1995/022319 A1 | 8/1995 |
| WO | WO 1995/030422 A1 | 11/1995 |
| WO | WO 1996/000066 A1 | 1/1996 |
| WO | WO 1996/003979 A1 | 2/1996 |
| WO | WO 1996/014058 A1 | 5/1996 |
| WO | WO 1997/000673 A1 | 1/1997 |
| WO | WO 1997/033566 A2 | 9/1997 |
| WO | WO 1997/049384 A1 | 12/1997 |
| WO | WO 1998/035655 A3 | 2/1998 |
| WO | WO 1998/020073 A2 | 5/1998 |
| WO | WO 1998/028698 A1 | 7/1998 |
| WO | WO 1998/035655 A1 | 8/1998 |
| WO | WO 1998/051758 A1 | 11/1998 |
| WO | WO 1999/012864 A1 | 3/1999 |
| WO | WO 1999/032120 A1 | 7/1999 |
| WO | WO 1999/044591 A1 | 9/1999 |
| WO | WO1999/045887 A2 | 9/1999 |
| WO | WO 1999/048481 A1 | 9/1999 |
| WO | WO 2000/013647 A1 | 3/2000 |
| WO | WO 2000/033835 A1 | 6/2000 |
| WO | WO 2000/040205 A2 | 7/2000 |
| WO | WO 2001/008661 A2 | 2/2001 |
| WO | WO 2001/012230 A1 | 2/2001 |
| WO | WO 2001/052651 A2 | 7/2001 |
| WO | WO 2001/058451 A1 | 8/2001 |
| WO | WO 2001/015667 A1 | 12/2001 |
| WO | WO 2001/097783 A1 | 12/2001 |
| WO | WO 2002/026061 A1 | 4/2002 |
| WO | WO 2002/026262 A2 | 4/2002 |
| WO | WO 2002/026928 A1 | 4/2002 |
| WO | WO 2002/035991 A2 | 5/2002 |
| WO | WO 2002/071860 A1 | 9/2002 |
| WO | WO 2002/088217 A1 | 11/2002 |
| WO | WO 2002/094254 A2 | 11/2002 |
| WO | WO 2003/006723 A1 | 1/2003 |
| WO | WO 2003/013433 A2 | 2/2003 |
| WO | WO 2003/013476 A1 | 2/2003 |
| WO | WO 2003/013479 A1 | 2/2003 |
| WO | WO 2003/013538 A1 | 2/2003 |
| WO | WO 2003/015531 A2 | 2/2003 |
| WO | WO 2003/018015 A1 | 3/2003 |
| WO | WO 2003/024426 A1 | 3/2003 |
| WO | WO 2003/024430 A1 | 3/2003 |
| WO | WO 2003/026624 A1 | 4/2003 |
| WO | WO 2003/026743 A2 | 4/2003 |
| WO | WO 2003/028698 A1 | 4/2003 |
| WO | WO 2003/028990 A1 | 4/2003 |
| WO | WO 2003/031546 A1 | 4/2003 |
| WO | WO 2003/035029 A1 | 5/2003 |
| WO | WO 2003/035053 A1 | 5/2003 |
| WO | WO 2003/035054 A1 | 5/2003 |
| WO | WO 2003/035177 A2 | 5/2003 |
| WO | WO 2003/039561 A1 | 5/2003 |
| WO | WO 2003/049689 A2 | 6/2003 |
| WO | WO 2003/053417 A2 | 7/2003 |
| WO | WO 2003/068392 A1 | 8/2003 |
| WO | WO 2003/070191 A1 | 8/2003 |
| WO | 2003526598 A | 9/2003 |
| WO | WO 2003/092648 A1 | 11/2003 |
| WO | WO 2003/094812 A1 | 11/2003 |
| WO | WO 2003/105808 A1 | 12/2003 |
| WO | WO 2004/004693 A1 | 1/2004 |
| WO | WO 2004/043967 A1 | 2/2004 |
| WO | WO 2004/026262 A2 | 4/2004 |
| WO | WO 2004/026263 A2 | 4/2004 |
| WO | WO 2004/026280 A2 | 4/2004 |
| WO | WO 2004/037230 A1 | 5/2004 |
| WO | WO 2004/037259 A1 | 5/2004 |
| WO | WO 2004/037260 A1 | 5/2004 |
| WO | WO 2004/066910 A2 | 8/2004 |
| WO | WO 2004/078212 A1 | 9/2004 |
| WO | WO 2004/084869 A1 | 10/2004 |
| WO | WO 2004/093801 A2 | 11/2004 |
| WO | WO 2004/093819 A2 | 11/2004 |
| WO | WO 2004/098567 A2 | 11/2004 |
| WO | WO 2004/100894 A2 | 11/2004 |
| WO | WO 2005/016313 A1 | 2/2005 |
| WO | WO 2005/016314 A1 | 2/2005 |
| WO | WO 2005/032524 A2 | 4/2005 |
| WO | WO 2005/041968 A2 | 5/2005 |

(56) References Cited

FOREIGN PATENT DOCUMENTS

| | | |
|---|---|---|
| WO | WO 2005/053587 A1 | 6/2005 |
| WO | WO 2005/053656 A1 | 6/2005 |
| WO | WO 2005/055981 A2 | 6/2005 |
| WO | WO 2005/060942 A1 | 7/2005 |
| WO | WO 2005/063214 A1 | 7/2005 |
| WO | WO 2005/065646 A2 | 7/2005 |
| WO | WO 2005/066183 A1 | 7/2005 |
| WO | WO 2005/079760 A1 | 9/2005 |
| WO | WO 2005/102286 A1 | 11/2005 |
| WO | WO 2005/102294 A2 | 11/2005 |
| WO | WO 2005/102294 A3 | 11/2005 |
| WO | WO 2005/105036 A1 | 11/2005 |
| WO | WO 2006/002883 A1 | 1/2006 |
| WO | WO 2006/002884 A1 | 1/2006 |
| WO | WO 2006/002886 A1 | 1/2006 |
| WO | WO 2006/002884 B1 | 3/2006 |
| WO | WO 2006/039692 A2 | 4/2006 |
| WO | WO 2006/058249 A2 | 6/2006 |
| WO | WO 2006/082097 A1 | 8/2006 |
| WO | WO 2006/082099 A1 | 8/2006 |
| WO | WO 2006/105615 A1 | 10/2006 |
| WO | WO 2006/128471 A2 | 12/2006 |
| WO | WO 2007/005716 A2 | 1/2007 |
| WO | WO 2007/008752 A2 | 1/2007 |
| WO | WO 2007/014061 A2 | 2/2007 |
| WO | WO 2007/048233 A1 | 5/2007 |
| WO | WO 2007/053698 A2 | 5/2007 |
| WO | WO 2007/085024 A2 | 7/2007 |
| WO | WO 2007/085024 A3 | 7/2007 |
| WO | WO 2007/103105 A2 | 9/2007 |
| WO | WO 2007/103286 A2 | 9/2007 |
| WO | WO 2007/112273 A2 | 10/2007 |
| WO | WO 2007/112285 A2 | 10/2007 |
| WO | WO 2007/112286 A2 | 10/2007 |
| WO | WO 2007/131357 A1 | 11/2007 |
| WO | WO 2008/023261 A1 | 2/2008 |
| WO | WO 2008/033523 A1 | 3/2008 |
| WO | WO 2008/069941 A2 | 6/2008 |
| WO | WO 2008/086804 A2 | 7/2008 |
| WO | WO 2008/07149 A3 | 9/2008 |
| WO | WO 2008/107149 A2 | 9/2008 |
| WO | WO 2008/109462 A2 | 9/2008 |
| WO | WO 2008/132707 A1 | 11/2008 |
| WO | WO 2008/142627 A2 | 11/2008 |
| WO | WO 2008/148798 A2 | 12/2008 |
| WO | WO 2009/005803 A1 | 1/2009 |
| WO | WO 2009/014534 A1 | 1/2009 |
| WO | WO 2009/034541 A2 | 3/2009 |
| WO | WO 2009/034541 A3 | 3/2009 |
| WO | WO 2009/034541 A9 | 3/2009 |
| WO | WO 2009/035474 A1 | 3/2009 |
| WO | WO 2009/051819 A1 | 4/2009 |
| WO | WO 2009/076764 A1 | 6/2009 |
| WO | WO 2009/092601 A1 | 7/2009 |
| WO | WO 2009/110005 A2 | 9/2009 |
| WO | WO 2009/112273 A2 | 9/2009 |
| WO | WO 2009/135680 A1 | 11/2009 |
| WO | WO 2010/022193 A2 | 2/2010 |
| WO | WO 2010/044842 A1 | 4/2010 |
| WO | WO 2010/057036 A2 | 5/2010 |
| WO | WO 2010/066034 A1 | 6/2010 |
| WO | WO 2010/069050 A1 | 6/2010 |
| WO | WO 2010/083843 A1 | 7/2010 |
| WO | WO 2010/083894 A1 | 7/2010 |
| WO | WO 2010/088911 A1 | 8/2010 |
| WO | WO 2010/105672 A1 | 9/2010 |
| WO | WO 2010/140007 A2 | 12/2010 |
| WO | WO 2010/140007 A9 | 12/2010 |
| WO | WO 2010/149169 A2 | 12/2010 |
| WO | WO 2011/008298 A2 | 1/2011 |
| WO | WO 2011/009602 A1 | 1/2011 |
| WO | WO 2011/009603 A1 | 1/2011 |
| WO | WO 2011/009604 A1 | 1/2011 |
| WO | WO 2011/095314 A2 | 8/2011 |
| WO | WO 2011/095314 A3 | 8/2011 |
| WO | WO 2011/128630 A2 | 10/2011 |
| WO | WO 2011/154414 A1 | 12/2011 |
| WO | WO 2012/028317 A1 | 3/2012 |
| WO | WO 2012/028318 A1 | 3/2012 |
| WO | WO 2012/028319 A1 | 3/2012 |
| WO | WO 2012/061779 A1 | 5/2012 |
| WO | WO 2012/076907 A2 | 6/2012 |
| WO | WO 2012/119727 A1 | 9/2012 |
| WO | WO 2012/166474 A1 | 12/2012 |
| WO | WO 2013/003845 A1 | 1/2013 |
| WO | WO 2013/017234 A1 | 2/2013 |
| WO | WO 2013/017242 A1 | 2/2013 |
| WO | WO 2013/030177 A1 | 3/2013 |
| WO | WO 2013/050539 A2 | 4/2013 |
| WO | WO 2013/072395 A1 | 5/2013 |
| WO | WO 2013/084059 A1 | 6/2013 |
| WO | WO 2013/127830 A1 | 9/2013 |
| WO | WO 2013/127831 A1 | 9/2013 |
| WO | WO 2013/128276 A2 | 9/2013 |
| WO | WO 2013/156453 A1 | 10/2013 |
| WO | WO 2013/167735 A1 | 11/2013 |
| WO | WO 2014/059512 A1 | 4/2014 |
| WO | WO 2014/190440 A1 | 12/2014 |
| WO | WO 2014/191396 A1 | 12/2014 |
| WO | WO 2014/191397 A1 | 12/2014 |
| WO | WO 2015/004245 A1 | 1/2015 |
| WO | WO 2015/103379 A1 | 7/2015 |

OTHER PUBLICATIONS

Andre et al., "O-Demethylation of Opiod Derivatives With Methane Sulfonic Acid/Methoinine: Application to the Synthesis of Naloxone and Analogues" Synthetic Comm. 22(16), pp. 2313-2327, 1992.

Apicella A.et al., Biomaterials, vol. 14, No. 2, pp. 83-90,1993.

Application of a modelling system in the formuiation of extended release hydrophilic matrices, Reprinted from Pharmaceutical Technology Europe, Jul. 2006.

Application of Opadry II, complete film coating system, on metformin HCI extended release matrices containing Polyox water soluble resin, Colorcon Apr. 2009.

Arnold C., "Teen Abuse of Painkiller OxyContin on the Rise," www.npr.org, Dec. 19, 2005.

Augustine, R.L., Catalytic Hydrogenation of a, B-Unsaturated Ketones. III The Effect of Quantity and Type of Catalysts,' J.Org Chem. 28(1), pp. 152-155, Abstract 1963.

Avis, Kenneth, Parenteral Preparations. Chapter 85. pp. 1518-1541In Remington's Pharmaceutical Sciences, 17th Ed, 1985.

Bailey, F.E., et al., "Some properties of poly(ethylene oxide)' in aqueous solution," Journal of Applied Polymer Science, vol. 1, Issue No. 1, pp. 56-62, 1959.

Bauer et al. Lehrbuch der Pharmazeutischen Technologie. Eight Edition 2006. Stuttgart, pp. 343-352.

Bauer et al. Lehrbuch der Pharmazeutischen Technologie. Sixth Edition 1999. Stuttgart, pp. xIX-XV, Table of contents. (Full English translation attached).

Bauer, Kurt H., et al., Coated Pharmaceutical Dosage Forms—Fundamentals, Manufacturing Techniques, Biopharmaceutical Aspects, Test Methods and Raw Materials, 1st edition, 1998, CRC Press, Medpharm Scientific Publishers. (Preface, Table of Content, List of Abbreviations, Explanation of Terms only).

Baum et al.,"The impact of the addition of naloxone on the use and abuse of pentazocine", Public Health Reports, Jul.-Aug. 1987, vol. 102, No. 4, p. 426-429.

Block, Lawrence. Medicated Applications. Chapter 88. In Remington's Pharmaceutical Sciences, 17th Ed, 1985.

Braun, et al. A study of Bite Force. Part 2: Relationship to Various cephalometric Measurements. Angel Orthodontist, vol. 65 (5) pp. 373-377, 1995.

Brown, The Dissolution Procedure: Development and Validation, heading "Study Design", "Time Points" US Pharmacopoeia (USP), vol. 31(5), General Chapter 1092, pp. 1 -15, 2006.

Caraballo, Journal of Controlled Release, vol. 69, pp. 345-355, 2000.

(56) References Cited

OTHER PUBLICATIONS

Carbopol 71G, retrieved Mar. 10, 2014 from http://www.lubrizol.com/LifeScience/Products/Carbopol71G-NF.html.
Cawello, "Parameters for Compartment-free Pharmacokinetics—Standardization of Study Design, Data Analysis and Reporting" 1999, pp. XI-XIII (table of contents).
Committee for Proprietary Medicinal Products. Note for Guidance on the Investigation of Bioavailability and Bioequivalence. 2001. pp. 1-18.
Coppens et al., "Hypromellose, Ethylcellulose, and Polyethylene Oxide Use in Hot Melt Extrusion"; Pharmaceutical Technology, 62-70, Jan. 2005.
Cornish, P. "Avoid the Crush": hazards of medication administration in patients with dysphagia or a feeding tube, CMA Media Inc., CMAJ. 172(7), pp. 871-872, 2005.
Costa et al. "Modeling and comparison of dissolution profiles"; European Journal of Pharmaceutical Sciences 13 (2001) 123-33.
Crowley M.M. et al., "Stability of polyethylene oxide in matrix tablets prepared by hot-metl extrusion," Biomaterials 23, 2002, pp. 4241-4248.
Crowley MM, Drug Dev Ind Pharm. Sep. 2007; 33(9);909-26. (Abstract only).
Dachille et al., "High-pressure Phase Transformations in Laboratory Mechanical Mixers and Mortars", Nature, vol. 186, Apr. 2, 1960, pp. 34 and 71.
Dachille, F. et al., "High-Pressure Phase Transformation in Laboratory Mechanical Mixers and Mortars", 1960., Nature, vol. 186, pp. 1-2 (abstract).
Davies, et al; European Journal of Pharmaceutics and Biopharmaceutics, 67, 2007, pp. 268-276.
Dean, D.A., E.R. Evans, I.H. Hall, Pharmaceutical Packaging Technology, Taylor & Francis, 1st Edition, Nov. 30, 2000 (Publisher description dated Oct. 22, 2010).
Deighan, C.J. et al.. Rhabdomyolysis and acute renal failure resulting from alcohol and drug abuse, Q.J. Med, vol. 93, 2000, pp. 29-33.
Dejong (Pharmaceutisch Weekblad Scientific Edition) 1987, p. 24-28.
Dexheimer, Terahertz Spectroscopy: Principles and Applications (Optical Science and Engineering Series), CRC; 1 edition 2007. (Table of content only)
Dierickx et al., "Co-extrusion as manufacturing technique for fixed-dose combination mini-matrices," European Journal of Pharmaceutics and Biopharmaceutics 81 (2012), 683-689.
Disanto, Anthony. Bioavailability and Bioequivalency Testing. Chapter 77. In Remington's Pharmaceutical Sciences, 17th Ed, 1985.
Dow Chemical Company, "Using Dow Excipients for Controlled Release of Drugs in Hydrophilic Matrix Systems", Sep. 2006, pp. 1-36.
Dow Excipients Chem. of Poly. Water Soluble-Resin 2004, pp. 1-2.
Dow Technical Data, Polyox WSR Solid Dosage Formulation via Melt Extrusion, Feb. 2003, pp. 1-3.
Efentakis M et al. "Evaluation of High Molecular Weight Poly(Oxyethylene) (Polyox) Polymer: Studies of Flow Properties and Release Rates of Furosemide and Captopril from controlled-Release hard Gelatin Capsules", Pharmaceutical Development and Technology, 5 (3), pp. 339-346, 2000.
Eggleston, "The seat of the emetic action of various drugs," J. Pharmacol. Exp. Ther. 7, 225-253 (1915).
El-Egakey, Adel et al, "Hot extruded dosage forms Part I Technology and dissolution kinetics of polymeric matrices" Pharmacerutica Acta Helvetiae, vol. 46, pp. 31-53,Mar. 19, 1970.
El-Sherbiny I.M. et al "Preparation, characterization, swelling and in vitro drug release behaviour of poly[N-acryloylglycine-chitosan] interplymeric pH and thermally-resposive hydrogels", European Polymer Journal, vol. 41, pp. 2584-2591, 2005.
Encyclopedia of Pharmaceutical Technology, Third Edition, vol. 1, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 2, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 3 edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 4, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 5, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 6, edited by James Swarbrick PharmaceuTech, Inc., Pinehurst, North Carolinia, USA (Table of Contents only), Oct. 25, 2006.
Encyclopedia of Pharmacological Technology, Informa Healthcare, 1st Ed., 1996, vol. 14 (Table of Content only).
Erskine, Jr., Clyde. Quality Assurance and Control. Chapter 83 pp. 1487-1491 in Remington's Pharmaceutical Sciences, 17th Ed, 1985.
Eudragit NE4OD web page from Evonik website; downloaded Feb. 24, 2015.
Eudragit RS PO web page from Evonik website; downloaded Feb. 24, 2015.
European Pharmacopoeia 2.9.40 "Uniformity of Dosage Units", 2006, pp. 3370-3373.
European Pharmacopoeia 5.0, 2.9.8 "Resistance to Crushing of Tablets", 2005, p. 235.
European Pharmacopoeia, Third Edition Supplement 2000, Council of Europe, Strasbourg, 2000 pp. 85-107.
European Pharmacopoeia, Third Edition, Council of Europe, Strasbourg, 1997, pp. 127-152.
European Search Report and Opinion Application No. 12002708.1-1219, Sep. 24, 2012.
European Search Report and Opinion Application No. 14176277.3-1460, dated Dec. 15, 2014.
European Search Report and Opinion, Application No. 11006253.6-2112, dated Dec. 16, 2011.
European Search Report and Opinion, Application No. 11006254.4-2112, dated Dec. 16, 2011.
European Search Report and Opinion, Application No. 11008131.2-1219, dated Feb. 24, 2012.
European Search Report and Opinion, Application No. 11009129.5-2112, dated Apr. 10, 2012.
European Search Report and Opinion, Application No. 12001296.8-1219, dated Jun. 26, 2012.
European Search Report and Opinion, Application No. 12001301.6-1219, dated Jun. 26, 2012.
European Search Report and Opinion, Application No. 12003743.7-1219, dated Sep. 24, 2012.
European Search Report and Written Opinion for EP Application No. 13169658.5, dated Aug. 6, 2013.
European Search Report and Written Opinion for EP Application No. 13169659.3, dated Aug. 6, 2013.
European Search Report and Written Opinion for EP Application No. 13176309.9-1460, dated Oct. 9, 2013.
European Search Report and Written Opinion for EP Application No. 13197503.9-1460, dated Feb. 18, 2014.
European Search Report and Written Opinion for EP Application No. 13425151.1-1460, dated Mar. 11, 2014.
European Search Report and Written Opinion for EP Application No. 14169801.9-1455 dated Oct. 20, 2014.
Evaluation of Verapamil HCL (240 mg) Extended Release Matrix Formulation Using USP Apparatus III in Biorelevant Dissolution Media, Jul. 2009.
Evonik Industries, Eudragit Application Guidelines, 10th Edition, 2008, (Table of Contents only).
Evonik Rohm GmbH product brochure: EUDRAGIT acrylic polymers for solid oral dosage forms.
Fell J.T., et al, "Determinination of Tablet Strength by the Diametral-Compression Test" Journal of Pharmaceutical Sciences, vol. 59, No. 5, May 1970, pp. 688-691.
Follonier N. et al., "Evaluation of hot-melt extrusion as a new technique for the production of polymer-based pellets for sustained

(56) References Cited

OTHER PUBLICATIONS release capsules containing high loadings of freely soluble drugs," Drug Development and Industrial Pharmacy, 20(8), pp. 1323-1339, 1994.
Follonier, N. et al., "Various ways of modulating the release of ditiazem hydrochloride from hot-melt extruded sustained release pellets prepared using polymeric materials" Journal of Controlled Release 36, pp. 243-250, 1995.
Formulation of Polyox ER Matrices for a Highly Soluble Active, Colorcon Jul. 2009.
Foye, W., Principles of Medicinal Chemistry; Analgesics pp. 241-242, at 241 (1989).
Foye, W., Principles of Medicinal Chemistry; Structural Features and Pharmacologic Activity, pp. 63-66 at 65 (1989).
Freed et al., "pH Control of Nucleophilic/electrophilic oxidation", International Journal of Pharmaceutics, vol. 357, pp. 180-188 (2008).
Giles R. et al. Plastic Packaging Materials. Chapter 81. pp. 1473-1477 in Remington's Pharmaceutical Sciences. 17th Ed. 1985.
Glyceryl behenate monograph; European Pharmacopeia 5.0; dated Jan. 2005; downloaded Feb. 24, 2015.
Goodman and Gilman, "The Pharmacological Basis of Therapeutics, Seventh Edition", MacMillan Publishing Company, Table of Contents. 1985.
Goodman and Gilman, 1985, 7th edition, chapter 22, 491-530.
Goodman and Gilman, 1985, 7th edition, chapter 23, 533-579.
Graham N.B., Poly(Ethylene Glycol) Chemistry: Biotechnical and Biomedical Applications, p. 263-291 Chapter 17, 1992.
Griffin W, "Classification of Surface-Active Agents by HLB" Journal of the Society of Cosmetic Chemists, Atlas Powder Company, 1949, pp. 311-326,.
Griffith, et al. "Tablet Crushing and the Law: The Implications for Nursing" Professional Nurse 19(1), pp. 41-42, 2003.
Gryczke et al. "Development and evaluation of orally disintegrating tablets (ODTs) containing Ibuprofen granules prepared by hot melt extrusion", Colloids and surfaces., B, Biointerfaces, Elsevier, Amsteram, NL, vol. 86, No. 2, Apr. 5, 2011, pp. 275-284.
Guidance for industry—Bioavailability and Bioequivalence—Studies for Orally Administered Drug Products—General Considerations, FDA, BP, Announced in the Federal Register: vol. 68, No. 53/Mar. 19, 2003.
Guidance for industry—Statistical Approaches to Establishing Bioequivalence, FDA, BP, Jan. 2001.
Handbook of Pharmaceutical Excipients, 1935, American Pharmaceutical Association, Washington, DC and London (Table of Content Only).
Handbuch der Kunststoff-Extrusionstechnik 1, "Grundlagen" in Chapter 1.2 "Klassifizierung von Extrudern", pp. 3-7. 1989. (Full english translation attached).
Hanning C.D.et al. "The Morphone Hydrogel Suppository. A New Sustained release Rectal Preparation", British Journal of Anaesthesia, 61, pp. 221-227, 1988.
Hartauer, Kerry J. "Influence of Peroxide Impurities in Povidone and Crospovidone on the Stability of Raloxife" Pharma. Dev. & Tech, 5 (3) 303-310 (2000).
Henriest D. et al. In vitro and in vivo evaluation of starch-based hot stage extruded double matrix systems. Journal of Controlled Release. 2001, vol. 75, pp. 391-400.
Hoepfner et al. Fiedler Encyclopedia of Excipients. Sixth Edition, 2007, Aulendorf, Germany; Table of Contents only.
Hong S. et al. Dissolution kinetics and physical characterization of three-layered tablet with poly(ethylene oxide) core matrix capped by Carbopol. Int .J. Pharmacol. 2008, vol. 356, pp. 121-129.
Inert gas—Wikipedia, Dec. 2009, pp. 1-3.
Investigation of a Directly Compressible Metformin HCl 500mg Extended Release Formulation Based on Hypromellose, Colorcon Jul. 2009.
James, A. "The legal and clinical implications of crushing tablet medication", Nurse Times 100(50), 28-33, 2004.

Janicki S. et al. "Slow-Release Microballs: Method of Preparation" Acta Pharm. Technol. 33(3) 154-155, 1987.
Jannetto, P. et al, "Oxycodone: Recognition and Pharmacogenomics," Toxicology News, Mar. 2003, 1-7.
Kalant H. et al., Death in Amphetamine Users: Caues and Rates, CMA Journal, vol. 112 (Feb. 8, 1975): 299-304.
Katz N. et al. "Challenges in the development of prescription opioid abuse-deterrent formulations", Clin. J. Pain, 23(8): 648-660 (Oct. 2007).
Kim C.-J. "Drug Release from Compressed Hydrophilic Polyox-WSR Tablets" J Pharm. Sciences 1995, 84(3): pp. 303-306.
Kim N et al. "Preparation and Evaluation of Eudragit Gels. V. Rectal Gel Preparations for Sustained Release and Avoidance of First-Pass Metabolism of Lidocaine", Chem. Pharm Bull. 1992 40(10), 2800-2804.
King et al. Oral Solid Dosage Forms. Chapter 90. pp. 163-1632 in Remington's Pharmaceutical Sciences, 17th Ed, 1985.
King, R, "Tablets, Capsules, and Pills" Remington's Pharmaceutical Sciences, pp. 1553-1593, Ch. 89, 1980, $16^{th}$ Edition.
King, Remington's Pharmaceutical Sciences 17th ed., Chapter 78, p. 1418 (1985).
Knevel, Adelbert. Separation. Chapter 78. pp. 1432-1442 in Remington's Pharmaceutical Sciences, 17th Ed, 1985.
Kolter, K., "Compression Behaviour of Kollidon SR," APV/ APGI 2002, Florence, Apr. 11, 2002.
Kondrat, T. , "Technology dosage forms" Moscow 1991, p. 96.
Lee, Y.-S. et al., Principles of Terahertz Science and Technology (Lecture Notes in Physics), Springer; 1 edition 2008. (Table of Contents Only).
Lenindzer, A., "The molecular basis of the structure and functions of cells" Moscow 1974, p. 68.
Levina et al., "The Effect of Ultrasonic Vibration on the Compaction Characteristics of Ibuprofen" Drug Development and Industrial Pharmacy, vol. 28, No. 5, pp. 495-514, 2002.
Levina M. et al "The Effect of Ultrasonic Vibration on the Compaction Characteristics of Paracetamol", Journal of Pharmaceutical Sciences, vol. 89, No. 6, pp. 705-723, Jun. 2000.
Li et al, "Characterization of Poly(Ethylene Oxide) as a Drug Carrier in Hot-Melt Extrusion", Drug Development and Industrial Pharmacy, vol. 32, No. 8, Jan. 1, 2006, pp. 991-1002.
Lieberman, Herbert A., Pharmaceutical Dosage Forms, Tablets, Second Edition, Revised and Expanded, 1990. vol. 2 (Cover and Table of Content only).
Lintner, Carl. Stability of Pharmaceuticai Products. Chapter 82. pp. 1478-1486 in Remington's Pharmaceutical Sciences, 17th Ed, 1985.
Liu J. et al., "Properties of Lipophilic Matrix Tables Containing Phenylpropanolamine Hydrochloride Prepared by Hot-Melt Extrusion", EJPB, 52 (2001), pp. 181-190.
Lockhart H. et al, "Packaging of Pharmaceuticals and Health Care Products"; Blackie & Professional; First Edition 1996. (Table of contents only).
Longer et al, Sustained-Release Drug Delivery Systems. Chapter 92. pp. 1611-1661 in Remington's Pharmaceutical Sciences, 17th Ed, 1985.
Madorsky S.L. "Thermal degradation of Polyethylene Oxide and Polypropylene Oxide", Journal of Polymer Science, pp. 183-194 vol. 36, No. 3, Mar. 1959.
Maggi et al., "Dissolution behavior of hydrophilic matrix tablets containing two different polyethylene oxides (PEOs) for the controlled release of a water-soluble drug. Dimensionality study" Biomaterials, 2002, 23, 1113-1119.
Maggi L.etal, "High molecular weight polyethylene oxides (PEOs) as an alternative to HPMC in controlled release dosage form", 2000, International Journal of Pharmaceutics, 195 pp. 229-238.
Maggi, C., Therapeutic Potential of Capsaicin-like Molecules. Life Sciences, vol. 51, pp. 1777-1781, 1992.
Mank R. et al., "Darstellung wirkstoffhaltiger Extrusionsformlinge auf der Basis von Thermoplasten. Teil 1: Untersuchung zur Wirkstoffliberation" Pharmazie 44, H. 11, pp. 773-776, 1989. English language translation of relevant paragraph provided.
Mank R., "Darstellung wirkstoffhaltiger Extrusionsformlinge auf der Basis von Thermoplasten. Teil 2: Unersuchungen zur

(56) References Cited

OTHER PUBLICATIONS

Optimierung der Wirkstofffreigabe" Pharmazie 45, H. 8, pp. 592-593 1990. English language translation of relevant paragraph provided.
Marques, Tablet breaking force, 2008.
Matos, Dr. Rick, Ph.D—Letter Jan. 6, 2011.
McGary, C.W., Jr. "Degradation of Poly(ethylene Oxide)", Journal of Polymer Science vol. XLVI 1960, pp. 51-57.
McGinity et al., Hot-Melt Extrusion as a Pharmaceutical Process, American Pharmaceutical Review, vol. 4 (2), pp. 25-36, 2001.
McGinity, J.W.—Letter of Jan. 26, 2009, pp. 1-4.
McNeill M. et al. Properties controlling the diffusion and release of water-soluble solutes from poly(ethylene oxide) hydrogels. 4. Extended constant rate release from partly-coated spheres. Journal Biomet. Sci. Polymer. Ed. 1996, vol. 7, pp. 953-963.
Mesiha M.S. et al "A Screening Study of Lubricants in Wet Powder Passes Suitable for extrusio-spheronization", Drug Development and Industrial Pharmacy. 19(8), pp. 943-959, 1993.
Metformin Hydrochloride 1000 mg Extended Release Tablets, Lubrizol Advanced Materials, Inc., Nov. 20, 2009, Previous Edition Dec. 19, 2008.
Metformin Hydrochloride 750 mg Extended Release Tablets, Lubrizol Advanced Materials, Inc., Sep. 2010.
Miles, R.E. et al., Terahertz Frequency Detection and Identification of Materials and Objects (NATO Science for Peace and Security Series B: Physics and Biophysics), Springer; 1 edition 2007. (Table of contents).
Miller "To crush or not to crush? What to consider before giving medications to a patent with a tube or who has trouble swallowing", Nursing, pp. 50-52, Feb. 2000.
Mises à jour cumulatives, Vidal, Jan./Oct. 2002 (full translation attached).
Mitchell, "Oral Dosage Forms That Should Not Be Crushed: 2000 Update" Hospital Pharmacy 35(5), 553-557, 2000.
Moorman-Li, R. et al, "A Review of Abuse-Deterrent Opioids for Chronic Nonmalignant Pain." Pharmacy and Therapeutics, vol. 37 No. 7, Jul. 2012, pp. 412-421.
Morissette et al. Advanced Drug Delivery Review 26 (2004), 275-300.
Moroni A. et al, "Application of Poly(Oxyethylene) Homopolymers in Sustained release Solid formulations" Drug Development and Industrial Pharmacy, 21(12) pp. 1411-1428, 1995.
Mullins, John. Ophthalmic Preparations, Chapter 87. pp. 1553-1563; In Remington's Pharmaceutical Sciences, 17th Ed, 1985.
Munjal M. et al., "Polymeric Systems for Amorphous Delta^9—Tetrahydrocannabinol Produced by a Hot-Melt Method. Part II: Effect of Oxidation Mechanisms and Chemical Interactions on Stability" Journal of Pharmaceutical Sciences vol. 95 No. 11, Wiley InterScience, 2006, pp. 2473-2485.
Munsell Color Company, "The Munsell Book of Color: Glossy Collection", X-Rite, Originally published in 1966, pp. 1-7.
Nairn, J.G., Solutions, Emulsion, Suspensions and Extractives. Chapter 84. pp. 1492-1517, In Remington's Pharmaceutical Sciences, 17th Ed, 1985.
Note for Guidance on Stability Testing, EMEA, Aug. 2003, pp. 1-20.
Note for Guidance on the Investigation of Bioavailability and Bioequivalence, EMEA, London, Jul. 26, 2001 (CPMP/EWP/QWP/1401/98).
Ohnishi N. et al., Effect of the Molecular Weight of Polyethylene Glycol on the Bioavailability of Indomethacin Sustained-Release suppoositories Prepared with Solid Dispersion, Chem. Pharm. Bull, 35(8), pp. 3511-3515, 1987.
Oliveira et al., "Production and characterization of laminar coextrudates at room temperature in the absence of solvents," AAPS Annual Meeting and Exposition, Oct. 14-18, 2012, Chicago, USA.
Oxicotin: Balancing Risks and Benefits, United States Senate, Hearing, Feb. 12, 2002.

Oxycodon (Oxygenic): Missbrauch, Abhaengigkeit und toedliche Folgen durch Injection zerstossener Retardtabletten, Deutsches Ärzteblatt, vol. 36, A2326-A2326, Sep. 5, 2003.
Ozeki T. et al. "Control of Medicine Release From Solid Dispersion Through Poly(ethylene oxide)-Carboxyvinylpolymer Interaction", International Journal of Pharmaceutics, 165, 1998, pp. 239-244.
Ozeki T. et al. "Controlled Release From Solid Dispersion Composed of Poly(ethylene oxide)—Carbopol Interpolymer Complex With Various Cross-Linking Degrees of Carbopol", Journal of Controlled Release. 63, 2000. pp. 287-295.
Ozeki T. et al., "Control of medicine release from solid dispersion composed of the poly(ethylene oxide)-carboxyviyipolymer interpolymer complex by varying molecular wight of polyethylene oxide)"Journal of Controlled Release 58, pp. 87-95, 1999.
PCT International Search Report and Written Opinion for PCT Application No. PCT/EP2010/004459 dated Dec. 1, 2010.
PCT International Search Report and Written Opinion for PCT Application No. PCT/EP2009/003290 dated Jul. 9, 2009.
PCT International Search Report and Written Opinion for PCT Application No. PCT/EP2013/053894 dated Mar. 22, 2013.
PCT International Search Report and Written Opinion for PCT Application No. PCT/EP2013/057851 dated Jun. 12, 2013.
PCT International Search Report and Written Opinion for PCT Application No. PCT/EP2013/059728 dated Aug. 6, 2013.
PCT International Search Report and Written Opinion for PCT Application No. PCT/EP2014/064830 dated Aug. 6, 2014.
PCT International Search Report and Written Opinion for PCT Application No. PCT/EP2014/075618 dated Feb. 11, 2015.
PCT International Search Report and Written Opinion for PCT Application No. PCT/EP2014/0777748 dated Feb. 12, 2015.
PCT Second Written Opinion for PCT Application No. PCT/EP2013/053893 dated Feb. 21, 2014.
PCT Second Written Opinion for PCT Application No. PCT/EP2013/057851 dated Apr. 15, 2014.
Pentoxifylline 400 mg Extended Release Tablets, Lubrizol Advanced Materials Inc., Mar. 3, 2011, Previous Edition Nov. 19, 2009.
Perez-Marcos, B., Usefulness of certain varieties of Carbomer in the formulation of hydrophilic furosemide matrices, International Journal of Pharmaceutics, 67 (1991) 113-121.
Pharm. Research, Official Journal of the American Association of Pharmaceutical Scientists, Sep. 1989, 6(9), S-98.
Pharm. Research, Official Journal of the American Association of Pharmaceutical Scientists, Oct. 1991. 8(10), S-192.
Phillips, G. Briggs. Sterilization. Chapter 79. pp. 1443-1454, In Remington's Pharmaceutical Sciences, 17th Ed, 1985.
Physico-mechanical Characterization of Polyox for Table Manufacture, Colorcon Jul. 2009.
Pillay V. et al. A novel approach for constant rate delivery of highly soluble bioactives from a simple monolithic system. Journal of Controlled Release. 2000, vol. 67, pp. 67-78.
Pinto, Joao F. et al.,"Evaluation of the Potential Use of Poly(ethylene oxide) as Tablet- and Extrudate-Forming Material," AAPS PharmSci, 2004; 6 (2), Article 15, pp. 1-10, (http://www.aapspharmsci.org).
Piringer, O.G.and A.L. Baner, Plastic Packaging: Interactions with Food and Pharmaceuticals, Wiley VCH, 2nd Completely Revised Edition, Feb. 13, 2008. (Table of Contents only).
Polyox water soluble resins 2003. http://www.dow.com/webapps/lit/litorder.asp?filepath=polyox/pdfs/noreg/326-00002.pdf
Polyox water-soluble resins (DOW Mar. 2002); see http://msds-search.dow.com/PublishedLiteratureDOWCOM/dh_0031/0901b80380031a4a.pdf?filepath=/326-00001.pdf
&fromPage=GetDoc).
Polyox WSR-303, retrieved Mar. 10, 2014 from URL http://www.dow.com/dowwolff/en/industrial_solutions/polymers/polyethylene.
Polyox, Colorcon, Application Data (Apr. 2009) downloaded from http://www.colorcon.com/literature/marketing/mr/Extended%20Release/POLYOX/English/ads_PEO_Antioxidant.pdf.
Pontier, C. et al, "Use of cycles of compression to characterize the behavior of apatitic phosphate powders," Journal of the European Ceramic Society 22 (2002), 1205-1216.

(56) References Cited

OTHER PUBLICATIONS

Porter, S. Coating of Pharmaceutical Dosage Forms. Chapter 91. pp. 1633-1643 in Remington's Pharmaceutical Sciences, 17th Ed, 1985.
Prapaitrakul W. et al, "Release of Chlorpheniramine Maleate from Fatty Acid Ester Matrix disks Prepared by Melt-extrusion" J. Pharm. Pharmacol. 43, pp. 377-381, 1991.
Proeschel, P.A. et al., "Task-dependence of activity / bite-force Relations and its impact on estimation of chewing force from EMG"; J. Dent. Res., vol. 81, No. 7, pp. 464-468, 2002.
Purdue News, "Purdue Pharma Provides Update on Development of New Abuse-Resistant Pain Medications; FDA Cites Patient Needs As First Priority; New Drug Application Delayed," www.headaches.about.com, Jun. 18, 2002, pp. 1-6.
Quintavalle et al., "Preparation of sustained release co-extrudates by hot-melt extrusion and mathematical modelling of in vitro/in vivo drug release profiles," European Journal of Pharmaceutical Sciences 33 (2008), 282-293.
Radko S.et al., Applied ad Theoretical Electrophoresis 5, pp. 79-88, 1995.
Ravin, L. Preformulation. Chapter 76, pp. 1409-1423, In Remington's Pharmaceutical Sciences 17th Ed, 1985.
Remington, The Science and Practice of Pharmacy, 19th ed., vol. II, p. 1457 (1995) (providing a table of DFA-approved commercially marketed salts).
Repka M. et al., Bioadhesive Properties of Hydroxypropylcellulose Topical Films Produced by Hot-Melt Extrusion, Journal of Controlled Release, 70 (2001), pp. 341-351.
Repka MA, Drug Day Ind Pharm, Oct. 2007; 33(10):1043. (Abstract).
Riippi M. et al., The effect of compression force on surface structure, crushing strength, friability and disintegration time of erythromycin acistrate tablets, Eur J Pharm Biopharm, vol. 46, 1998, pp. 339-345.
Rippie E.G. et al, "Regulation of Dissolution Rate by Pellet Geometry" Journal of Pharmaceutical Sciences, Vo. 58, No. 4, pp. 428-431, Apr. 1969.
Rippe, E. Powders. Chapter 89, pp. 1585-1602, In Remington's Pharmaceutical Sciences, 17th Ed, 1985.
Ritschel et al. Die Tablette: Handbuch der Entwicklung, Herstellung und Qualitatssicherung 2nd Edition, 2002, Ch 6, pp. 515-519. (Full English translation attached).
Ritschel et al. Die Tablette: Handbuch der Entwicklung, Herstellung und Qualitatssicherung, 2nd Edition, 2002, Ch 6, pp. 69-82 and 115-136.
Ritschel et al. Die Tablette: Handbuch der Entwicklung, Herstellung and Qualitatssicherung. 2nd Edition, 2002, Table of content.
Rosiaux et al. "Ethanol-resistant ethylcellulose/guar gum coatings—Importance for formulation parameters" European Journal of Pharmaceutics and Biopharmaceutics, vol. 85, No. 3, (Jul. 25, 2013). pp. 1250-1258.
Rowe C et al. Handbook of Pharmaceutical Excipients. Sixth Edition. 2009, Edition Cantor Verlag Aulendorf, pp. V-IX, Table of Contents.
Rowe C et al., Handbook of Pharmaceutical Excipients, 7th Edition, 2012, Table of Contents.
Salomies et al., "Determination of Oxycodone Hydrochloride in Oral Solutions by High-Performance Thin-Layer Chromatography/Densitometry," Journal of AOAC International, 83: 1497-1501 (2000).
Sax et al., Hawley's Condensed Chemical Dictionary, 11th ed., 1987, p. 1233, definition of "wax".
Scheirs J., et al. "Characterizing the Solid-State Thermal Oxidation of Poly (ethylene oxide) Powder", pp. 2014-2019. Polymer, vol. 32, No. 11, 1991.
Schier et al. "Fatality from Administration of Labetalol and Crushed Extended-Release Nifedipine" The Annals of Pharmacotherapy vol. 37, 1420-1423 Oct. 2003.
Schroeder J., et al. Granulierung hydrophober Wirkstoffe im Planetwalzenextruder, Pharm. Ind. 2003, vol. 65, No. 4, 367-372. (Full English translation attached).
Sciarra et al. Aerosols. Chapter 93., pp. 1662-1677, In Remington's Pharmaceutical Sciences, 17th Ed, 1985.
Search result conducted on http://www.unitconversion.org/force/newtons-to-kiloponds-convresion.html, on Jul. 5, 2011 (Conversion of 18.8 kiloponds to newtons).
Shivanand P et al., "Factors Affecting Release of KCl From Melt extruded Polyethylene Disks", Pharmaceutical Research, Oct. 1991, vol. 8, No. 10, p. S-192.
Siegel, P. Tonicity, Osmoticity, Osmolality, and Osmolarity. Chapter 80. pp. 1454-1472 In Remington's Pharmaceutical Sciences, 17th Ed, 1985.
Silver, J. "Painkiller OxyContin most commonly abused prescription drug on the streets of Western Pennsylvania", Pittsburg Post-Gazette, Apr. 8, 2001.
Spassov et al., Stereochemistry of Diastereomeric 3-Dialkylaminopropanols and O-Derivatives, J.f. prakt. Chemie, 323:5, 793-800 (1981).
Sprockel O.L et al. "Permeability of Cellulose Polymers: Water Vapour Transmission Rates" J. Pharma. Pharmacol. 42, pp. 152-157, 1990.
Sreenivasa, B. et al, Design and Evaluation of Ethylene Vinyl Acetate Sintered Matrix Tablets, Indian Journal of Pharmaceutical Sciences, Sep.-Oct. 2003, 65(5): 496-502.
Stafford J., Qberzogene feste Formen, 1991, 347-68. (English translation attached).
Strang, Abuse of buprenorphie (Terngesic) by snorting, Letter to the editor, British Med. J., 302: 969 (1991).
Stringer J.L., et al "Diffusion of small molecular weight drugs in radiation-crosslinkeci poly(ethylene oxide) hydrogels", Journal of Controlled Release 42, pp. 195-202, 1996.
Summers et al; "Influence of Crystal Form on Tensile Strength of Compacts of Pharmaceutical Materials" Journal of Pharmaceutical Sciences, vol. 66, No. 8, Aug. 1977, pp. 1172-1175.
Swarbrick, Encyclopedia of Pharmaceutical Technology, Informa Healthcare, 1988, 1st edition, vol. 1, table of contents.
Swarbrick, Encyclopedia of Pharmaceutical Technology, Informa Healthcare, 1988, 1st edition, vol. 10, table of contents.
Swarbrick, Encyclopedia of Pharmaceutical Technology, Informa Healthcare, 1988, 1st edition vol. 11, table of contents.
Swarbrick, Encyclopedia of Pharmaceutical Technology, Informa Healthcare, 1988, 1st edition, vol. 12, table of contents.
Swarbrick, Encyclopedia of Pharmaceutical Technology, Informa Healthcare, 1988, 1st edition, vol. 13, table of contents.
Swarbrick, Encyclopedia of Pharmaceutical Technology, Informa Healthcare, 1988, 1st dition, vol. 14, table of contents.
Swarbrick, Encyclopedia of Pharmaceutical Technology, Informa Healthcare, 1988, 1st edition, vol. 15, table of contents.
Swarbrick, Encyclopedia of Pharmaceutical Technology, Informa Healthcare, 1988, 1st edition, vol. 16, table of contents.
Swarbrick, Encyclopedia of Pharmaceutical Technology, Informa Healthcare, 1988, 1st edition, vol. 18, table of contents.
Swarbrick, Encyclopedia of Pharmaceutical Technology, Informa Healthcare, 1988, 1st edition, vol. 19, table of contents.
Swarbrick, Encyclopedia of Pharmaceutical Technology, Informa Healthcare, 1988, 1st edition, vol. 2, table of contents.
Swarbrick, Encyclopedia of Pharmaceutical Technology, lnforma Healthcare, 1988, 1st edition, vol. 20, table of contents.
Swarbrick, Encyclopedia of Pharmaceutical Technology, Informa Healthcare, 1988, 1st edition, vol. 3, table of contents.
Swarbrick, Encyclopedia of Pharmaceutical Technology, Informa Healthcare, 1988, 1st edition, vol. 4, table of contents.
Swarbrick, Encyclopedia of Pharmaceutical Technology, Informa Healthcare, 1988, 1st edition, vol. 5, table of contents.
Swarbrick, Encyclopedia of Pharmaceutical Technology, Informa Healthcare, 1988, 1st edition, vol. 6, table of contents.
Swarbrick, Encyclopedia of Pharmaceutical Technology, Informa Healthcare, 1988, 1st edition, vol. 7, table of contents.
Swarbrick, Encyclopedia of Pharmaceutical Technology, Informa Healthcare, 1988, 1st edition, vol. 8, table of contents.
Swarbrick, Encyclopedia of Pharmaceutical Technology, Informa Healthcare, 1988, 1st edition, vol. 9, table of contents.
Tablet, www.docstoc.com (2011).

(56) References Cited

OTHER PUBLICATIONS

Third Party Observations filed with EPO for Patent EP658055B1, Feb. 2, 2009, pp. 1-8.
Thoma V.K. et al. "Bestimmung der In-vitro-Freigabe von schwach basischen Wirkstoffen aus Ratardarzneiformen", pp. 299-301, Pharm. Ind. 51. Nr. 3, 1989.
Tikhonov, A. et al, Biopharmacy. The Manual for Student of Pharmaceutical Universities and Departments, 2003, pp. 40-41, Kharkov, Ukraine (Full English translation attached).
Tipler, et al, Physics for Scientists and Engineers, vol. I, 6th Edition, pp. 234-235, 2003.
Tompkins et al., "Human abuse liability assessment of oxycodone combined with ultra-low-dose natrexone," Psychopharma., 210: 471-480 (2010).
Tramadol Hydrochloride 100 mg Extended Release Tablets, Lubrizol Advanced Materials, Inc., Sep. 2010.
Tranquilan-Aranilla et al., "Kappa-carrageenan-polyethylene oxide hydrogel blends prepared by gamma irradiation," Radiation Physics and Chemistry vol. 55, pp. 127-131, 1999.
Turco et al. Intravenous Admixtures. Chapter 86. pp. 1542-1552, In Remington's Pharmaceutical Sciences, 17th Ed, 1985.
US Pharmacopoeia, Chapter 1217, Aug. 12, 2008.
Varma et al, Factors Affecting Mechanism and Kinetics of Drug Release from Matrix-Based Oral Controlled Drug. Delivery Systems, Am. J. Drug Deliv, 2004: 2 (1): 43-57.
Vippagunta et al. Advanced Drug Delivery Review 48 (2001), 3-26.
Wade and Weller, "Handbook of Pharmaceutical Excipients: 2nd Edition", The American Pharmaceutical Association and The Pharmaceutical Press, Washington and London, Table of Contents pp. v-vi, 1994.
Wagner, Pharmazeutische Biologie—Drogen und ihre Inhaltsstoffe—Scharfstoffdrogen, 2nd., revised edition, Gustav Fischer Verlag, Stuttgart-N.Y., 1982, pp. 82-92 (Full English Translation attached).
Wagner, Pharmazeutische Biologie—Drogen and ihre Inhaltsstoffe—Scharfstoffdrogen, 2nd., revised edition, Gustav Fischer Verlag, Stuttgart-N.Y., 1982, Table of Content.
Waltimo, et al, "A novel bite force recorder and maximal isometric bite force values for healthy young adults", Scandinavian Journal of Dental Research 1993; 101: 171-175.
Waltimo, et al, "Maximal bite force and its association with signs and symptoms of craniomandibular disorders in young Finnish non-patients", ACTA Odontol Scand 53 (1995): 254-258.
Waterman et al., "Stabilization of Pharmaceuticals to Oxidative Degradation", Pharmaceutical Development and Technology, vol. 7(1), pp. 1-32, (2002).
Waters et al., "Intravenous Quetiapine-Cocaine Use ("Q-Ball")", Letter to the Editor, Am. J. Psychiatry, 164(1) pp. 173-174 (2007).
Weiss, U., "Derivatives of Morphine. I 14-Dihydroxydihydromorphinone," J. Am. Chem. Soc. 77, pp. 5891-5892, Nov. 20, 1955.
Wikipedia-Dextromethorphan Aug. 12, 2013 (and attached related English-language entry dated Dec. 11, 2013).
Woodburn, K.R. et al., Vascular complications of injecting drug misuse, Br. J. of Surgery, vol. 83, 1996, pp. 1329-1334.
Wu N, et al. Mathematical modeling and in vitro study of controlled drug release via a highly swellable and dissoluble polymer matrix: polyethylene oxide with high molecular weights, J Control Release, Feb. 16, 2005;102(3):569-581.
Yang et al., "Zero-Order Release Kinetics from a Self-Correcting Floatable Asymmetric Configuration Drug Delivery System", Journal of Pharmaceutical Sciences, vol. 85, No. 2, Feb. 1996, pp. 170-173.
Yang, et al; "Characterization of Compressibility and Compactibility of Poly(ethylene oxide) Polymers for Modified Release Application by Compaction Simulator"; Journal of Pharmaceutical Sciences, vol. 85, No. 10, pp. 1085-1090, Oct. 1996.
Yarbrough et al, Letters to Nature "Extraordinary effects of mortar- and -pestle grinding on microstructure of sintered alumina gel", Nature 322, pp. 347-349 (Abstract only) (Jul. 24, 1986).

Yeh et al., Stability of Morphine in Aqueous Solution III: Kinetics of Morphine Degradation in Aqueous Solution, Wiley Subscription Services, Inc., Journal of Pharmaceutical Sciences, 50(1): 35-42 (1961).
Zeeshan, F and N. Bukhari, "Development and Evaluation of a Novel Modified-Release Pellet-Based Tablet System for the Delivery of Loratadine and Pseudophedrine Hydrochloride as Model Drugs," AAPS PharmaSciTech 11(2); 910-916 (available on-line May 22, 2010).
Zhang et al., "Properties of Sustained-Release Tablets Prepared by Hot-Melt Extrusion" Pharmaceutical Development and Technology, 1999, 4(2), 241-250.
Bingwen et al, 2008, p. 367.
Bruce et al, Properties of hot-melt extuded tablet formulations for the colonic delivery of 5-aminosalicylic acid, European Journal of Pharmaceutics and Biopharmaceutics, 59 (2005) 85-97.
Monolithic: retrieved from internet: http:/merriam-webster.com/dictionary/monolithic. Retrieved on Sep. 2, 2015.
Extended European Search Report and Opinion for Application No. EP 15165067.8-1455, dated Nov. 2, 2015.
Extended European Search Report and Opinion for Application No. EP 15165065.2-1455, dated Nov. 2, 2015.
Extended European Search Report and Opinion for Application No. EP 15165069.4-1455, dated Nov. 2, 2015
Extended European Search Report and Opinion for Application No. EP 15165064.5-1455, dated Oct. 16, 2015.
Extended European Search Report and Opinion for Application No. EP 15165070.2-1455, dated Nov. 2, 2015.
Cuesov, 1999, pp. 351-352.
Sidhu et al., "Watch for nonpsychotropics causing psychiatric side effects," Current Psychiatry, vol. 7, No. 4, 2008, 61-74.
Verhoeven et al., "Influence of polyethylene glycol/polyethylene oxide on the release characteristics of sustained-release ethylcellulose mini-matrices produced by hot-melt extrusion: in vitro and in vivo evaluations," European Journal of Pharmaceutics and Biopharmaceutics 72 (2009) 463-470.
Vynckier et al.,"Hot-melt co-extrusion for the production of fixed-dose combination products with a controlled release ethylcellulose matrix core," International Journal of Pharmaceutics 464 (2014), 65-74.
Extended European Search Report and Opinion for Application No. EP 15153679.4-1455, dated Jun. 30, 2015.
West, Anthony R., Solid state chemistry and its applications, Wiley, New York, 1988, pp. 358 and 365.
PCT International Search Report and Written Opinion for PCT Application No. PCT/EP2015/060377 dated Jul. 23, 2015.
PCT International Search Report and Written Opinion for PCT Application No. PCT/EP2015/061343 dated Jul. 21, 2015.
Bingwen et al, 2008, p. 367. (full translation attached).
Alekseeva et al, Chemical-Pharmaceutical Journal, vol. 41, No. 9, 2007, 49-52. (Full translation attached.).
Cuesov, Drug Production Technology, Khar'kov, 1999, pp. 351-352.
Borquist et al., "Simulation of the release from a multiparticulate system validated by single pellet and dose release experiements," J. Controlled Release, 97: 453-465 (2004).
Tennant, "Simultaneous Use of Stimulants and Opioids," 2011 [online] retrieved on Jul. 7, 2016 from: http://www.practicalpainmanagement.com/treatments/pharmacological/opioids/simultaneous-use-stimulants-opioids; 7 pages.
The Merck Index, 14th Ed. (2006) No. 0006360 Nalefene.
The Merck Index, 14th Ed. (2006) No. 0006362 Naloxone.
The Merck Index, 14th Ed. (2006) No. 0006363 Naltrexone.
The Merck Index, 14th Ed. (2006) No. 0006959 Oxycodone.
Efentakis et al, Effects of Excipients on Swellin and Drug Release from Compressed Matrices, in Drug Development and Industrial Pharmacy 23(1):107-112, Jan. 1997, Abstract.
Linz et al. "Cebranopadol: A Novel Potent Analgesic Nociception/Orphanin FQ Peptide and Opioid Receptor Agonist," J Pharmacol. Exp. Ther. 2014; 349: 535-548; available online Apr. 8, 2014.
Alekseeva et al, Chemical-Pharmaceutical Journal, vol. 41, No. 9, 2007, 49-52. (English abstract included.).

(56) References Cited

OTHER PUBLICATIONS

Saleem et al. "Formulation and Evaluation of Tramadol hydrochloride Rectal Suppositories," Indian J. Pharm Sci. Sep.-Oct. 2008; 70(5), 640-644.
Extended European Search Report and Opinion for Application No. EP 15184634.2-1455, dated Mar. 3, 2016.
Baxter, J.L. et al., "Hydrodynamics-induced variability in the USP apparatus II dissolution test," International Journal of Pharmaceutics 292 (2005) 17-28.
Bellmann et al., "Development of an advanced in vitro model of the stomach and its evaluation versus human gastric psychology." Food Research International 88 (2016) 191-198.
Extended European Search Report for Application No. EP 16183922.0-1460, dated Oct. 31, 2016.
Fathima, N. et al. "Drug-excipient interaction and its importance in dosage form development," Journal of Applied Pharmaceutical Science 01 (06); 2011, pp. 66-71.
Koziolek, M. et al., "Development of a bio-relevant dissolution test device simulating mechanical aspects present in the fed stomach," European Journal of Pharmaceutical Sciences 57 (2014) 250-256.
Meyer et al., "Awareness Topic: Mitigating the Risks of Ethanol Induced Dose Dumping from Oral Sustained/Controlled Release Dosage Forms," FDA ACPS Meeting, Oct. 2005, p. 1-4.
Remington, Chapter 45, pp. 996-1035. (Full Translation Attached).
Schilling, et al., "Novel application of hot-melt extrusion for the preparation of monolithic matrices containing enteric-coated particles." International Journal of Pharmaceutics 400 (2010) 34-31.
Starch 1500, Partially Pregelatinized Maize Starch, technical data from Colorcon, Feb. 2016, 6 pages.
Dabbagh, et al. "Release of Propranolol Hydrochloride from Matrix Tablets Containing Sodium Carboxymethylcellulose and Hydropropylmethylcellulose"; 1999; Pharmaceutical Development and Technology, 4(3), 313-324.
Extended European Search Report for Application No. EP 16182124.4-1455, dated Jan. 17, 2017.
M. Xu et al., "Evaluation of the coat quality of sustained release pellets by individual pellet dissolution methodology," Int. J. Pharm. 478 (2015) 318-327.
USP Expert Council, US Pharmacopoeia, Chapter 1092, 2007, 1-15.
COMPAP 90 technical data sheet Mar. 2014; 1 page.
U.S. Court of Appeals, Federal Circuit, *Purdue Pharma L.P.* v. *Epic Pharma, LLC*, 117 USPQ2D 1733 (Fed. Cir. 2016).
Decision of the United States District Court for the Southern District of New York, in *In re Endo Pharmaceuticals Inc. and Grünenthal GmbH* v. *Amneal Pharmaceuticals, LLC et al.*, Findings of Fact and Conclusions of Law, District Judge Thomas P. Griesa, New York, New York Jan. 14, 2015.
Decision of the United States District Court for the Southern District of New York, in *In re Oxycontin Antitrust Litigation, Purdue Pharma LP* v. *Teva Pharmaceuticals*, Findings of Fact and Conclusions of Law, District Judge Sidney H. Stein, New York, New York, Jan. 14, 2014.
Al-Angari, A. et al. "The compaction properties of polyethylene glycols," J Pharm. Pharmacol. (1985) 37:151-153.
Al-Nasassrah et al., "The effect of an increase in chain length on the mechanical properties of polyethylene glycols," European Journal of Pharmaceutics and Biopharmaceutics 46 (1998) 31-38.
Anderson, S.L. et al., "A Model for Antiplasticization in Polystyrene," Macromolecules 28:2944-54 (1995).
Back, D.M. et al., "Ethylene Oxide Polymers", in Kirk-Othmer Encyclopedia of Chemical Technology. 2000, John Wiley & Sons, Inc., vol. 10, 673-696.
Bailey, F.E., et al., "High Molecular Weight Polymers of Ethylene Oxide" Solution Properties Industrial and Engineering Chemistry, 1958. 50(1): 8-11.
Balogh, E., "Tastes in and Tastes of Paprika," in Taste: Proceedings of the Oxford Symposium on Food and Cookery 28 (Tom Jaine Ed.) 1988, pp. 25-40.

Baumann, T., "Pain Management," Pharmacotherapy: A Pathophysiologic Approach (J.T. DiPiro et al., eds., McGraw-Hill 4th ed. 1999), Ch. 56, 1014-1026.
Baumrucker, S.J., "OxyContin, the Media, and Law Enforcement", American Journal of Hospice & Palliative Care, 18:3 (May/Jun. 2001), 154-156.
Choi, S., et al., "Development of a Directly Compressible Poly(Ethylene Oxide for the Sustained-Release of Dihydrocodeine Bitartrate", Drug Development and Industrial Pharmacy, vol. 29, No. 10, pp. 1045-1052, 2003.
Choi, S., et al., "Hydrophilic Matrix Formulations of Dihydrocodeine Bitartrate with Polyethylene Oxide by Direct Compression," Proceedings of the $29^{th}$ Annual Meeting of the Controlled Release Society, in collaboration with the Korea Society for Biomaterials, Minneapolis, $1^{st}$ Edition, 2002, 984-985.
Ciccone, P. E., "Attempted Abuse of Concerta," Letters to the Editor, J. Am. Acad. Child Adolesc. Psychiatry, 41:7 (Jul. 2002).
Controversies in ADHD: A Breakfast Symposium—Concerta.
Crowley, M. et al., Pharmaceutical Applications of Hot-Melt Extrusion: Part I: Drug Dev. & Idus. Pharmacy (2007) 33:909-926.
Crowley, M. et al., "Properties of Hot-Melt Extruded CPM Tablets Using Hydrophilic Polymers," poster presentation, (2000).
Crowley, M., "Physicochemical and Mechanical Characterization of Hot-Melt Extruded Dosage Forms." Dissertation presented to the Faculty of the Graduate School of the University of Texas at Austin. (May 2003).
Crowley, M., et al., "Evaluation of a Hot Melt Extrusion Technique using a Hydrophilic Thermal Polymer and Retardant for the Preparation of Extended Release Chlorpheniramine Maleate Tablets," in American Association of Pharmaceutical Scientists: Indianapolis, IN (2000).
Crowley0000001—Crowley0000127.
Davies, N. Sustained Release and Enteric Coated NSAIDs: Are They Really GI Safe?J. Pharm. & Pharmaceut. Sci., 2(1):5-14, 1999.
Declaration of Dr. James W. McGinty, dated Oct. 28, 2009; online, retrieved from: http://www.accessdata.fda.gov/dmgsatfda_docs/labeV2013/021121s032lbl.pdf.
Dimitrov, M, et al., "Study of Verapamil hydrochloride release from compressed hydrophilic Polyox-Wsr tablets." Int'l Pharmaceutics (1999) 189:105-111.
Dittmer, D.K., et al., "Glue-Sniffing Neuropathies," Canadian Family Physician 39:1965-1971 (1993).
Donnelly, C.L., "ADHD Medications: Past and Future," Behavioral Health Management, May/Jun. 2002, 28 & 30.
Dow, "Material Safety Data Sheet: POLYOX(TM) WSR 30" (effective date: Sep. 18, 2001).
Dow, "POLYOX Water-Soluble Resins: Degradation of Water-Soluble Resins," Technical Data (Oct. 2002).
Drug Bank "Oxymorphone," 2015; online, available at: www.dmgbank.ca/chugs/db01192 printed Jul. 1, 2015.
*Endo Pharmaceutical Inc.* v. *Teva Pharmaceutical USA, Inc.* (S.D. N.Y 2015)—Redacted Version.
FDA News Release, "FDA approves abuse-deterrent labeling for reformulated OxyContin," Apr. 16, 2013, available at http://www.fda.gov/NewsEvents/Newsroom/Press.Announcements/ucm348252.htm.
FDA, "Notice of Determination the OxyContin Drug Products Covered by NDA 20-553 Were Withdrawn From Sale for Reasons of Safety or Effectiveness." Federal Register, vol. 78, No. 75, Apr. 18, 2013, 23273-23274.
Final Draft Labeling for Concerta Extended-Release Tablets Attachment to Approval Letter (2000); available at: http://www.accessdata.fda.gov/drugsatfda_docs/label.2000/21121lbl.pdf.
Greenhill, L.L., et al., "Practice Parameter for the Use of Stimulant Medications in the Treatment of Children, Adolescents, and Adults," J. Am. Acad. Child Adolesc. Psychiatry, 41:2 Supplement, 26S-49S (Feb. 2002).
Griffith, D., "Potential new ADHD drug creating lots of big hopes," Sacramento Bee (California), Oct. 30, 2002.
Huang, H. et al., "Preparation of Controlled Release Oral Dosage Forms by Low Temperature Melt Extrusion," AAPS PharmSci. 2000 2(S1).

(56) References Cited

OTHER PUBLICATIONS

Jaffe, S.L., "Failed Attempts at Intranasal Abuse of Concerta," Letters to the Editor, J. Am. Acad. Child Adolesc. Psychiatry, 41:1 (Jan. 2002).

Jannsen Pharmaeuticals, Inc. Concerta Labeling Revisioins, Dec. 12, 2013; online, retrieved from http://www.accessdata.fda.gov/dmgsatfda_docs/labeV2013/021121s032lbl.pdf.

Joint Claim Construction and Prehearing Statement, dated Jul. 11, 2014. *Janssen Pharmaceuticals, Inc. and Grünenthal GMBH v. Actavis Elizabeth LLC and Alkem Laboratories Limited*, Civil Action No. 2:13-cv-04507 CCC-MF (D.N.J.), *Janssen Pharmaceuticals, Inc. and Grünenthal GMBH v. Roxane Laboratories, Inc.*, Civil Action No. 2:13-cv-06929 CCC-MF (D.N.J.), and *Janssen Pharmaceuticals, Inc. and Grünenthal GMBH v. Alkem Laboratories Limited*, Civil Action No. 2:13-cv-07803 CCC-MF (D.N.J.).

Kibbe, Coloring Agents, in Handbook of Pharmaceuticals Excipients (3d ed. 2000).

Kidokoro, M. et al. ,"Properties of Tablets Containing Granulations of Ibuprofen and Acrylic Copolymers Prepared by Thermal Processes," Pharm Dev. and Tech. , 6:263-275 (2001).

Kinjo, N. et al, "Antiplasticization in the Slightly Plasticized Poly(vinyl chloride)," Polymer Journal 4(2):143-153 (1973).

Larhib, H. et al., "Compressing polyethyelene glycols: the effect of compression pressure and speed," Int'l J Pharmaceutics (1997) 147: 199-205.

Lieberman, H., et al., Pharmaceutical Dosage Forms: Tablets, vol. 2, Ch. 5: Granulation Technology and Tablet Characterization (1990), Table of contents and 245-348.

Lyons et al., "Twitch Interpolation in the Assessment of the Maximum Force-Generating Capacity of the Jaw-Closing Muscles in Man," Arch. Oral. Biol. 41:12, 1161-1168.

Makki, A, et. Al., Eds., A Dictionary of American Idioms, 4th Ed. Barron's, New York (2004), 342-343.

Markovitz, H., et al. "Calculations of Entanglement Coupling Spacings in Linear Polymers." Journal of Physical Chemistry, 1962. 66(8): 1567-1568.

McCrum, N., et al., Principles of Polymer Engineering. 2nd ed., New York: Oxford University Press. 447(1997), Chapter 7, 296-351.

McGinity, J.W. et al., "Melt-Extruded Controlled-Release Dosage Forms" in Pharmaceutical Extrusion Technology, Ghebre-Sellassie, I. and Martin, C., Eds., Marcel Dekker, Inc., New York, 2003, Chapter 10, 183-208.

McQuay, H. et a. "Methods of Therapeutic Trials," Textbook of Pain 1125-1138 (P.D. Wall & R. Melzack eds., Elsevier 4th ed. 1999), Table of Contents and 1125-1138.

Miura et al., "Comparison of Maximum Bite Force and Dentate Status Between Healthy and Frail Elderly Persons," J. Oral Rehabilitation, vol. 28 (2001), pp. 592-595.

Miyagawa, Y. et al., "Controlled-release of diclofenac sodium from wax matrix granulate," Int'l J. Pharmaceutics (1996) 138:215-224.

National Drug Intelligence Center Information Bulletin "OxyContin Diversion and Abuse" Jan. 2001.

Payne, H. et al., Denatonium Benzoate as a Bitter Aversive Additive in Ethylene Glycol and Methanol-Based Automotive Products, SAE Technical Paper 930589, Abstract (1993).

Pilpel, N., et al. "The effect of temperature on the tensile strength and disintegration of paracetamol and oxytetracylcine tablets," J Pharm Pharmac., 29:389-392 (1977).

POLYOX Water-Soluble Resins NF in Pharmaceutical Applications, Dow Chemical Company, Aug. 2002.

Purdue Pharma LP Materials Safety Data Sheet, OxyContin Tablets, 10mg, 15 mg, 20 mg, 30 mg, 40 mg, 60 mg, Version 16—Sep. 10; available at www.purduephruma.com/msdss/oxycontin_msds.pdf.

Rauwendaal, Chris, PHD, Responsive Expert Report of Chris Rauwendaal, Ph.D. Regarding Expert Report of Michael M. Crowley, Ph.D., dated Jul. 17, 2015.

Repka, M. et al. Pharmaceutical Applications of Hot-Melt Extrusion: Part II. Drug Dev. & Indus. Pharmacy (2007) 33:1043-1057.

Saravanan, M. et al., "The Effect of Tablet Formulation and Hardness on in Vitro Release of Cephalexin from Eudragit L100 Based Extended Release Tablets," Biol. Pharm. Bull. (2002) 25(4):541-545.

Seitz, J.A.; et al., "Evaluation of the Physical Properties of Compressed Tablets 1: Tablet Hardness and Friability," J. of Pharm. Sci. , 54:1353-1357 (1965).

Shah, et al., "Some Effects of Humidity and Heat on the Tableting Properties of Microcrystalline Cellulose Formulations 1," J. of Pharm. Sci., 57:181-182 (1967).

Singhal, et al., Handbook of Indices of Food Quality and Authenticity (1997), "Capsicum" p. 398-299.

Smith, K.L. et al. "High Molecular Weight Polymers of Ethylene Oxide—Plastic Properties." Industrial and Engineering Chemistry, 1958. 50(1): 12-16.

Tapentadol Pre-Review Report, Expert Committee on Drug Dependency Thirty-Fifth Meeting Hammamet, Tunisia, Jun. 4-8, 2012, available at http://www.who.int/medicines/areas/quality_safety/5.2Tapentadolpre-review.pdf.

Tiwari, D., et al., "Evaluation of polyoxyethylene homopolymers for buccal bioadhesive drug delivery device formulations." AAPS Pharmsci, 1999. 1(3): Article 13.

Wilkins, J.N., "Pharmacotherapy of Schizophrenia Patients with Comorbid Sunstance Abuse," Schizophrenia Bulletin, 23:215-228 (1997).

World Health Org., Cancer Pain Relief With a Guide to Opioid Availability (2d ed. 1996).

Yin, T.P., et al., "Viscoelastic Properties of Polyethylene Oxide in Rubber-Like State." Journal of Physical Chemistry, 1961. 65(3): 534-538.

Zacny, J. et al. Drug & Alcohol Dependence (2003) 69:215-232.

Zhang, F., "Hot-Melt Extrusion as a Novel Technology to Prepare Sustained-Release Dosage Forms," Dissertation University of Texas at Austin, Dec. 1999.

\* cited by examiner

MULTIPARTICLES SAFEGUARDED AGAINST ETHANOLIC DOSE-DUMPING

FIELD OF THE INVENTION

This application claims priority of European Patent Application No. 14 169 801.9, filed on May 26, 2014, the entire content of which is incorporated herein by reference.

The invention relates to an oral pharmaceutical dosage form providing resistance against dose dumping in aqueous ethanol and comprising a pharmacologically active ingredient, preferably an opioid, embedded in a matrix material,
  wherein the matrix material comprises an alkyl cellulose, preferably ethyl cellulose, and a heteropolysaccharide, preferably xanthan gum; and
  wherein the relative weight ratio of heteropolysaccharide to alkyl cellulose is within the range of from 1:20 to 20:1; and
  wherein the total content of alkyl cellulose and heteropolysaccharide is at least 35 wt.-%, relative to the total weight of the dosage form; and
  wherein preferably the content of the alkyl cellulose is at least 10 wt.-%, relative to the total weight of the dosage form; and/or
  wherein preferably the content of the alkyl cellulose in the dosage form is higher than the content of the heteropolysaccharide in the dosage form.

BACKGROUND OF THE INVENTION

A large number of pharmacologically active substances have a potential for being intentionally or unintentionally abused or misused, i.e. they can be used to produce effects which are not consistent with their intended use. Thus, e.g. opioids which exhibit an excellent efficacy in controlling severe to extremely severe pain are frequently abused to induce euphoric states similar to being intoxicated. In particular, active substances which have a psychotropic effect are abused accordingly.

To intentionally enable abuse, the corresponding pharmaceutical dosage forms, such as pharmaceutical dosage forms or capsules can be taken with alcohol (oral abuse). Alternatively, the dosage forms are crushed, for example ground by the abuser, the active substance is extracted from the thus obtained powder using a preferably aqueous liquid and after being optionally filtered through cotton wool or cellulose wadding, the resultant solution is administered parenterally, in particular intravenously. This type of dosage results in an even faster diffusion of the active substance compared to the oral abuse, with the result desired by the abuser, namely the kick. This kick or these intoxication-like, euphoric states are also reached if the powdered pharmaceutical dosage form is administered nasally, i.e. is sniffed.

However, sometimes patients unintentionally disrupt the controlled release properties of dosage forms by concomitant consumption of alcoholic beverages, thereby inducing dose dumping. Dosage forms containing active ingredients having a high solubility in water usually have a high susceptibility to ethanolic dose dumping.

Various concepts for the avoidance of intentional and unintentional drug abuse have been developed.

It has been proposed to incorporate in pharmaceutical dosage forms aversive agents and/or antagonists in a manner so that they only produce their aversive and/or antagonizing effects when the pharmaceutical dosage forms are tampered with. However, the presence of such aversive agents is principally not desirable and there is a need to provide sufficient tamper-resistance without relying on aversive agents and/or antagonists.

Another concept to prevent abuse relies on the mechanical properties of the pharmaceutical dosage forms, particularly an increased breaking strength (resistance to crushing). The major advantage of such pharmaceutical dosage forms is that comminuting, particularly pulverization, by conventional means, such as grinding in a mortar or fracturing by means of a hammer, is impossible or at least substantially impeded. Thus, the pulverization, necessary for abuse, of the pharmaceutical dosage forms by the means usually available to a potential abuser is prevented or at least complicated. Such pharmaceutical dosage forms are useful for avoiding drug abuse of the pharmacologically active ingredient contained therein, as they may not be powdered by conventional means and thus, cannot be administered in powdered form, e.g. nasally. The mechanical properties, particularly the high breaking strength of these pharmaceutical dosage forms renders them tamper-resistant. In the context of such tamper-resistant pharmaceutical dosage forms it can be referred to, e.g., WO 2005/016313, WO 2005/016314, WO 2005/063214, WO 2005/102286, WO 2006/002883, WO 2006/002884, WO 2006/002886, WO 2006/082097, WO 2006/082099, and WO2009/092601.

However, besides tampering of pharmaceutical dosage forms in order to abuse the drugs contained therein, the potential impact of concomitant intake of ethanol on the in vivo release of drugs from modified release oral formulations (dose-dumping) has recently become an increasing concern. Controlled or modified release formulations typically contain a higher amount of the pharmacologically active ingredient relative to its immediate release counterpart. If the controlled release portion of the formulation is easily defeated, the end result is a potential increase in exposure to the active drug and possible safety concerns. In order to improve safety and circumvent intentional tampering (e.g. dissolving a controlled release pharmaceutical dosage form in ethanol to extract the drug), a reduction in the dissolution of the modified release fractions of such formulations, in ethanol, may be of benefit.

For monolithic dosage forms some formulation concepts are known which provide to some degree a controlled release of the drug substance even in ethanolic media. Further, however, monolithic dosage forms are not suitable for all patient groups, as they are required to be swallowed intact. Due to the big size of such formulations this is not possible for patients having difficulties in swallowing as e.g. the elderly and children. These patients have a high risk of choking on monolithic dosage forms. Pulverization of these dosage forms on the other hand solves the choking hazard, but endangers the patients by releasing a potentially toxic dose of the drug substance.

The swallowing issue can be overcome by the use of multiparticulate dosage forms, e.g. MUPS (multiple unit pellet system) tablets or capsules filled with controlled release granules, which can be reduced in size to the size of the individual particles without losing the control of the drug release. In contrast to the above mentioned monolithic formulations, obtaining functional robustness in ethanolic media of the multiparticulate formulations is a challenge. Working examples of monolithic dosage forms contain hydrophilic polymer matrices, wherein control of drug release is achieved by a long diffusion way within the formulation. For multiparticulate forms, long diffusion ways do not exist due to the small size of the individual particles. A common technique to overcome this problem is the application of a functional barrier coating on top of the individual particle, e.g. ethylcellulose for diffusion control. However, as ethylcellulose is alcohol soluble, these formulation approaches are not resistant against ethanolic dose dumping.

Accordingly, the need exists to develop new formulations having reduced potential for dose dumping in alcohol.

US 2008/0085304 discloses robust sustained release formulations, solid dosage forms comprising robust sustained release formulations, and methods for making and using these formulations and solid dosage forms are provided. Robustness of the sustained release formulation is related to the particle size of the hydrophilic gum. Sustained release formulations resist dose-dumping when ingested with alcohol. The formulations are useful for treating a patient suffering from a condition, e.g., pain. The formulations comprise at least one drug. In one embodiment, the drug is an opioid, e.g., oxymorphone.

WO 2009/034541 relates to a solid dosage form for the controlled release of trimetazidine suitable for once-daily dosing, in which the dosage form exhibits a controlled in vitro release of trimetazidine in phosphate buffer at pH 6.8 of not less than about 75% after 16 hours when measured using USP Apparatus I at 100 rpm, thereby decreasing the incidence and severity of burst release or dose dumping.

WO 2013/084059 relates to a pharmaceutical dosage form comprising a mixture in the form of an extended release matrix formulation, the mixture comprising at least: (1) at least one poly($\epsilon$-caprolactone), and (2) at least one polyethylene oxide, and (3) at least one active agent. The dosage form is said to be tamper resistant and to provide extended release of the active agent. However, poly($\epsilon$-caprolactone) is not a pharmacopeial excipient for oral use according to the Ph. Eur. and the USP, respectively.

WO 2012/166474 relates to a solid dose form comprising a film coating composition encapsulating a core, wherein the core comprises an active ingredient comprising at least one of a pharmaceutical, veterinary, or nutraceutical active ingredient; the film coating composition comprises ethylcellulose and guar gum; and the guar gum is present in an amount greater than 5 wt % based on the weight of the guar gum and ethylcellulose. The solid dose form is said to provide controlled release of the active ingredient and to be ethanol resistant. Extended release tablets comprising a lipid matrix containing glyceryl (di)behenate (commercially available as Compritol® 888 ATO) in which the active ingredient is embedded are said to not being susceptible to alcohol-related dose dumping. The drug substance is said to be released from the dosage form by diffusion, thereby leaving behind an in principle structurally intact tablet matrix. However, this is not satisfactory in every respect. The remaining "washed-out" lipid tablet will remain visible in human stool after excretion. This observation ("ghosting") is known to lead to increased complaints by patients and a reduced patient compliance. Further, mechanical manipulation of the tablet e.g. dividing it to allow easier swallowing, leads to an accelerated drug release due to reduced diffusion ways eventually resulting in higher plasma concentrations of the drug substance including toxic levels.

However, the properties of these pharmaceutical dosage forms of the prior art, however, are not satisfactory in every respect.

SUMMARY OF THE INVENTION

It is an object of the invention to provide dose-dumping resistant pharmaceutical dosage forms containing a pharmacologically active ingredient, preferably an opioid, which have advantages compared to the dosage forms of the prior art.

This object has been achieved by the subject matter described hereinbelow and in the appended patent claims when issued.

A first aspect of the invention relates to an oral pharmaceutical dosage form providing resistance against dose dumping in aqueous ethanol and comprising a pharmacologically active ingredient, preferably an opioid, embedded in a matrix material, wherein the matrix material comprises an alkyl cellulose, preferably ethyl cellulose, and a heteropolysaccharide, preferably xanthan gum; and wherein the relative weight ratio of heteropolysaccharide to alkyl cellulose is within the range of from 1:20 to 20:1; and wherein the total content of alkyl cellulose and heteropolysaccharide is at least 35 wt.-%, relative to the total weight of the dosage form; and wherein preferably the content of the alkyl cellulose is at least 10 wt.-%, relative to the total weight of the dosage form; and/or wherein preferably the content of the alkyl cellulose in the dosage form is higher than the content of the heteropolysaccharide in the dosage form.

It has been surprisingly found that an oral pharmaceutical dosage form comprising a pharmacologically active ingredient, preferably an opioid, an alkyl cellulose and a heteropolysaccharide can be prepared, wherein the dosage form exhibits tamper resistance, especially in terms of resistance against dose-dumping of the pharmacologically active ingredient in aqueous ethanol.

Further, it has been surprisingly found that the content of the pharmacologically active ingredient, preferably the opioid in the dosage form and in the particles, respectively, can be optimized in order to provide the best compromise between tamper-resistance, disintegration time and drug release, drug load, processability (especially pharmaceutical dosage formability) and patient compliance.

Still further, it has been surprisingly found that the dosage forms provide a retarded release when the release medium additionally contains ethanol compared to the release in aqueous medium not containing ethanol. This result was completely unexpected because of the good solubility of alkyl celluloses, especially ethylcellulose in ethanol.

BRIEF DESCRIPTION OF THE DRAWINGS

The invention will now be described in greater detail with reference to the drawings, wherein.

DETAILED DESCRIPTION OF THE INVENTION

Figure 1:
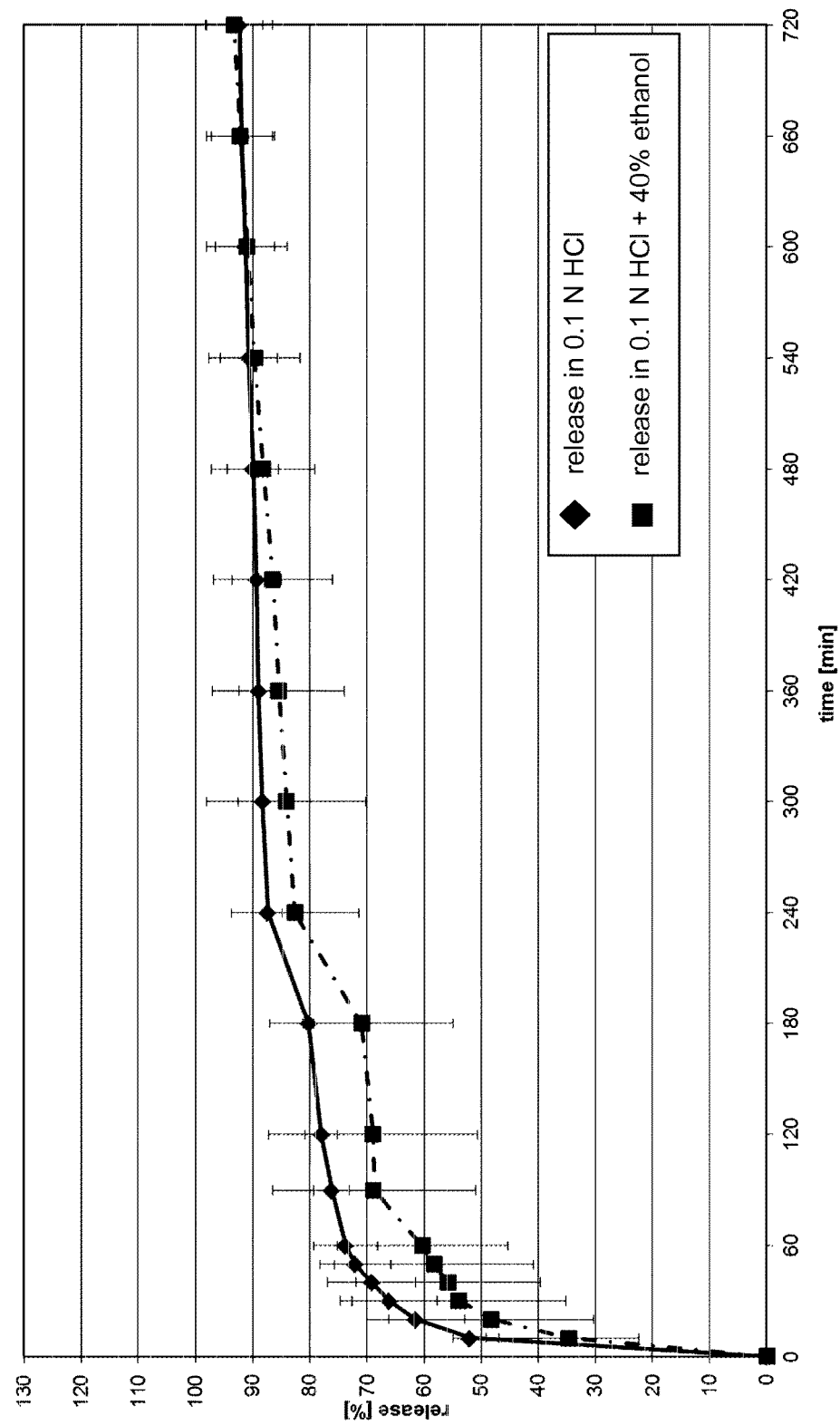
FIG. 1 shows the release profile of the capsules of Example 1 in 0.1 N HCl and in a mixture of 0.1 N HCl and 40% ethanol, respectively.

Unless expressly stated otherwise, all percentages are by weight (wt.-%).

As used herein, the term "pharmaceutical dosage form" and "dosage form", respectively, refers to a pharmaceutical entity that comprises a pharmacologically active ingredient, preferably an opioid, and which is actually administered to, or taken by, a patient. It may be compressed or molded in its manufacture, and it may be of almost any size, shape, weight, and color.

The dosage form is preferably solid or semisolid.

Examples of dosage forms according to the invention include, but are not limited to, tablets, capsules, pills, granules, pellets, sachets and effervescent, powders, and the like. In a preferred embodiment, the dosage form is a filled capsule or a tablet. According to this embodiment, the capsule can be a hard or soft gelatin capsule.

Most pharmaceutical dosage forms are intended to be swallowed whole and accordingly, the dosage forms according to the invention are designed for oral administration.

In a preferred embodiment, the dosage form according to the invention is particulate. According to this embodiment, the dosage form is preferably comprises a multitude of particles or granules. An advantage of particulate dosage forms is that the particles may be mixed in different amounts to thereby produce dosage forms of different strengths.

In another preferred embodiment, the dosage form according to the invention can be regarded as a MUPS formulation (multiple unit pellet system). Preferably, the dosage form according to the invention contains all ingredients in a dense compact unit which in comparison to capsules has a comparatively high density. Under these circumstances, the dosage forms according to the invention preferably comprise subunits having different morphology and properties, namely drug-containing particles and an outer matrix material, wherein the particles form a discontinuous phase within the outer matrix material. The constituents of the outer matrix material are preferably different from the constituents of the drug-containing particles. Preferably, the outer matrix material neither contains a pharmacologically active ingredient nor an alkyl cellulose nor a heteropolysaccharide.

The particles typically have mechanical properties that differ from the mechanical properties of the outer matrix material. The particles can preferably be visualized by conventional means such as solid state nuclear magnetic resonance spectroscopy, raster electron microscopy, terahertz spectroscopy and the like.

In still another preferred embodiment, the dosage form according to the invention is monolithic. In this regard, monolithic preferably means that the dosage form is formed or composed of material without joints or seams or consists of or constitutes a single unit.

The dosage form according to the invention has preferably a total weight in the range of 0.01 to 1.5 g, more preferably in the range of 0.05 to 1.2 g, still more preferably in the range of 0.1 g to 1.0 g, yet more preferably in the range of 0.2 g to 0.9 g, and most preferably in the range of 0.3 g to 0.8 g. In a preferred embodiment, the total weight of the dosage form is within the range of 350±300 mg, more preferably 350±250 mg, still more preferably 350±200 mg, yet more preferably 350±150 mg, most preferably 350±100 mg, and in particular 350±50 mg. In another preferred embodiment, the total weight of the dosage form is within the range of 500±450 mg, more preferably 500±300 mg, still more preferably 500±200 mg, yet more preferably 500±150 mg, most preferably 500±100 mg, and in particular 500±50 mg. In still another preferred embodiment, the total weight of the dosage form is within the range of 600±450 mg, more preferably 600±300 mg, still more preferably 600±200 mg, yet more preferably 600±150 mg, most preferably 600±100 mg, and in particular 600±50 mg.

In a preferred embodiment, the dosage form according to the invention is a filled capsule. Dosage forms of this embodiment preferably have a lengthwise extension (longitudinal extension) of about 4 mm to about 30 mm, more preferably about 6 mm to about 25 mm, most preferably about 8 mm to about 23 mm, and in particular about 10 mm to about 20 mm; and an internal diameter in the range of about 1 mm to about 20 mm, more preferably about 3 mm to about 17 mm, most preferably about 5 mm to about 15 mm, an in particular about 7 mm to about 13 mm.

In another preferred embodiment, the dosage form according to the invention is a round dosage form. Dosage forms of this embodiment preferably have a diameter in the range of about 1 mm to about 30 mm, more preferably about 2 mm to about 25 mm, most preferably about 5 mm to about 23 mm, and in particular about 7 mm to about 13 mm; and a thickness in the range of about 1.0 mm to about 12 mm, more preferably about 2.0 mm to about 10 mm, most preferably about 3.0 mm to about 9.0 mm, and in particular about 4.0 mm to about 8.0 mm.

In still another preferred embodiment, the dosage form according to the invention is an oblong dosage form. Dosage forms of this embodiment preferably have a lengthwise extension (longitudinal extension) of about 1 mm to about 30 mm, more preferably about 2 mm to about 25 mm, most preferably about 5 mm to about 23 mm, and in particular about 7 mm to about 20 mm; a width in the range of about 1 mm to about 30 mm, more preferably about 2 mm to about 25 mm, most preferably about 5 mm to about 23 mm, and in particular about 7 mm to about 13 mm; and a thickness in the range of about 1.0 mm to about 12 mm, more preferably about 2.0 mm to about 10 mm, most preferably about 3.0 mm to about 9.0 mm, and in particular about 4.0 mm to about 8.0 mm.

When the dosage form according to the invention is monolithic, it preferably has an extension in any direction of at least 2.0 mm, more preferably at least 2.5 mm, still more preferably at least 3.0 mm, yet more preferably at least 3.5 mm, even more preferably at least 4.0 mm, most preferably at least 4.5 mm and in particular at least 5.0 mm.

The dosage form or the particles if the dosage form is in a particulate form may optionally comprise a coating, e.g. a cosmetic coating. The coating is preferably applied after formation of the pharmaceutical dosage form. The coating may be applied prior to or after the curing process.

In a preferred embodiment, if the dosage form and the particles, respectively, is/are coated, said coating does not provide any resistance against dose dumping in aqueous ethanol. According to this embodiment, an alkyl cellulose such as ethyl cellulose and/or a heteropolysaccharide such as xanthan gum or guar gum, are preferably not contained in a coating which may be applied to the dosage form and the particles, respectively.

In a preferred embodiment, the dosage form is not coated and/or when the dosage form is particulate, the particles are not coated.

Preferably, the dosage forms according to the invention are film coated with conventional film coating compositions. Suitable coating materials are commercially available, e.g. under the trademarks Opadry® and Eudragit®.

Examples of suitable materials include cellulose esters and cellulose ethers, such as methylcellulose (MC), hydroxypropylmethylcellulose (HPMC), hydroxypropylcellulose (HPC), hydroxyethylcellulose (HEC), sodium carboxymethylcellulose (Na-CMC), poly(meth)acrylates, such as aminoalkylmethacrylate copolymers, methacrylic acid methylmethacrylate copolymers, methacrylic acid methylmethacrylate copolymers; vinyl polymers, such as polyvinylpyrrolidone, polyvinyl alcohol, polyvinylacetate; and natural film formers.

The coating can be resistant to gastric juices and dissolve as a function of the pH value of the release environment. By means of this coating, it is possible to ensure that the dosage form according to the invention passes through the stomach undissolved and the active compound is only released in the intestines. The coating which is resistant to gastric juices preferably dissolves at a pH value of between 5 and 7.5.

The coating can also be applied e.g. to improve the aesthetic impression and/or the taste of the dosage forms and the ease with which they can be swallowed. Coating the dosage forms according to the invention can also serve other purposes, e.g. improving stability and shelf-life. Suitable coating formulations comprise a film forming polymer such as, for example, polyvinyl alcohol or hydroxypropyl methylcellulose, e.g. hypromellose, a plasticizer such as, for example, a glycol, e.g. propylene glycol or polyethylene glycol, an opacifier, such as, for example, titanium dioxide, and a film smoothener, such as, for example, talc. Suitable coating solvents are water as well as organic solvents. Examples of organic solvents are alcohols, e.g. ethanol or isopropanol, ketones, e.g. acetone, or halogenated hydrocarbons, e.g. methylene chloride. Coated pharmaceutical dosage forms according to the invention are preferably prepared by first making the cores and subsequently coating said cores using conventional techniques, such as coating in a coating pan.

For the purpose of specification, the term "particle" refers to a discrete mass of material that is solid, e.g. at 20° C. or at room temperature or ambient temperature. Preferably a particle is solid at 20° C. Preferably, the particles are monoliths. Preferably, the pharmacologically active ingredient, which is preferably an opioid, the alkyl cellulose, which is preferably ethyl cellulose, and the heteropolysaccharide, which is preferably xanthan gum, are intimately homogeneously distributed in the particles so that the particles do not contain any segments where either pharmacologically active ingredient is present in the absence of the alkyl cellulose and/or the heteropolysaccharide or the alkyl cellulose is present in the absence of the pharmacologically active ingredient and/or the heteropolysaccharide or the heteropolysaccharide is present in the absence of the pharmacologically active ingredient and/or the alkyl cellulose.

When the dosage form is particulate, it preferably comprises a multitude i.e. plurality of particles containing pharmacologically active ingredient (drug-containing particles) and may optionally further comprise particles not containing any pharmacologically active ingredient (drug-free particles). Preferably, if the dosage form is particulate, all particles are drug-containing particles. Preferably, the particles are not film coated.

In a preferred embodiment, the dosage form preferably comprises at least 2, more preferably at least 4, still more preferably at least 6, yet more preferably at least 8, even more preferably at least 10, most preferably at least 15 and in particular at least 20 or at least 100 or at least 1000 drug-containing particles. In another preferred embodiment, the dosage form preferably comprises at most 10, more preferably at most 9, still more preferably at most 8, yet more preferably at most 7, even more preferably at most 6, most preferably at most 5, and in particular at most 4 or 3 or 2 drug-containing particles.

The particles are preferably of macroscopic size, typically the average diameter is within the range of from 100 µm to 5,000 µm, preferably 200 µm to 4,000 µm, more preferably 300 µm to 3,000 µm, still more preferably 400 µm to 2,000 µm, most preferably 500 µm to 1,500 µm, and in particular 500 µm to 1,000 µm. Preferably, the particles in the dosage form have an average particle size of at least 50 µm, more preferably at least 100 µm, still more preferably at least 150 µm or at least 200 µm, yet more preferably at least 250 µm or at least 300 µm, most preferably at least 400 µm or at least 500 µm, and in particular at least 550 µm or at least 600 µm. Preferably, the particles in the dosage form have an average particle size of at least 700 µm, more preferably at least 800 µm and most preferably at least 900 µm.

In a preferred embodiment, the dosage forms according to the invention comprise particles as a discontinuous phase, i.e. the particles form a discontinuous phase in an outer matrix material which in turn preferably forms a continuous phase. In this regard, discontinuous means that not each and every particle is in intimate contact with another particle but that the particles are at least partially separated from one another by the outer matrix material in which the particles are embedded. In other words, the particles preferably do not form a single coherent mass within the dosage forms according to the invention.

Preferably, when the dosage form according to the invention is particulate, the dosage form does not contain an outer matrix material. According to this embodiment, the dosage form preferably is a filled capsule.

Preferably, when the dosage form is particulate, the content of the particles in the dosage forms according to the invention is at most 95 wt.-%, more preferably at most 90 wt.-%, still more preferably at most 85 wt.-%, yet more preferably at most 80 wt.-%, most preferably at most 75 wt.-% and in particular at most 70 wt.-%, based on the total weight of the dosage forms.

Preferably, when the dosage form is particulate, the content of the particles in the dosage forms according to the invention is at least 10 wt.-%, at least 15 wt.-%, at least 20 wt.-% or at least 25 wt.-%; more preferably at least 30 wt.-%, at least 35 wt.-%, at least 40 wt.-% or at least 45 wt.-%; most preferably at least 50 wt.-%, at least 55 wt.-%, at least 60 wt.-% or at least 65 wt.-%; and in particular at least 70 wt.-%, at least 75 wt.-%, at least 80 wt.-% or at least 85 wt.-%; based on the total weight of the dosage form.

When the dosage form is particulate, the shape of the particles is not particularly limited.

In a preferred embodiment, the particles are manufactured by granulation, preferably wet, dry or fluid bed granulation. According to this embodiment, the particles preferably have an irregular shape. When the particles have been prepared by granulation, they preferably have a particle size in the range of from 300 µm to 5 mm, more preferably 400µ to 4 mm, still more preferably 500 µm to 3 mm, yet more preferably 600 µm to 2 mm, most preferably 700µ to 1.5 mm and in particular 850 µm to 1.25 mm. When the dosage form according to the invention is particulate and when the particles are manufactured by granulation, preferably the dosage form is a filled capsule.

In another preferred embodiment, the particles are manufactured by hot-melt extrusion. According to this embodiment, the particles preferably are generally cylindrical in shape. The diameter of such particles is therefore the diameter of their circular cross section. The cylindrical shape is caused by the extrusion process according to which the diameter of the circular cross section is a function of the extrusion die and the length of the cylinders is a function of the cutting length according to which the extruded strand of material is cut into pieces of preferably more or less predetermined length.

Preferred particles manufactured by hot-melt extrusion have an average length and average diameter of about 1,000 µm or less. When the particles are manufactured by extrusion technology, the "length" of particles is the dimension of the particles that is parallel to the direction of extrusion. The minimum average length of the particles is determined by the cutting step and may be, e.g. 4.0 mm, 3.0 mm, 2.0 mm, 2.5 mm, 2.0 mm, 1.5 mm, 1.0 mm, 0.9 mm, 0.8 mm, 0.7 mm, 0.6 mm, 0.5 mm, 0.4 mm, 0.3 mm or 0.2 mm.

The "diameter" of particles is the largest dimension that is perpendicular to the direction of extrusion. When the particles have been manufactured by hot-melt extrusion, they preferably have an average diameter in the range of 200 to 1500 µm, more preferably 400 to 800 µm, still more preferably 450 to 700 µm, yet more preferably 500 to 650 µm, e.g. about 500 to 600 µm. Preferably, when the particles have been manufactured by hot-melt extrusion, they have an average length in the range of 500 to 5000 µm, more preferably 750 to 4600 µm, still more preferably 1000 to 4200 µm, yet more preferably 1250 to 3800 µm, even more preferably 1500 to 3400 µm, most preferably 1750 to 3200 µm and in particular 2000 to 3000 µm. In another preferred embodiment, particles manufactured by hot-melt extrusion have an average length in the range of 200 to 1000 µm, more preferably 400 to 800 µm, still more preferably 450 to 700 µm, yet more preferably 500 to 650 µm, e.g. about 500 to 600 µm.

The size of particles may be determined by any conventional procedure known in the art, e.g. laser light scattering, sieve analysis, light microscopy or image analysis.

Preferably, when the dosage form is particulate, the plurality of particles that is contained in the dosage form according to the invention has an arithmetic average weight, in the following referred to as "aaw", wherein at least 70%, more preferably at least 75%, still more preferably at least 80%, yet more preferably at least 85%, most preferably at least 90% and in particular at least 95% of the individual particles contained in said plurality of particles has an individual weight within the range of aaw±30%, more preferably aaw±25%, still more preferably aaw±20%, yet more preferably aaw±15%, most preferably aaw±10%, and in particular aaw±5%. For example, if the dosage form according to the invention contains a plurality of 100 particles and aaw of said plurality of particles is 1.00 mg, at least 75 individual particles (i.e. 75%) have an individual weight within the range of from 0.70 to 1.30 mg (1.00 mg±30%).

In a preferred embodiment, the particles, more preferably the drug-containing particles, each have a weight of less than 20 mg, more preferably less than 18 mg, still more preferably less than 16 mg, yet more preferably less than 14 mg, even more preferably less than 12 mg or less than 10 mg, most preferably less than 8 mg, and in particular less than 6 or 4 mg. According to this embodiment, all individual particles each preferably have a weight of from 1 to 19 mg, more preferably 1.5 to 15 mg, still more preferably 2.0 to 12 mg, yet more preferably 2.2 to 10 mg, even more preferably 2.5 to 8 mg, most preferably 2.8 to 6 mg and in particular 3 to 5 mg.

In another preferred embodiment, the particles, more preferably the drug-containing particles, each have a weight of 20 mg or more. According to this embodiment, all individual particles preferably each have a weight of at least 30 mg, more preferably at least 40 mg, still more preferably at least 50 mg, most preferably at least 60 mg and in particular at least 100 mg. Preferably, all individual particles each have a weight of from 20 to 1000 mg, more preferably 30 to 800 mg, still more preferably 40 to 600 mg, yet more preferably 50 to 400 mg, even more preferably 60 to 200 mg, most preferably 70 to 150 mg and in particular 80 to 120 mg. According to this embodiment, the particles of the dosage form, more preferably the drug-containing particles of the dosage form, preferably each have an extension in any given direction of at least 2.0 mm or 3.0 mm and have a weight of at least 20 mg.

When the dosage form is particulate, the particles may be e.g. loosely contained in a capsule, or the particles may be incorporated into an outer matrix material. From a macroscopic perspective, the outer matrix material preferably forms a continuous phase in which the particles are embedded as discontinuous phase.

Preferably, the outer matrix material is preferably a homogenous coherent mass, preferably a homogeneous mixture of solid constituents, in which the particles are embedded thereby spatially separating the particles from one another. While it is possible that the surfaces of particles are in contact or at least in very close proximity with one another, the plurality of particles preferably cannot be regarded as a single continuous coherent mass within the dosage form.

In other words, when the dosage form is particulate and the particles are contained in an outer matrix material, the dosage form according to the invention preferably comprises the particles as volume element(s) of a first type in which the pharmacologically active ingredient, the alkyl cellulose and the heteropolysaccharide are contained, and the outer matrix material as volume element of a second type differing from the material that forms the particles, preferably containing neither pharmacologically active ingredient, nor alkyl cellulose, nor heteropolysaccharide.

When the dosage form is particulate and the particles are contained in an outer matrix material, the relative weight ratio of particles to outer matrix material is not particularly limited. Preferably, said relative weight ratio is within the range of 1:1.00±0.75, more preferably 1:1.00±0.50, still more preferably 1:1.00±0.40, yet more preferably 1:1.00±0.30, most preferably 1:1.00±0.20, and in particular 1:1.00±0.10.

Preferably, the content of the outer matrix material is at least 2.5 wt.-%, at least 5 wt.-%, at least 10 wt.-%, at least 15 wt.-%, at least 20 wt.-%, at least 25 wt.-%, at least 30 wt.-%, at least 35 wt.-% or at least 40 wt.-%; more preferably at least 45 wt.-% or at least 50 wt.-%; still more preferably at least 55 wt.-% or at least 60 wt.-%; yet more preferably at least 65 wt.-% or at least 70 wt.-%; most preferably at least 75 wt.-% or at least 80 wt.-%; and in particular at least 85 wt.-% or at least 90 wt.-%; based on the total weight of the dosage form.

Preferably, the content of the outer matrix material is at most 90 wt.-% or at most 85 wt.-%; more preferably at most 80 wt.-% or at most 75 wt.-%; still more preferably at most 70 wt.-% or at most 65 wt.-%; yet more preferably at most 60 wt.-% or at most 55 wt.-%; most preferably at most 50 wt.-% or at most 45 wt.-%; and in particular at most 40 wt.-% or at most 35 wt.-%; based on the total weight of the dosage form.

Preferably, the outer matrix material is a mixture, preferably a homogeneous mixture of at least two different constituents, more preferably of at least three different constituents. In a preferred embodiment, all constituents of the outer matrix material are homogeneously distributed in the continuous phase that is formed by the outer matrix material.

Preferably, the outer matrix material is also provided in particulate form, i.e. in the course of the manufacture of the dosage forms according to the invention, the constituents of the outer matrix material are preferably processed into particles, subsequently mixed with the particles that contain the pharmacologically active ingredient, which is preferably an opioid, the alkyl cellulose and the heteropolysaccharide, and then compressed into the dosage forms.

Preferably, the average size of the particles of the outer matrix material is within the range of ±60%, more preferably ±50%, still more preferably ±40%, yet more preferably ±30%, most preferably ±20%, and in particular ±10% of the average size of the particles that contain the pharmacologically active ingredient, which is preferably an opioid, the alkyl cellulose and the heteropolysaccharide.

The particles of the outer matrix material can be manufactured by conventional methods for the preparation of aggregates and agglomerates from powder mixtures such as granulating and compacting.

In a preferred embodiment, the mixture of all constituents of the outer matrix material is blended and pre-compacted thereby yielding a pre-compacted outer matrix material.

The outer matrix material preferably does not contain any pharmacologically active ingredient.

Preferably, the outer matrix material comprises a filler or a binder. As many fillers can be regarded as binders and vice versa, for the purpose of specification "filler/binder" refers to any excipient that is suitable as filler, binder or both. Thus, the outer matrix material preferably comprises a filler/binder.

Preferred fillers (=filler/binders) are selected from the group consisting of silicium dioxide (e.g. Aerosil®), microcrystalline cellulose (e.g. Avicel®, Elcema®, Emocel®, ExCel®, Vitacell®); cellulose ether (e.g. Natrosol®, Klucel®, Methocel®, Blanose®, Pharmacoat®, Viscontran®); mannitol; dextrines; dextrose; calciumhydrogen phosphate (e.g. Emcompress®); maltodextrine (e.g. Emdex®); lactose (e.g. Fast-Flow Lactose®; Ludipress®, Pharmaceutical dosage Formtose®, Zeparox®); polyvinylpyrrolidone (PVP) (e.g. Kollidone®, Polyplasdone®, Polydone); saccharose (e.g. Nu-Tab®, Sugar Tab®); magnesium salts (e.g. MgCO$_3$, MgO, MgSiO$_3$); starches and pretreated starches (e.g. Prejel®, Primotab® ET, Starch® 1500). Preferred binders are selected from the group consisting of alginates; chitosanes; and any of the fillers mentioned above (=fillers/binders).

Some fillers/binders may also serve other purposes. It is known, for example, that silicium dioxide exhibits excellent function as a glidant. Thus, preferably, the outer matrix material comprises a glidant such as silicium dioxide.

In a preferred embodiment, the content of the filler/binder or mixture of fillers/binders in the outer matrix material is within the range of from 1 to 99 wt.-%, more preferably 25 to 90 wt.-%, based on the total weight of outer matrix material.

Preferably, the filler/binder is contained in the outer matrix material but not in the drug-containing particles of the dosage form according to the invention.

Preferably, the outer matrix material comprises a diluent or lubricant, preferably selected from the group consisting of calcium stearate; magnesium stearate; glycerol monobehenate (e.g. Compritol®); Myvatex®; Precirol®; Precirol® Ato5; sodium stearylfumarate (e.g. Pruv®); and talcum. Magnesium stearate is particularly preferred. Preferably, the content of the lubricant in the outer matrix material is at most 10.0 wt.-%, more preferably at most 7.5 wt.-%, still more preferably at most 5.0 wt.-%, yet more preferably at most 2.0 wt.-%, even more preferably at most 1.0 wt.-%, and most preferably at most 0.5 wt.-%, based on the total weight of the outer matrix material and based on the total weight of the dosage form.

In particularly preferred embodiment, the outer matrix material comprises a combination of filler/binder and lubricant.

The outer matrix material of the dosage forms according to the invention may additionally contain other excipients that are conventional in the art, e.g. diluents, binders, granulating aids, colorants, flavor additives, glidants, wet-regulating agents and disintegrants. The skilled person will readily be able to determine appropriate quantities of each of these excipients.

In the dosage form according to the invention, the pharmacologically active ingredient, preferably an opioid, is embedded in the matrix material, preferably dispersed in the matrix material.

For the purpose of specification, the term "matrix" preferably refers to the matrix material comprising the embedded pharmacologically active ingredient and the term "matrix material" refers to a preferably homogeneous, intimate mixture of the alkyl cellulose, the heteropolysaccharide and optionally present excipients.

In a preferred embodiment, the pharmacologically active ingredient, more preferably the opioid is embedded in a matrix material consisting of an alkyl cellulose, a heteropolysaccharide and optional excipients approved for oral use according to the Ph. Eur. and the USP, respectively.

Preferably, the matrix comprising the alkyl cellulose and the heteropolysaccharide provides resistance against dose dumping in aqueous ethanol.

Preferably, the dosage form provides prolonged release of the pharmacologically active ingredient. Particularly preferably, the matrix comprising the alkyl cellulose and the heteropolysaccharide provides prolonged release of the pharmacologically active ingredient embedded therein.

In a preferred embodiment, the matrix provides resistance against dose dumping in aqueous ethanol and/or the matrix provides prolonged release of the pharmacologically active ingredient, preferably the opioid.

When the dosage form according to the invention is particulate, e.g. in form of granules or pellets, the particles preferably comprise the matrix material and at least a portion of the total amount of the pharmacologically active ingredient that is contained in the pharmaceutical dosage form. Preferably, the particles comprise the total amount of the pharmacologically active ingredient that is contained in the dosage form. Preferably, the pharmacologically active ingredient, the alkyl cellulose and the heteropolysaccharide are intimately homogeneously distributed within the particles so that the particles do not contain any segments where either pharmacologically active ingredient is present in the absence of the alkyl cellulose and/or the heteropolysaccharide or the alkyl cellulose is present in the absence of the pharmacologically active ingredient and/or the heteropolysaccharide or the heteropolysaccharide is present in the absence of the pharmacologically active ingredient and/or the alkyl cellulose.

When the dosage form according to the invention can be regarded as a MUPS formulation which preferably comprises drug-containing particles and an outer matrix material, the outer matrix material is not a constituent of the matrix material and, thus, is to be distinguished from the matrix material of the dosage form according to the invention.

When the dosage form according to the invention is monolithic, the matrix material in which the pharmacologically active ingredient, preferably the opioid is embedded preferably forms the body of the dosage form. Preferably, the pharmacologically active ingredient, the alkyl cellulose and the heteropolysaccharide are intimately homogeneously distributed within the monolithic dosage form so that the monolithic dosage form does not contain any segments where either pharmacologically active ingredient is present in the absence of the alkyl cellulose and/or the heteropolysaccharide or the alkyl cellulose is present in the absence of the pharmacologically active ingredient and/or the heteropolysaccharide or the heteropolysaccharide is present in the absence of the pharmacologically active ingredient and/or the alkyl cellulose.

In a preferred embodiment, the relative weight ratio of the pharmacologically active ingredient, preferably the opioid to the matrix material is in the range of from 1:1 to 1:50, more preferably 1:1.5 to 1:45, still more preferably 1:2 to 1:40, even more preferably 1:2.5 to 1:35, yet more preferably 1:3 to 1:30, most preferably 1:3.5 to 1:25, and in particular 1:4 to 1:20.

Preferably, the total content of the matrix material is at least 35 wt.-%, more preferably at least 40 wt.-%, still more preferably at least 45 wt.-%, even more preferably at least 50 wt.-%, yet more preferably at least 55 wt.-%, most preferably at least 60 wt.-%, and in particular at least 65 wt.-%, relative to the total weight of the dosage form.

Preferably, the total content of the matrix material is at most 95 wt.-%, more preferably at most 90 wt.-%, still more preferably at most 85 wt.-%, most preferably at most 80 wt.-%, and in particular at most 75 wt.-%, relative to the total weight of the dosage form.

Preferably, the total content of the matrix material is within the range of from 35 to 95 wt.-%, more preferably 45 to 85 wt.-%, most preferably 55 to 80 wt.-%, and in particular 65 to 75 wt.-%, relative to the total weight of the dosage form.

Preferably, the total content of alkyl cellulose and heteropolysaccharide is at least 50 wt.-%, more preferably at least 60 wt.-%, still more preferably at least 70 wt.-%, even more preferably at least 80 wt.-%, yet more preferably at least 90 wt.-%, most preferably at least 95 wt.-%, and in particular at least 99.999 wt.-%, relative to the total weight of the matrix material.

Preferably, the total content of alkyl cellulose and heteropolysaccharide is at most 99.999 wt.-%, more preferably at most 99 wt.-%, still more preferably at most 97 wt.-%, most preferably at most 95 wt.-%, and in particular at most 93 wt.-%, relative to the total weight of the matrix material.

Preferably, the total content of alkyl cellulose and heteropolysaccharide is within the range of from 50 to 99.999 wt.-%, more preferably 60 to 99.999 wt.-%, still more preferably 70 to 99.999 wt.-%, most preferably 80 to 99.999 wt.-%, and in particular 90 to 99.999 wt.-%, relative to the total weight of the matrix material.

The total content of alkyl cellulose and heteropolysaccharide is at least 35 wt.-%, preferably at least 40 wt.-% or at least 45 wt.-% or at least 50 wt.-%, more preferably at least 55 wt.-%, still more preferably at least 65 wt.-%, even more preferably at least 70 wt.-%, yet more preferably at least 75 wt.-%, most preferably at least 80 wt.-%, and in particular at least 85 wt.-%, relative to the total weight of the dosage form.

Preferably, the total content of alkyl cellulose and heteropolysaccharide is at most 99 wt.-%, more preferably at most 97 wt.-%, still more preferably at most 95 wt.-%, even more preferably at most 93 wt.-%, most preferably at most 91 wt.-%, and in particular at most 90 wt.-%, relative to the total weight of the dosage form.

Preferably, the total content of alkyl cellulose and heteropolysaccharide is within the range of from 35 to 99 wt.-%, more preferably 45 to 97 wt.-%, still more preferably 55 to 95 wt.-%, even more preferably 65 to 93 wt.-%, most preferably 75 to 91 wt.-%, and in particular 85 to 90 wt.-%, relative to the total weight of the dosage form.

The relative weight ratio of heteropolysaccharide to alkyl cellulose is within the range of from 1:20 to 20:1, preferably 1:19 to 15 to:1, more preferably 1:18 to 10:1, still more preferably 1:18 to 7:1 or 1:14 to 7:1, even more preferably 1:18 to 4:1 or 1:12 to 4:1, yet more preferably 1:18 to 2:1 or 1:11 to 2:1, most preferably 1:18 to 1:1 or 1:10 to 1:1, and in particular 1:18 to 1:4 or 1:8 to 1:4.

In a preferred embodiment, the relative weight ratio of heteropolysaccharide to alkyl cellulose is within the range of from 1:18 to 2:1.

In another preferred embodiment, the content of the alkyl cellulose in the dosage form is higher than the content of the heteropolysaccharide in the dosage form.

The dosage form comprises a matrix material which in turn comprises an alkyl cellulose. In a preferred embodiment, the dosage form and the matrix material, respectively, contains only one alkyl cellulose. In another preferred embodiment, the dosage form and the matrix material, respectively, contains a mixture of two or more alkyl celluloses.

For the purpose of specification, the term "alkyl cellulose" (=cellulose ether) is supposed to relate to celluloses wherein some or all of the hydroxyl groups have been transformed to alkyl ether groups, wherein the alkyl moiety preferably is unsubstituted.

Preferred alkyl celluloses are selected from $C_{1-6}$-alkyl celluloses, more preferably unsubstituted $C_{1-6}$-alkyl celluloses, i.e. $C_{1-6}$-alkyl celluloses wherein the $C_{1-6}$-alkyl moiety is not substituted.

Preferably, the alkyl cellulose has a solution viscosity within the range of from 1 mPa·s to 150 mPa·s, more preferably 1 mPa·s to 7 mPa·s, or 5 mPa·s to 10 mPa·s, or 7 mPa·s to 13 mPa·s, or 15 mPa·s to 25 mPa·s, or 38 mPa·s to 52 mPa·s, or 60 mPa·s to 140 mPa·s, measured in a 5 wt.-% solution of 80 wt.-% toluene and 20 wt.-% ethanol at 25° C. in an Ubbelohde viscosimeter. In a particularly preferred embodiment, the alkyl cellulose has a solution viscosity within the range of from 70 mPa·s to 130 mPa·s, more preferably 80 mPa·s to 120 mPa·s and most preferably 90 mPa·s to 110 mPa·s, measured in a 5 wt.-% solution of 80 wt.-% toluene and 20 wt.-% ethanol at 25° C. in an Ubbelohde viscosimeter.

Preferably, the alkyl cellulose has an alkoxyl content of from 10 wt.-% to 80 wt.-%, more preferably 20 wt.-% to 70 wt.-%, still more preferably 22 wt.-% to 40 wt.-% or 40 wt.-% to 60 wt.-%, most preferably 24 wt.-% to 35 wt.-% or 44 wt.-% to 51 wt.-%, and in particular 26 wt.-% to 33 wt.-% or 48 wt.-% to 49.5 wt.-%.

In a preferred embodiment, the alkyl cellulose is selected from the group consisting of ethyl cellulose, hydroxyethyl cellulose, ethylmethyl cellulose, hydroxyethyl methyl cellulose, ethylhydroxy ethyl cellulose, methyl cellulose, carboxymethyl cellulose, hydroxypropyl cellulose, hydroxypropyl methyl cellulose, hydroxybutyl methyl cellulose, and carboxymethyl hydroxyethyl cellulose.

Preferred alkyl celluloses are ethyl cellulose, methyl cellulose and ethylmethyl cellulose. In a particularly preferred embodiment, the alkyl cellulose is ethyl cellulose.

Preferably, the alkyl cellulose is ethyl cellulose having an ethoxyl content of from 40 wt.-% to 60 wt.-%, more preferably 44 wt.-% to 51 wt.-%, most preferably 48 wt.-% to 49.5 wt.-%.

In a preferred embodiment, the alkyl cellulose is ethyl cellulose having a solution viscosity within the range of from 70 mPa·s to 130 mPa·s, more preferably 80 mPa·s to 120 mPa·s and most preferably 90 mPa·s to 110 mPa·s, measured in a 5 wt.-% solution of 80 wt.-% toluene and 20 wt.-% ethanol at 25° C. in an Ubbelohde viscosimeter.

Particularly preferably, the alkyl cellulose is ethyl cellulose, having
  an ethoxyl content of from 40 wt.-% to 60 wt.-%; and/or
  a solution viscosity within the range of from 70 mPa·s to 130 mPa·s, measured in a 5 wt.-% solution of 80 wt.-% toluene and 20 wt.-% ethanol at 25° C. in an Ubbelohde viscosimeter.

Preferred commercially available alkyl celluloses include ETHOCEL Polymers, in particular ETHOCEL Standard 100 Premium, ETHOCEL Standard 4 Premium, ETHOCEL Standard 7 Premium, ETHOCEL Standard 10 Premium, ETHOCEL Standard 20 Premium and ETHOCEL Standard 45 Premium.

The content of the alkyl cellulose in the matrix material is preferably at least 20 wt.-%, more preferably at least 30 wt.-%, still more preferably at least 40 wt.-%, even more preferably at least 50 wt.-%, yet more preferably at least 60 wt.-%, most preferably at least 70 wt.-%, and in particular at least 71 wt.-%, relative to the total weight of the matrix material.

The content of the alkyl cellulose in the matrix material is preferably at most 95 wt.-%, more preferably at most 94 wt.-%, still more preferably at most 93 wt.-%, even more preferably at most 92 wt.-%, most preferably at most 91 wt.-%, and in particular at most 90 wt.-%, relative to the total weight of the matrix material.

Preferably, the content of the alkyl cellulose in the matrix material is in the range of from 20 to 95 wt.-%, more preferably 30 to 94 wt.-%, still more preferably 40 to 93 wt.-%, even more preferably 50 to 92 wt.-%, most preferably 60 to 91 wt.-%, and in particular 70 to 90 wt.-% or 75 to 90 wt.-%, relative to the total weight of the matrix material.

In a preferred embodiment, the content of the alkyl cellulose is at least 10 wt.-%, more preferably at least 20 wt.-%, most preferably at least 30 wt.-%, and in particular at least 40 wt.-%, relative to the total weight of the dosage form. In another preferred embodiment, the content of the alkyl cellulose is at least 45 wt.-%, more preferably at least 50 wt.-%, still more preferably at least 55 wt.-%, most preferably at least 60 wt.-%, and in particular at least 63 wt.-%, relative to the total weight of the dosage form.

In a preferred embodiment, the content of the alkyl cellulose is at most 95 wt.-%, more preferably at most 93 wt.-%, still more preferably at most 91 wt.-%, even more preferably at most 89 wt.-%, most preferably at most 87 wt.-%, and in particular at most 86 wt.-%, relative to the total weight of the dosage form.

Preferably, the content of the alkyl cellulose is within the range of from 10 to 95 wt.-%, more preferably 25 to 93 wt.-%, still more preferably 35 to 91 wt.-%, even more preferably 45 to 89 wt.-%, most preferably 55 to 87 wt.-%, and in particular 63 to 86 wt.-%, relative to the total weight of the dosage form.

In a preferred embodiment, the alkyl cellulose is ethyl cellulose which content is within the range of from 63 to 86 wt.-%, relative to the total weight of the dosage form.

The amount of the alkyl cellulose which is contained in the dosage form is within the range of from 50 to 600 mg, more preferably 100 to 575 mg, still more preferably 150 to 550 mg, yet more preferably 200 to 525 mg, even more preferably 250 to 500 mg, most preferably 270 to 475 mg, and in particular 290 to 450 mg.

Preferably, the relative weight ratio of the pharmacologically active ingredient, preferably the opioid to the alkyl cellulose is in the range of from 1:30 to 10:1, more preferably 1:25 to 7:1, still more preferably 1:22 to 4:1, yet more preferably 1:20 to 1:1, most preferably 1:18 to 1:3, and in particular 1:17 to 1:5.

The dosage form according to the invention contains a matrix material comprising a heteropolysaccharide. In a preferred embodiment, the dosage form and the matrix material, respectively, contains only one heteropolysaccharide. In another preferred embodiment, the dosage form and the matrix material, respectively, contains a mixture of two or more heteropolysaccharides.

Heteropolysaccharides are polysaccharides which are based on two or more different monosaccharides.

The heteropolysaccharide may be acidic or neutral. For the purpose of specification, the term "acidic heteropolysaccharide" also includes any derivative of acidic heteropolysaccharides, such as e.g. salts, esters and amides.

In a preferred embodiment, the heteropolysaccharide is acidic and preferably selected from the group consisting of xanthan gum, agar, alginic acid, sodium alginate, propylene glycol alginate, gum arabic, λ-carrageenan, κ-carrageenan, τ-carrageenan, fucoidan, fucogalactan (GFS), gellan gum, gum ghatti, gum karaya, pectin, psyllium seed gum, gum tragacanth, welan gum, their corresponding salts and mixtures thereof.

In another preferred embodiment, the heteropolysaccharide is neutral and preferably selected from the group consisting of chitin, chitosan, curdlan, dextran, guar gum, inulin, ivory nut mannan, konjac glucomannan, laminaran, larch arabinogalactan, locust bean gum, pullulan, scleroglucan, tamarind gum, tara gum, their derivatives and mixtures thereof.

Preferably, the heteropolysaccharide is selected from the group consisting of xanthan gum, guar gum, alginic acid, sodium alginate, carrageenans, locust bean gum, and mixtures thereof.

In a preferred embodiment, the heteropolysaccharide is xanthan gum or guar gum. Particularly preferably, the heteropolysaccharide is xanthan gum.

Preferred commercially available heteropolysaccharides include Xanthan Gum Type 602.

Preferably, the dosage form contains a singly type of a heteropolysaccharide, preferably only xanthan gum, but no additional heteropolysaccharide. Preferably, the dosage form does not comprise a combination of xanthan gum and locust bean gum.

In a particularly preferred embodiment,
  the alkyl cellulose is ethyl cellulose; and/or
  the heteropolysaccharide is xanthan gum.

The content of the heteropolysaccharide in the matrix material is preferably at least 1 wt.-%, more preferably at least 3 wt.-%, still more preferably at least 5 wt.-%, even more preferably at least 7 wt.-%, yet more preferably at least 9 wt.-%, most preferably at least 10 wt.-%, and in particular at least 11 wt.-%, relative to the total weight of the matrix material. In another preferred embodiment, the content of the heteropolysaccharide in the matrix material is preferably at least 11 wt.-%, more preferably at least 13 wt.-%, still more preferably at least 15 wt.-%, even more preferably at least 17 wt.-%, yet more preferably at least 19 wt.-%, most preferably at least 21 wt.-%, and in particular at least 23 wt.-% or at least 25 wt.-%, relative to the total weight of the matrix material.

The content of the heteropolysaccharide in the matrix material is preferably at most 90 wt.-%, more preferably at most 80 wt.-%, still more preferably at most 70 wt.-%, even more preferably at most 60 wt.-%, yet more preferably at most 50 wt.-%, most preferably at most 40 wt.-%, and in particular at most 30 wt.-% or at most 29 wt.-%, relative to the total weight of the matrix material.

Preferably, the content of the heteropolysaccharide in the matrix material is in the range of from 1 to 90 wt.-%, more preferably 3 to 80 wt.-%, still more preferably 5 to 70 wt.-%, even more preferably 7 to 60 wt.-%, yet more preferably 8 to 50 wt.-%, most preferably 9 to 40 wt.-%, and in particular 10 to 30 wt.-% or 11 to 29 wt.-%, relative to the total weight of the matrix material.

In a preferred embodiment, the content of the heteropolysaccharide is below 80 wt.-%, more preferably below 70 wt.-%, still more preferably below 65 wt.-%, most preferably below 55 wt.-%, and in particular below 50 wt.-%, relative to the total weight of the pharmaceutical dosage form. In another preferred embodiment, the content of the heteropolysaccharide is below 45 wt.-%, more preferably below 40 wt.-%, still more preferably below 35 wt.-%, most preferably below 30 wt.-%, and in particular below 28 wt.-%, relative to the total weight of the dosage form.

In a preferred embodiment, the content of the heteropolysaccharide is above 1 wt.-%, more preferably above 3 wt.-%, still more preferably above 5 wt.-%, most preferably above 7 wt.-% or above 10 wt.-%, and in particular above 9 wt.-% or above 15 wt.-% or above 20 wt.-%, relative to the total weight of the dosage form.

Preferably, the content of the heteropolysaccharide is within the range of from 2 to 80 wt.-%, more preferably 3 to 70 wt.-%, still more preferably 4 to 60 wt.-%, yet more preferably 5 to 50 wt.-%, even more preferably 6 to 40 wt.-%, most preferably 7 to 30 wt.-%, and in particular 8 to 28 wt.-%, relative to the total weight of the dosage form.

In a preferred embodiment, the heteropolysaccharide is xanthan gum which content is within the range of from 8 to 28 wt.-%, relative to the total weight of the dosage form.

The amount of the heteropolysaccharide which is contained in the dosage form is within the range of from 5 to 300 mg, more preferably 15 to 250 mg, still more preferably 20 to 200 mg, yet more preferably 25 to 180 mg, even more preferably 30 to 160 mg, most preferably 35 to 140 mg, and in particular 40 to 130 mg.

Preferably, the relative weight ratio of the pharmacologically active ingredient, preferably the opioid to the heteropolysaccharide is in the range of from 1:10 to 10:1, more preferably 1:9 to 9:1, still more preferably 1:7 to 7:1, yet more preferably 1:5 to 5:1, most preferably 1:3 to 3:1, and in particular 1:2.5 to 2.5:1.

In a preferred embodiment, the dosage form contains only one pharmacologically active ingredient, preferably one opioid. In another preferred embodiment, the dosage form contains a combination of two or more pharmacologically active ingredients.

In a preferred embodiment, the pharmacologically active ingredient is soluble in water.

Preferably, the pharmacologically active ingredient is selected from ATC class [N], more preferably [N02] according to the WHO.

Particularly preferably, the pharmacologically active ingredient is an opioid. For the purpose of specification, the term "opioid" shall refer to any opioid as well as any physiologically acceptable salt thereof. Thus, preferably, the dosage form comprises an opioid or a physiologically acceptable salt thereof.

Opioids are active ingredients with potential for being abused and potential for dose dumping in ethanol.

According to the ATC index, opioids are divided into natural opium alkaloids, phenylpiperidine derivatives, diphenylpropylamine derivatives, benzomorphan derivatives, oripavine derivatives, morphinan derivatives and others. In a preferred embodiment, the pharmacologically active ingredient is selected from the group consisting of morphine, hydromorphone, nicomorphine, oxycodone, oxymorphone, dihydrocodeine, ketobemidone, pethidine, fenantyl, dextromoramide, piritramide, dextropropoxyphene, bezitramide, pentazocine, phenazocine, buprenorphine, butorphanol, nalbuphine, tilidine, tramadol, dezocine, meptazinol, tapentadol, and the physiologically acceptable salts thereof.

In another preferred embodiment, the pharmacologically active ingredient is selected from the group consisting of tramadol, tapentadol, faxeladol and axomadol.

In a particularly preferred embodiment, the pharmacologically active ingredient is selected from the group consisting of oxycodone, oxymorphone, hydrocodone, hydromorphone, tramadol, tapentadol, morphine, buprenorphine and the physiologically acceptable salts thereof.

In yet another preferred embodiment, the pharmacologically active ingredient is selected from the group consisting of 1,1-(3-dimethylamino-3-phenylpentamethylene)-6-fluoro-1,3,4,9-tetrahydropyrano[3,4-b]indole, particularly its hemicitrate; 1,1-[3-dimethylamino-3-(2-thienyl)pentamethylene]-1,3,4,9-tetrahydropyrano[3,4-b]indole, particularly its citrate; and 1,1-[3-dimethylamino-3-(2-thienyl)pentamethylene]-1,3,4,9-tetrahydropyrano[3,4-b]-6-fluoroindole, particularly its hemicitrate. These compounds are known from, e.g., WO 2004/043967, WO 2005/066183.

Preferably, the pharmacologically active ingredient is selected from the following compounds: alfentanil, allylprodine, alphaprodine, apocodeine, axomadol, bemidone, benzylmorphine, bezitramide, buprenorphine, butorphanol, carfentanil, clonitazene, cocaine, codeine, cyclorphan, cyprenorphine, desomorphine, dextromoramide, dextropropoxyphene, dezocine, diampromide, diamorphone, dihydrocodeine, dihydromorphine, dihydromorphone, dimenoxadol, dimephetamol, dimethylthiambutene, dioxaphetylbutyrate, dipipanone, eptazocine, ethoheptazine, ethylmethylthiambutene, ethylmorphine, etonitazene, etorphine, faxeladol, fentanyl, heroin, hydrocodone, hydromorphone, hydroxypethidine, isomethadone, hydroxymethylmorphinan, ketobemidone, levacetylmethadol (LAAM), levomethadone, levorphanol, levophenacylmorphane, lofentanil, meperidine, metapon, meptazinol, metazocine, methylmorphine, methadone, 3-methylfentanyl, 4-methylfentanyl, metopon, morphine, myrophine, nalbuphine, nalorphine, narceine, nicomorphine, norlevorphanol, normethadone, normorphine, norpipanone, opium, oxycodone, oxymorphone, Papaver somniferum, papaveretum, pentazocine, pethidine, phenadoxone, phenomorphane, phenazocine, pheno-peridine, piminodine, pholcodeine, piritramide, profadol, proheptazine, promedol, properidine, propoxyphene, remifentanil, sufentanil, tapentadol, tilidine (cis and trans), tramadol, N-(1-methyl-2-piperidinoethyl)-N-(2-pyridyl)propionamide, (1R,2R)-3-(3-dimethylamino-1-ethyl-2-methyl-propyl)phenol, (1R,2R,4S)-2-(dimethyl-amino)methyl-4-(p-fluorobenzyloxy)-1-(m-methoxyphenyl)cyclohexanol, (1R,2R)-3-(2-dimethylaminomethyl-cyclohexyl)phenol, (1S,2S)-3-(3-dimethylamino-1-ethyl-2-methyl-propyl)phenol, (2R,3R)-1-dimethylamino-3(3-methoxyphenyl)-2-methyl-pentan-3-ol, (1RS,3RS,6RS)-6-dimethylaminomethyl-1-(3-methoxyphenyl)-cyclohexane-1,3-diol, preferably as racemate, 3-(2-dimethylaminomethyl-1-hydroxy-cyclohexyl)phenyl 2-(4-isobutyl-phenyl)propionate, 3-(2-dimethylaminomethyl-1-hydroxy-cyclo-hexyl)phenyl 2-(6-methoxy-naphthalen-2-yl)propionate, 3-(2-dimethylaminomethyl-cyclohex-1-enyl)-phenyl 2-(4-isobutyl-phenyl)propionate, 3-(2-dimethylaminomethyl-cyclohex-1-enyl)-phenyl 2-(6-methoxy-naphthalen-2-yl)propionate, (RR-SS)-2-acetoxy-4-trifluoromethyl-benzoic acid 3-(2-dimethylaminomethyl-1-hydroxy-cyclohexyl)-phenyl ester, (RR-SS)-2-hydroxy-4-trifluoromethyl-benzoic acid 3-(2-dimethylaminomethyl-1-hydroxy-cyclohexyl)-phenyl ester, (RR-SS)-4-chloro-2-hydroxy-benzoic acid 3-(2-dimethylaminomethyl-1-hydroxy-cyclohexyl)-phenyl ester, (RR-SS)-2-hydroxy-4-methyl-benzoic acid 3-(2-dimethylaminomethyl-1-hydroxy-cyclohexyl)-phenyl ester, (RR-SS)-2-hydroxy-4-methoxy-benzoic acid 3-(2-dimethylaminomethyl-1-hydroxy-cyclohexyl)-phenyl ester, (RR-SS)-2-hydroxy-5-nitro-benzoic acid 3-(2-dimethylaminomethyl-1-hydroxy-cyclohexyl)-phenyl ester, (RR-SS)-2',4'-difluoro-3-hydroxy-biphenyl-4-carboxylic acid 3-(2-dimethylaminomethyl-1-hydroxy-cyclohexyl)-phenyl ester, and corresponding stereoisomeric compounds, in each case the corresponding derivatives thereof, physiologically acceptable enantiomers, stereoisomers, diastereomers and racemates and the physiologically acceptable derivatives thereof, e.g. ethers, esters or amides, and in each case the physiologically acceptable compounds thereof, in particular the acid or base addition salts thereof and solvates, e.g. hydrochlorides.

In another preferred embodiment, the pharmacologically active ingredient is selected from the group consisting of DPI-125, M6G (CE-04-410), ADL-5859, CR-665, NRP290 and sebacoyl dinalbuphine ester.

In another preferred embodiment, the pharmacologically active ingredient is selected from the group consisting of rabeprazole, fentanyl, risedronate, nifedipine, amphetamine salts, everolimus, alprazolam, lovastatin, zolpidem, dalfampridine, cyclobenzaprine, bupropion, mesalamine, tipranavir, donepezil, diclofenac, aspirin, sulfasalazine, morphine, dutasteride, clarithromycin, praziquantel, bisacodyl, ibandronate, verapamil, nicardipine, diltiazem, doxazosin, cefuroxime, mycophenolate, activated charcoal, ciprofloxacin, docusate, colestipol, methylphenidate, nicotine, carvedilol, pancrelipase, indinavir, duloxetine, cyclophosphamide, ganciclovir, divalproex, tolterodine, dexlansoprazole, doxylamine, pyridoxine, diltiazem, isosorbide, oxybutynin, ergocalciferol, hydroxyurea, isradipine, erythromycin, potassium bicarbonate, venlafaxine, morphine sulfate, darifenacin, budesonide, ergotamine, vismodegib, raloxifene, hydromorphone, deferasirox, piroxicam, fentanyl, ferrous sulfate, ferrous gluconate, metronidazole, tamsulosin, dexmethylphenidate, metformin, alendronate, imatinib, glipizide, gabapentin, propranolol, indomethacin, etravirine, zolpidem, guanfacine, paliperidone, isotretinoin, ruxolitinib, dutasteride, tamsulosin, sitagliptin, lopinavir, ritonavir, dexlansoprazole, clonidine, alogliptin, levetiracetam, telithromycin, desvenlafaxine, potassium salt, lamotrigine, fluvastatin, ambrisentan, hyoscyamine, lithium salt, brompheniramine, fluvoxamine, pyridostigmine, potassium chloride, pramipexole, amoxicillin, ibuprofen, guiafenesin, mycophenolate, mirabegron, memantine, naproxen, esomeprazole, nicotinic acid, nifedipine, nitroglycerin, orphenadrine, disopyramide, ritonavir, posaconazole, tapentadone, trazodone, doxycycline, oxycodone, pancrealipase, paroxetine, dabigatran, felodipide, lansoprazole, omeprazole, finasteride, ciprofloxicin, pantoprazole, fluoxetine, renolazine, sirolimus, prednisone, galantamine, sevelamer, sevelamer carbonate, ropinirole, lenalidomide, propafenone, tramadol, cinacalcet, quetiapine, levodopa, carbidopa, minocycline, chloral hydrate, dasatinib, atomoxetine, nisoldipine, hyoscyamine, nilotinib, diltiazem, dimethyl fumarate, carbamazepine, temozolomide, benzonatate, theophylline, topiramate, metoprolol, fesoterodine, bosentan, pentoxifylline, fenofibric, acetaminophen, budesonide, potassium citrate, alfuzosin, valganciclovir, didanosine, naproxen, esomeprazole, nevirapine, albuterol, pazopanib, rivaroxaban, omeprazole/NaHCO$_3$, hydrocodone, vorinostat, everolimus, zileuton, and corresponding stereoisomeric compounds, in each case the corresponding derivatives thereof, physiologically acceptable enantiomers, stereoisomers, diastereomers and racemates and the physiologically acceptable derivatives thereof, e.g. ethers, esters or amides, and in each case the physiologically acceptable compounds thereof, in particular the acid or base addition salts thereof and solvates, e.g. hydrochlorides.

The pharmacologically active ingredient, preferably the opioid may be present in form of a physiologically acceptable salt, e.g. physiologically acceptable acid addition salt.

Physiologically acceptable acid addition salts comprise the acid addition salt forms which can conveniently be obtained by treating the base form of the pharmacologically active ingredient, preferably the opioid with appropriate organic and inorganic acids. Pharmacologically active ingredients, preferably opioids containing an acidic proton may be converted into their non-toxic metal or amine addition salt forms by treatment with appropriate organic and inorganic bases. The term addition salt also comprises the hydrates and solvent addition forms which the active ingredients are able to form. Examples of such forms are e.g. hydrates, alcoholates and the like.

It has been surprisingly found that the content of the pharmacologically active ingredient, preferably the opioid in the dosage form and in the particles, respectively, can be optimized in order to provide the best compromise between tamper-resistance, disintegration time and drug release, drug load, processability (especially pharmaceutical dosage formability) and patient compliance.

The pharmacologically active ingredient, preferably the opioid is present in the dosage form in a therapeutically effective amount. The amount that constitutes a therapeutically effective amount varies according to the pharmacologically active ingredients being used, the condition being treated, the severity of said condition, the patient being treated, and the frequency of administration.

The content of the pharmacologically active ingredient in the dosage form is not limited. The dose of the pharmacologically active ingredient, preferably the opioid which is adapted for administration preferably is in the range of 0.1 mg to 500 mg, more preferably in the range of 1.0 mg to 400 mg, even more preferably in the range of 5.0 mg to 300 mg, and most preferably in the range of 10 mg to 250 mg. In a preferred embodiment, the total amount of the pharmacologically active ingredient, preferably the opioid that is contained in the dosage form is within the range of from 0.01 to 200 mg, more preferably 0.1 to 190 mg, still more preferably 1.0 to 180 mg, yet more preferably 1.5 to 160 mg, most preferably 2.0 to 100 mg and in particular 2.5 to 80 mg.

Preferably, the content of the pharmacologically active ingredient, preferably the opioid is within the range of from 0.01 to 80 wt.-%, more preferably 0.1 to 50 wt.-%, still more preferably 1 to 35 wt.-%, based on the total weight of the dosage form.

In a preferred embodiment, the content of the pharmacologically active ingredient, preferably the opioid is within the range of from 5.0±4.5 wt.-%, or 10±9.0 wt.-%, or 15±14 wt.-%, or 20±19 wt.-%, or 25±24 wt.-%; more preferably 5.0±4.0 wt.-%, or 10±8.0 wt.-%, or 15±12 wt.-%, or 20±19 wt.-%, or 25±24 wt.-%; still more preferably 5.0±3.5 wt.-%, or 10±7.0 wt.-%, or 15±10 wt.-%, or 20±17 wt.-%, or 25±21 wt.-%; yet more preferably 5.0±3.0 wt.-%, or 10±6.0 wt.-%, or 15±8.0 wt.-%, or 20±15 wt.-%, or 25±18 wt.-%; even more preferably 5.0±2.5 wt.-%, or 10±5.0 wt.-%, or 15±6.0 wt.-%, or 20±13 wt.-%, or 25±15 wt.-%; most preferably 5.0±2.0 wt.-%, or 10±4.0 wt.-%, or 15±4.0 wt.-%, or 20±11 wt.-%, or 25±12 wt.-%; and in particular 5.0±1.5 wt.-%, or 10±3.0 wt.-%, or 15±2.0 wt.-%, or 20±9 wt.-%, or 25±9 wt.-%; in each case either based on the total weight of the dosage form or, when the dosage form is particulate, based on the total weight of the particles that contain the pharmacologically active ingredient.

In another preferred embodiment, the content of the pharmacologically active ingredient, preferably the opioid is within the range of 5±4 wt.-%, more preferably 5±3 wt.-%, still more preferably 5±2 wt.-%, most preferably 5±1 wt.-%, and in particular 5±0.5 wt.-%, either based on the total weight of the dosage form or, when the dosage form is particulate, based on the total weight of the particles that contain the pharmacologically active ingredient. In still another preferred embodiment, the content of the pharmacologically active ingredient, preferably the opioid is within the range of 10±9 wt.-%, more preferably 10±7 wt.-%, still more preferably 10±5 wt.-%, yet more preferably 10±3 wt.-%, most preferably 10±1 wt.-%, and in particular 10±0.5 wt.-%, either based on the total weight of the dosage form or, when the dosage form is particulate, based on the total weight of the particles that contain the pharmacologically active ingredient. In yet another preferred embodiment, the content of the pharmacologically active ingredient, preferably the opioid is within the range of 15±14 wt.-%, more preferably 15±11 wt.-%, still more preferably 15±8 wt.-%, yet more preferably 15±5 wt.-%, most preferably 15±2 wt.-%, and in particular 15±0.5 wt.-%, either based on the total weight of the dosage form or, when the dosage form is particulate, based on the total weight of the particles that contain the pharmacologically active ingredient.

The skilled person may readily determine an appropriate amount of pharmacologically active ingredient, preferably opioid to include in a dosage form. For instance, in the case of analgesics, the total amount of pharmacologically active ingredient, preferably opioid present in the dosage form is that sufficient to provide analgesia. The total amount of pharmacologically active ingredient, preferably opioid administered to a patient in a dose will vary depending on numerous factors including the nature of the pharmacologically active ingredient, the weight of the patient, the severity of the pain, the nature of other therapeutic agents being administered etc.

In a preferred embodiment, the pharmacologically active ingredient, preferably the opioid is contained in the dosage form in an amount of 7.5±5 mg, 10±5 mg, 15±5 mg, 20±5 mg, 25±5 mg, 30±5 mg, 35±5 mg, 40±5 mg, 45±5 mg, 50±5 mg, 55±5 mg, 60±5 mg, 65±5 mg, 70±5 mg, 75±5 mg, 80±5 mg, 85±5 mg, 90±5 mg, 95±5 mg, 100±5 mg, 110±5 mg, 120±5 mg, 130±5, 140±5 mg, 150±5 mg, 160±5 mg, 170±5 mg, 180±5 mg, 190±5 mg, 200±5 mg, 210±5 mg, 220±5 mg, 230±5 mg, 240±5 mg, 250±5 mg, 260±5 mg, 270±5 mg, 280±5 mg, 290±5 mg, or 300±5 mg. In another preferred embodiment, the pharmacologically active ingredient, preferably the opioid is contained in the dosage form in an amount of 5±2.5 mg, 7.5±2.5 mg, 10±2.5 mg, 15±2.5 mg, 20±2.5 mg, 25±2.5 mg, 30±2.5 mg, 35±2.5 mg, 40±2.5 mg, 45±2.5 mg, 50±2.5 mg, 55±2.5 mg, 60±2.5 mg, 65±2.5 mg, 70±2.5 mg, 75±2.5 mg, 80±2.5 mg, 85±2.5 mg, 90±2.5 mg, 95±2.5 mg, 100±2.5 mg, 105±2.5 mg, 110±2.5 mg, 115±2.5 mg, 120±2.5 mg, 125±2.5 mg, 130±2.5 mg, 135±2.5 mg, 140±2.5 mg, 145±2.5 mg, 150±2.5 mg, 155±2.5 mg, 160±2.5 mg, 165±2.5 mg, 170±2.5 mg, 175±2.5 mg, 180±2.5 mg, 185±2.5 mg, 190±2.5 mg, 195±2.5 mg, 200±2.5 mg, 205±2.5 mg, 210±2.5 mg, 215±2.5 mg, 220±2.5 mg, 225±2.5 mg, 230±2.5 mg, 235±2.5 mg, 240±2.5 mg, 245±2.5 mg, 250±2.5 mg, 255±2.5 mg, 260±2.5 mg, or 265±2.5 mg.

In a particularly preferred embodiment, the pharmacologically active ingredient is tramadol, preferably its HCl salt, and the dosage form is adapted for administration twice daily. In this embodiment, the pharmacologically active ingredient is preferably contained in the dosage form in a total amount of from 5 to 300 mg. In another particularly preferred embodiment, the pharmacologically active ingredient is tramadol, preferably its HCl salt, and the dosage form is adapted for administration once daily. In this embodiment, the pharmacologically active ingredient is preferably contained in the dosage form in a total amount of from 10 to 500 mg.

In another particularly preferred embodiment, the pharmacologically active ingredient is oxycodone, preferably its HCl salt, and the dosage form is adapted for administration twice daily. In this embodiment, the pharmacologically active ingredient is preferably contained in the dosage form in a total amount of from 1 to 80 mg. In another particularly preferred embodiment, the pharmacologically active ingredient is oxycodone, preferably its HCl salt, and the dosage form is adapted for administration once daily. In this embodiment, the pharmacologically active ingredient is preferably contained in the dosage form in a total amount of from 2 to 320 mg.

In still another particularly preferred embodiment, the pharmacologically active ingredient is oxymorphone, preferably its HCl salt, and the dosage form is adapted for administration twice daily. In this embodiment, the pharmacologically active ingredient is preferably contained in the dosage form in a total amount of from 5 to 40 mg. In another particularly preferred embodiment, the pharmacologically active ingredient is oxymorphone, preferably its HCl salt, and the dosage form is adapted for administration once daily. In this embodiment, the pharmacologically active ingredient is preferably contained in the dosage form in a total amount of from 10 to 80 mg.

In yet another particularly preferred embodiment, the pharmacologically active ingredient is tapentadol, preferably its HCl salt, and the dosage form is adapted for administration once daily or twice daily. In this embodiment, pharmacologically active ingredient is preferably contained in the dosage form in a total amount of from 25 to 250 mg.

In a further particularly preferred embodiment, the pharmacologically active ingredient is hydromorphone, preferably its HCl salt, and the dosage form is adapted for administration twice daily. In this embodiment, the pharmacologically active ingredient is preferably contained in the dosage form in a total amount of from 2 to 52 mg. In another particularly preferred embodiment, the pharmacologically active ingredient is hydromorphone, preferably its HCl salt, and the dosage form is adapted for administration once daily. In this embodiment, the pharmacologically active ingredient is preferably contained in the dosage form in a total amount of from 4 to 104 mg.

In still a further particularly preferred embodiment, the pharmacologically active ingredient is hydrocodone, preferably its HCl salt, and the dosage form is adapted for administration twice daily. In this embodiment, the pharmacologically active ingredient is preferably contained in the dosage form in a total amount of from 5 to 250 mg. In another particularly preferred embodiment, the pharmacologically active ingredient is hydrocodone, preferably its HCl salt, and the dosage form is adapted for administration once daily. In this embodiment, the pharmacologically active ingredient is preferably contained in the dosage form in a total amount of from 5 to 250 mg.

In yet a further particularly preferred embodiment, the pharmacologically active ingredient is morphine, preferably its HCl or $H_2SO_4$ salt, and the dosage form is adapted for administration twice daily. In this embodiment, the pharmacologically active ingredient is preferably contained in the dosage form in a total amount of from 5 to 250 mg. In another particularly preferred embodiment, the pharmacologically active ingredient is morphine, preferably its HCl or $H_2SO_4$ salt, and the dosage form is adapted for administration once daily. In this embodiment, the pharmacologically active ingredient is preferably contained in the dosage form in a total amount of from 5 to 250 mg.

In another particularly preferred embodiment, the pharmacologically active ingredient is buprenorphine, preferably its HCl salt, and the dosage form is adapted for administration twice daily. In this embodiment, the pharmacologically active ingredient is preferably contained in the dosage form in a total amount of from 1 to 12 mg. In another particularly preferred embodiment, the pharmacologically active ingredient is buprenorphine, preferably its HCl salt, and the dosage form is adapted for administration once daily. In this embodiment, the pharmacologically active ingredient is preferably contained in the dosage form in a total amount of from 2 to 12 mg.

When the pharmaceutical dosage form is particulate, the particles present in the dosage form according to the invention preferably comprise 1 to 75 wt.-% of the pharmacologically active ingredient, preferably the opioid, more preferably 2 to 60 wt.-% of the pharmacologically active ingredient, preferably the opioid, still more preferably 3 to 40 wt.-% of the pharmacologically active ingredient, preferably the opioid, most preferably 4 to 25 wt.-% of the pharmacologically active ingredient, preferably the opioid and in particular 4.5 to 17 wt.-% of the pharmacologically active ingredient, preferably the opioid, based on the total weight of a particle.

When the dosage form is particulate, the content of the pharmacologically active ingredient, preferably the opioid is preferably at least 1 wt.-%, more preferably at least 2 wt.-%, still more preferably at least 3 wt.-%, most preferably at least 4 wt.-% and in particular at least 5 wt.-%, based on the total weight of a particle.

When the dosage form is particulate, the content of the pharmacologically active ingredient, preferably the opioid is preferably at most 70 wt.-%, more preferably at most 65 wt.-%, still more preferably at most 50 wt.-%, yet more preferably at most 35 wt.-%, most preferably at most 20 wt.-%, based on the total weight of a particle.

In a preferred embodiment, when the dosage form is particulate, the content of the pharmacologically active ingredient, preferably the opioid is within the range of 5±4 wt.-%, more preferably 5±3 wt.-%, still more preferably 5±2 wt.-%, most preferably 5±1 wt.-%, and in particular 5±0.5 wt.-%, based on the total weight of a particle. In another preferred embodiment, when the dosage form is particulate, the content of the pharmacologically active ingredient, preferably the opioid is within the range of 10±9 wt.-%, more preferably 10±7 wt.-%, still more preferably 10±5 wt.-%, yet more preferably 10±3 wt.-%, most preferably 10±1 wt.-%, and in particular 10±0.5 wt.-%, based on the total weight of a particle. In still another preferred embodiment, when the dosage form is particulate, the content of the pharmacologically active ingredient, preferably the opioid is within the range of 15±14 wt.-%, more preferably 15±11 wt.-%, still more preferably 15±8 wt.-%, yet more preferably 15±5 wt.-%, most preferably 15±2 wt.-%, and in particular 15±0.5 wt.-%, based on the total weight of a particle.

The pharmacologically active ingredient, preferably the opioid that is included in the preparation of the dosage forms according to the invention preferably has an average particle size of less than 500 microns, still more preferably less than 300 microns, yet more preferably less than 200 or 100 microns. There is no lower limit on the average particle size and it may be, for example, 50 microns. The particle size of the pharmacologically active ingredient may be determined by any technique conventional in the art, e.g. laser light scattering, sieve analysis, light microscopy or image analysis. When the dosage form is particulate, it is preferable that the largest dimension of the pharmacologically active ingredient particle be less than the size of the particles (e.g. less than the smallest dimension of the particles).

In a preferred embodiment, the dosage form contains a combination of a pharmacologically active ingredient, preferably an opioid and a further pharmacologically active ingredient which is not an opioid.

In another preferred embodiment, apart from the pharmacologically active ingredient, preferably the opioid, the dosage form does not contain any further pharmacologically active ingredient.

Said further pharmacologically active ingredient is preferably selected from ATC classes [M01A], [M01C], [N02B] and [N02C] according to the WHO.

Preferably, the further pharmacologically active ingredient is selected from the group consisting of acetylsalicylic acid, aloxiprin, choline salicylate, sodium salicylate, salicylamide, salsalate, ethenzamide, morpholine salicylate, dipyrocetyl, benorilate, diflunisal, potassium salicylate, guacetisal, carbasalate calcium, imidazole salicylate, phenazone, metamizole sodium, aminophenazone, propyphenazone, nifenazone, paracetamol, phenacetin, bucetin, propacetamol, rimazolium, glafenine, floctafenine, viminol, nefopam, flupirtine, ziconotide, methoxyflurane, nabiximols, dihydroergotamine, ergotamine, methysergide, lisuride, flumedroxone, sumatriptan, naratriptan, zolmitriptan, rizatriptan, almotriptan, eletriptan, frovatriptan, pizotifen, clonidine, iprazochrome, dimetotiazine, oxetorone, phenylbutazone, mofebutazone, oxyphenbutazone, clofezone, kebuzone, indomethacin, sulindac, tolmetin, zomepirac, diclofenac, alclofenac, bumadizone, etodolac, lonazolac, fentiazac, acemetacin, difenpiramide, oxametacin, proglumetacin, ketorolac, aceclofenac, bufexamac, piroxicam, tenoxicam, droxicam, lornoxicam, meloxicam, ibuprofen, naproxen, ketoprofen, fenoprofen, fenbufen, benoxaprofen, suprofen, pirprofen, flurbiprofen, indoprofen, tiaprofenic acid, oxaprozin, ibuproxam, dexibuprofen, flunoxaprofen, alminoprofen, dexketoprofen, naproxcinod, mefenamic acid, tolfenamic acid, flufenamic acid, meclofenamic acid, celecoxib, rofecoxib, valdecoxib, parecoxib, etoricoxib, lumiracoxib, nabumetone, niflumic acid, azapropazone, glucosamine, benzydamine, glucosaminoglycan polysulfate, proquazone, orgotein, nimesulide, feprazone, diacerein, morniflumate, tenidap, oxaceprol, chondroitin sulfate, oxycinchophen, sodium aurothiomalate, sodium aurotiosulfate, auranofin, aurothioglucose, aurotioprol, penicillamine, bucillamine, their physiologically acceptable salts, as well as mixtures thereof.

If the dosage form comprises a further pharmacologically active ingredient, said further pharmacologically active ingredient preferably is present in the dosage form in a therapeutically effective amount. The amount that constitutes a therapeutically effective amount varies according to the further pharmacologically active ingredient being used, the condition being treated, the severity of said condition, the patient being treated, and the frequency of administration.

The content of the further pharmacologically active ingredient in the dosage form is not limited. The dose of the further pharmacologically active ingredient which is adapted for administration preferably is in the range of 0.1 mg to 4 g.

The matrix material and the dosage form, respectively, may contain additional pharmaceutical excipients conventionally contained in pharmaceutical dosage forms in conventional amounts, such as antioxidants, preservatives, lubricants, plasticizer, fillers, binders, and the like.

Preferably, the matrix material and the dosage form, respectively, only comprises excipients which are approved for oral use according to the Ph. Eur. and the USP, respectively. Therefore, in a preferred embodiment, the dosage form according to the present invention does not contain any compound which is not approved for oral use. More preferably, the dosage form does not contain poly(ε-caprolactone).

The skilled person will readily be able to determine appropriate further excipients as well as the quantities of each of these excipients. Specific examples of pharmaceutically acceptable carriers and excipients are described in the Handbook of Pharmaceutical Excipients, American Pharmaceutical Association (1986).

In a preferred embodiment, the dosage form does not contain a disintegrant.

Preferably, the matrix material and the dosage form, respectively, further comprises an antioxidant. Suitable antioxidants include ascorbic acid, butylated hydroxyanisole (BHA), butylated hydroxytoluene (BHT), salts of ascorbic acid, monothioglycerol, phosphorous acid, vitamin C, vitamin E and the derivatives thereof, coniferyl benzoate, nordihydroguajaretic acid, gallus acid esters, sodium bisulfite, particularly preferably butylhydroxytoluene or butylhydroxyanisole and α-tocopherol. The antioxidant is preferably present in quantities of 0.01 wt.-% to 10 wt.-%, more preferably of 0.03 wt.-% to 5 wt.-%, most preferably of 0.05 wt.-% to 2.5 wt.-%, based on the total weight of the dosage form and the matrix material, respectively.

In a preferred embodiment, the matrix material and the dosage form, respectively, further comprise an acid, preferably citric acid. The amount of acid is preferably in the range of 0.01 wt.-% to about 20 wt.-%, more preferably in the range of 0.02 wt.-% to about 10 wt.-%, and still more preferably in the range of 0.05 wt.-% to about 5 wt.-%, and most preferably in the range of 0.1 wt.-% to about 1.0 wt.-%, based on the total weight of the dosage form and the matrix material, respectively.

In a preferred embodiment, the matrix material and the dosage form, respectively, contain at least one lubricant.

Especially preferred lubricants are selected from
- magnesium stearate and stearic acid;
- polyoxyethylene glycerol fatty acid esters, such as mixtures of mono-, di- and triesters of glycerol and di- and monoesters of macrogols having molecular weights within the range of from 200 to 4000 g/mol, e.g., macrogolglycerolcaprylocaprate, macrogolglycerollaurate, macrogolglycerolococoate, macrogolglycerollinoleate, macrogol-20-glycerolmonostearate, macrogol-6-glycerolcaprylocaprate, macrogolglycerololeate; macrogolglycerolstearate, macrogolglycerolhydroxystearate, and macrogolglycerolrizinoleate;
- polyglycolyzed glycerides, such as the one known and commercially available under the trade name "Labrasol";
- fatty alcohols that may be linear or branched, such as cetylalcohol, stearylalcohol, cetylstearyl alcohol, 2-octyldodecane-1-ol and 2-hexyldecane-1-ol; and
- polyethylene glycols having a molecular weight between 10.000 and 60.000 g/mol.

Preferably, the amount of the lubricant ranges from 0.01 wt.-% to about 10 wt.-%, more preferably in the range of 0.05 wt.-% to about 7.5 wt.-%, most preferably in the range of 0.1 wt.-% to about 5 wt.-%, and in particular in the range of 0.1 wt.-% to about 1 wt.-%, based on the total weight of the dosage form and the matrix material, respectively.

Preferably, the matrix material and the dosage form, respectively, further comprise a plasticizer. The plasticizer improves the matrix material. A preferred plasticizer is polyalkylene glycol, like polyethylene glycol, triacetin, fatty acids, fatty acid esters, waxes and/or microcrystalline waxes. Particularly preferred plasticizers are polyethylene glycols, such as PEG 6000.

Preferably, the content of the plasticizer is within the range of from 0.5 to 30 wt.-%, more preferably 1.0 to 25 wt.-%, still more preferably 2.5 wt.-% to 22.5 wt.-%, yet more preferably 5.0 wt.-% to 20 wt.-%, most preferably 6 to 20 wt.-% and in particular 7 wt.-% to 17.5 wt.-%, based on the total weight of the dosage form and the matrix material, respectively.

Plasticizers can sometimes act as a lubricant, and lubricants can sometimes act as a plasticizer.

In another preferred embodiment, the matrix material and the dosage form, respectively, contain no antioxidant and/or no acid and/or no lubricant and/or no plasticizer. More preferably, the matrix material and the dosage form, respectively, contain no excipients.

Preferred contents of the pharmacologically active ingredient, preferably the opioid, the alkyl cellulose, the heteropolysaccharide and excipients, relative to the total weight of the dosage form are summarized as embodiments $A^1$ to $A^{12}$ in the tables here below:

| wt.-% | $A^1$ | $A^2$ | $A^3$ | $A^4$ |
|---|---|---|---|---|
| pharmacologically active ingredient | 15 ± 14 | 15 ± 10 | 15 ± 7 | 15 ± 5 |
| alkyl cellulose | 85 ± 70 | 85 ± 50 | 85 ± 30 | 85 ± 10 |
| heteropolysaccharide | 10 ± 8 | 10 ± 6 | 10 ± 4 | 10 ± 3 |
| pharmaceutical excipients | 20 ± 20 | 20 ± 20 | 20 ± 20 | 20 ± 20 |

| wt.-% | $A^5$ | $A^6$ | $A^7$ | $A^8$ |
|---|---|---|---|---|
| pharmacologically active ingredient | 15 ± 14 | 15 ± 10 | 15 ± 7 | 15 ± 5 |
| alkyl cellulose | 75 ± 60 | 75 ± 40 | 75 ± 20 | 75 ± 10 |
| heteropolysaccharide | 15 ± 10 | 15 ± 8 | 15 ± 6 | 15 ± 5 |
| pharmaceutical excipients | 20 ± 20 | 20 ± 20 | 20 ± 20 | 20 ± 20 |

| wt.-% | $A^9$ | $A^{10}$ | $A^{11}$ | $A^{12}$ |
|---|---|---|---|---|
| pharmacologically active ingredient | 15 ± 14 | 15 ± 10 | 15 ± 7 | 15 ± 5 |
| alkyl cellulose | 65 ± 50 | 65 ± 35 | 65 ± 20 | 65 ± 10 |
| heteropolysaccharide | 25 ± 20 | 25 ± 15 | 25 ± 10 | 25 ± 5 |
| pharmaceutical excipients | 20 ± 20 | 20 ± 20 | 20 ± 20 | 20 ± 20 |

In a preferred embodiment, the dosage form, more preferably the matrix comprising the alkyl cellulose and the heteropolysaccharide provides prolonged release of the pharmacologically active ingredient, preferably the opioid. In another preferred embodiment, the dosage form, more preferably the matrix comprising the alkyl cellulose and the heteropolysaccharide provides immediate release of the pharmacologically active ingredient, preferably the opioid.

The term "prolonged release" is known to the skilled artisan. For the purpose of specification, the term "prolonged release" preferably refers to a release rate of the pharmacologically active ingredient from the formulation that has been reduced over time in order to maintain therapeutic activity, to reduce toxic effects, or for some other therapeutic purpose such as reducing the dosing frequency.

The term "immediate release" is known to the skilled artisan. For the purpose of specification, the term "immediate release" preferably refers to a release rate of the pharmacologically active ingredient from the formulation that is comparatively fast and not retarded.

In the dosage form according to the present invention, the release of the pharmacologically active ingredient is preferably not controlled by erosion of the surface of the dosage form. If the dosage form according to the present invention is particulate, the release of the pharmacologically active ingredient is preferably neither controlled by erosion of the surface of the particles, nor by erosion of the surface of the dosage form.

In a preferred embodiment, the dosage form provides prolonged release of the pharmacologically active ingredient, preferably the opioid. Preferably, the matrix provides for a prolonged release of the pharmacologically active ingredient, preferably the opioid from dosage form.

Preferably, under in vitro conditions the dosage form has released after 30 minutes 0.1 to 75%, after 240 minutes 0.5 to 99%, after 480 minutes 1.0 to 100% and after 720 minutes 2.5 to 100% of the pharmacologically active ingredient, preferably the opioid.

Suitable in vitro conditions are known to the skilled artisan. In this regard it can be referred to, e.g., the Eur. Ph. Preferably, the release profile is measured under the following conditions: Paddle apparatus, 50 rpm, 37±5° C., 900 mL 0.1 M HCl (pH 1.0) or simulated intestinal fluid pH 6.8 (phosphate buffer) or pH 4.5. In another preferred embodiment, the rotational speed of the paddle is increased to 75 rpm. In another preferred embodiment, the release profile is determined under the following conditions: basket method, 75 rpm, 37±5° C., 900 mL 0.1 N HCl or 900 mL of SIF sp (pH 6.8) or 900 mL of 0.1 N HCl+40 vol.-% ethanol.

Preferred release profiles $R^1$ to $R^7$ are summarized in the table here below [all data in wt.-% of released pharmacologically active ingredient]:

| time | $R^1$ | $R^1$ | $R^2$ | $R^3$ | $R^4$ | $R^5$ | $R^6$ | $R^7$ |
|---|---|---|---|---|---|---|---|---|
| 60 min | 0-60 | 0-10 | 2-20 | 4-20 | 5-30 | 15-40 | 15-50 | 20-65 |
| 120 min | 0-90 | 1-60 | 5-30 | 10-35 | 10-35 | 20-55 | 25-80 | 30-90 |
| 240 min | 1-99 | 5-95 | 15-45 | 25-85 | 15-45 | 40-80 | 35-100 | 50-95 |
| 480 min | 5-100 | 7-100 | 25-85 | 60-100 | 20-60 | 60-100 | 45-100 | 70-100 |
| 720 min | 10-100 | 10-100 | 35-100 | 80-100 | 30-80 | >80 | >80 | 70-100 |
| 960 min | 20-100 | 15-100 | 50-100 | >90 | 40-90 | >90 | >90 | >80 |
| 1440 min | 50-100 | 30-100 | 60-100 | >99 | >60 | >99 | >99 | >90 |
| 2160 min | >80 | >80 | >80 | | >80 | | | >99 |

In a particularly preferred embodiment; under in vitro conditions in 900 mL 0.1 N HCl (pH 1.0), using the paddle method according to Ph. Eur. at 50 rpm, after 1 h under physiological conditions, the dosage form has released at most 80%, more preferably at most 70%, most preferably at most 65% and in particular at most 60% of the pharmacologically active ingredient, preferably the opioid relative to the total amount of the pharmacologically active ingredient originally contained in the dosage form.

In another preferred embodiment, the dosage form provides immediate release of the pharmacologically active ingredient, preferably the opioid. Preferably, the matrix provides for an immediate release of the pharmacologically active ingredient, preferably the opioid from the dosage form.

Preferably, under in vitro conditions the dosage form has released after 15 minutes 20 to 90%, after 30 minutes 35 to 99%, after 45 minutes 50 to 99% and after 60 minutes more than 60% or more than 70% or more than 80% or more than 90% or more than 95% of the pharmacologically active ingredient, preferably the opioid.

Suitable in vitro conditions are known to the skilled artisan. In this regard it can be referred to, e.g., the Eur. Ph. Preferably, the release profile is measured under the following conditions: Paddle apparatus, 50 rpm, 37±5° C., 900 mL 0.1 M HCl (pH 1.0) or simulated intestinal fluid pH 6.8 (phosphate buffer) or pH 4.5. In another preferred embodiment, the rotational speed of the paddle is increased to 75 rpm. In another preferred embodiment, the release profile is determined under the following conditions: basket method, 75 rpm, 37±5° C., 900 mL 0.1 N HCl or 900 mL of SIF sp (pH 6.8) or 900 mL of 0.1 N HCl+40% ethanol.

In a preferred embodiment, the dosage form according to the invention has a breaking strength of less than 300 N, more preferably less than 200 N, or, when the dosage form is particulate, the particles have a breaking strength of less than 300 N, more preferably less than 200 N. According to this embodiment, the dosage form preferably is particulate and in form of a filled capsule.

In another preferred embodiment, the dosage form according to the invention has a breaking strength of at least 200 N, more preferably at least 300 N, or, when the dosage form is particulate, the particles have a breaking strength of at least 200 N, more preferably at least 300 N. According to this embodiment, the dosage form or, when it is particulate, the particles according to the invention which contain the pharmacologically active ingredient preferably have a breaking strength of at least 300 N, at least 400 N, or at least 500 N, preferably at least 600 N, more preferably at least 700 N, still more preferably at least 800 N, yet more preferably at least 1000 N, most preferably at least 1250 N and in particular at least 1500 N. Further according to this embodiment, preferably, the dosage form and the particles, respectively, cannot be pulverized by the application of force with conventional means, such as for example a pestle and mortar, a hammer, a mallet or other usual means for pulverization, in particular devices developed for this purpose (dosage form crushers). In this regard "pulverization" means crumbling into small particles. Avoidance of pulverization virtually rules out oral or parenteral, in particular intravenous or nasal abuse.

The "breaking strength" (resistance to crushing) of a dosage form and of a particle is known to the skilled person. In this regard it can be referred to, e.g., W. A. Ritschel, Die Tablette, 2. Auflage, Editio Cantor Verlag Aulendorf, 2002; H Liebermann et al., Pharmaceutical dosage forms: Pharmaceutical dosage forms, Vol. 2, Informa Healthcare; 2 edition, 1990; and Encyclopedia of Pharmaceutical Technology, Informa Healthcare; 1 edition.

For the purpose of specification, the breaking strength is preferably defined as the amount of force that is necessary in order to fracture a dosage form and a particle, respectively (=breaking force). Therefore, for the purpose of specification, a dosage form and a particle, respectively, does preferably not exhibit the desired breaking strength when it breaks, i.e., is fractured into at least two independent parts that are separated from one another. In another preferred embodiment, however, the dosage form and particle, respectively, is regarded as being broken if the force decreases by 25% (threshold value) of the highest force measured during the measurement (see below).

Methods for measuring the breaking strength are known to the skilled artisan. Suitable devices are commercially available.

For example, the breaking strength (resistance to crushing) can be measured in accordance with the Eur. Ph. 5.0, 2.9.8 or 6.0, 2.09.08 "Resistance to Crushing of Pharmaceutical dosage forms". The particles may be subjected to the same or similar breaking strength test as the dosage form. The test is intended to determine, under defined conditions, the resistance to crushing of dosage forms and individual particles, respectively, measured by the force needed to disrupt them by crushing. The apparatus consists of 2 jaws facing each other, one of which moves towards the other. The flat surfaces of the jaws are perpendicular to the direction of movement. The crushing surfaces of the jaws are flat and larger than the zone of contact with the dosage form and individual particle, respectively. The apparatus is calibrated using a system with a precision of 1 Newton. The dosage form and particle, respectively, is placed between the jaws, taking into account, where applicable, the shape, the break-mark and the inscription; for each measurement the dosage form and particle, respectively, is oriented in the same way with respect to the direction of application of the force (and the direction of extension in which the breaking strength is to be measured). The measurement is carried out on 10 dosage forms and particles, respectively, taking care that all fragments have been removed before each determination. The result is expressed as the mean, minimum and maximum values of the forces measured, all expressed in Newton.

A similar description of the breaking strength (breaking force) can be found in the USP. The breaking strength can alternatively be measured in accordance with the method described therein where it is stated that the breaking strength is the force required to cause a dosage form and particle, respectively, to fail (i.e., break) in a specific plane. The dosage forms and particles, respectively, are generally placed between two platens, one of which moves to apply sufficient force to the dosage form and particle, respectively, to cause fracture. For conventional, round (circular cross-section) dosage forms and particles, respectively, loading occurs across their diameter (sometimes referred to as diametral loading), and fracture occurs in the plane. The breaking force of dosage forms and particles, respectively, is commonly called hardness in the pharmaceutical literature; however, the use of this term is misleading. In material science, the term hardness refers to the resistance of a surface to penetration or indentation by a small probe. The term crushing strength is also frequently used to describe the resistance of dosage forms and particle, respectively, to the application of a compressive load. Although this term describes the true nature of the test more accurately than does hardness, it implies that dosage forms and particles, respectively, are actually crushed during the test, which is often not the case.

Alternatively, the breaking strength (resistance to crushing) can be measured in accordance with WO 2008/107149, which can be regarded as a modification of the method described in the Eur. Ph. The apparatus used for the measurement is preferably a "Zwick Z 2.5" materials tester, $F_{max}$=2.5 kN with a maximum draw of 1150 mm, which should be set up with one column and one spindle, a clearance behind of 100 mm and a test speed adjustable between 0.1 and 800 mm/min together with testControl software. Measurement is performed using a pressure piston with screw-in inserts and a cylinder (diameter 10 mm), a force transducer, $F_{max}$. 1 kN, diameter=8 mm, class 0.5 from 10 N, class 1 from 2 N to ISO 7500-1, with manufacturer's test certificate M according to DIN 55350-18 (Zwick gross force $F_{max}$=1.45 kN) (all apparatus from Zwick GmbH & Co. KG, Ulm, Germany) with Order No BTC-FR 2.5 TH. D09 for the tester, Order No BTC-LC 0050N. P01 for the force transducer, Order No BO 70000 S06 for the centring device.

In a preferred embodiment, the dosage form and particle, respectively, is regarded as being broken if it is fractured into at least two separate pieces.

The dosage form according to the invention provides tamper resistance in terms of resistance against dose-dumping in aqueous ethanol.

In a preferred embodiment, the dosage form, more preferably the matrix, further provides resistance against solvent extraction and/or resistance against grinding.

Preferably, the dosage form, more preferably the matrix, provides tamper resistance. Tamper resistance preferably means that the dosage form and the matrix, respectively,
(i) provides resistance against dose-dumping in aqueous ethanol; and
(ii) preferably provides resistance against solvent extraction; and/or (iii) preferably provides resistance against grinding.

Thus, the dosage form and the matrix, respectively, apart from exhibiting resistance (i), does not necessarily need to further exhibit resistances (ii) and (iii); but may preferably exhibit a combination thereof; namely a combination of only (i) and (ii); a combination of only (i) and (iii); or a combination of (i) and (ii) and (iii).

As used herein, the term "tamper-resistant" refers to dosage forms or segments that are resistant to conversion into a form suitable for misuse or abuse, particular for nasal and/or intravenous administration, by conventional means.

The dosage form according to the invention provides resistance against dose dumping in aqueous ethanol. Preferably, the matrix provides the dosage form with resistance against dose dumping in aqueous ethanol.

The dosage form can be tested in vitro using 0.1 N HCl with 40 vol.-% ethanol to evaluate alcohol extractability. Testing is preferably performed using standard procedures, e.g. USP Apparatus 1 (basket) or USP Apparatus 2 (paddle) at e.g. 50 rpm in e.g. 900 mL of media at 37° C., using a Perkin Elmer UV/VIS Spectrometer Lambda 20, UV at an appropriate wavelength for detection of the pharmacologically active ingredient present therein. Sample time points preferably include 0.5 and 1 hour.

Preferably, when comparing the in vitro release profile at 37° C. in 0.1 N HCl with the in vitro release profile in 0.1 N HCl/ethanol (40 vol.-%) at 37° C., the in vitro release 0.1 N HCl/ethanol (40 vol.-%) is preferably not substantially accelerated compared to the in vitro release in 0.1 N HCl. Preferably, in this regard "substantially" means that at any given time point the in vitro release in 0.1 N HCl/ethanol (40 vol.-%) relatively deviates from the in vitro release in 0.1 N HCl by not more than +15%, more preferably not more than +10%, still more preferably not more than +8%, yet more preferably not more than +6%, even more preferably not more than +4%, most preferably not more than +2% and in particular not more than +1% or not more than +0.5% or not more than +0.1%.

Preferably, with the dosage forms according to the invention, a substantial relative deceleration of the in vitro release in 0.1 N HCl/ethanol (40 vol.-%) compared to the in vitro release in 0.1 N HCl is observed. In a particularly preferred embodiment, at any given time point the in vitro release in 0.1 N HCl/ethanol (40 vol.-%) relatively deviates from the in vitro release in 0.1 N HCl by at least −0.01%, more preferably at least −0.05%, still more preferably at least −0.1%, most preferably at least −0.5% and in particular at least −1%.

Further, the dosage form can be tested in vitro using ethanol/simulated gastric fluid of 0%, 20% and 40% to evaluate alcohol extractability. Testing is preferably performed using standard procedures, e.g. USP Apparatus 1 (basket) or USP Apparatus 2 (paddle) at e.g. 50 rpm in e.g. 900 mL of media at 37° C., using a Perkin Elmer UV/VIS Spectrometer Lambda 20, UV at an appropriate wavelength for detection of the pharmacologically active ingredient present therein. Sample time points preferably include 0.5 and 1 hour.

Preferably, when comparing the in vitro release profile at 37° C. in simulated gastric fluid with the in vitro release profile in ethanol/simulated gastric fluid (40 vol.-%) at 37° C., the in vitro release in ethanol/simulated gastric fluid (40 vol.-%) is preferably not substantially accelerated compared to the in vitro release in simulated gastric fluid. Preferably, in this regard "substantially" means that at any given time point the in vitro release in ethanol/simulated gastric fluid (40 vol.-%) relatively deviates from the in vitro release in simulated gastric fluid by not more than +15%, more preferably not more than +10%, still more preferably not more than +8%, yet more preferably not more than +6%, even more preferably not more than +4%, most preferably not more than +2% and in particular not more than +1%.

Preferably, with the dosage forms according to the invention, a substantial relative deceleration of the in vitro release in ethanol/simulated gastric fluid (40 vol.-%) compared to the in vitro release in simulated gastric fluid is observed. In a particularly preferred embodiment, at any given time point the in vitro release in ethanol/simulated gastric fluid (40 vol.-%) relatively deviates from the in vitro release in simulated gastric fluid by at least −0.01%, more preferably at least −0.05%, still more preferably at least −0.1%, most preferably at least −0.5% and in particular at least −1%.

The dosage form according to the invention preferably exhibits resistance against solvent extraction. Preferably, the matrix provides the dosage form according to the invention with resistance against solvent extraction.

Preferably, when trying to tamper the pharmaceutical dosage form in order to prepare a formulation suitable for abuse by intravenous administration, the liquid part of the formulation that can be separated from the remainder by means of a syringe at room temperature is as little as possible, preferably it contains not more than 45 or 40 wt.-%, more preferably not more than 35 wt.-%, still more preferably not more than 30 wt.-%, yet more preferably not more than 25 wt.-%, even more preferably not more than 20 wt.-%, most preferably not more than 15 wt.-% and in particular not more than 10 wt.-% of the original content of the pharmacologically active ingredient, preferably the opioid.

Preferably, this property is tested by (i) dispensing a dosage form that is either intact or has been manually comminuted by means of two spoons in 5 ml of solvent, either purified water or aqueous ethanol (40 vol. %), (ii) allowing the dispersion to stand for 10 min at room temperature, (iii) drawing up the hot liquid into a syringe (needle 21G equipped with a cigarette filter), and (iv) determining the amount of the pharmacologically active ingredient contained in the liquid within the syringe.

In a preferred embodiment, the dosage form exhibits resistance against grinding. In another preferred embodiment, the dosage form does not exhibit resistance against grinding.

Preferably, the dosage form according to the invention is particulate, wherein the particles are obtained by wet granulation, dry granulation or fluid bed granulation.

A further aspect of the invention relates to a process for the production of an oral pharmaceutical dosage form as described herein comprising the steps of
(i) mixing a pharmacologically active ingredient, preferably an opioid; an alkyl cellulose; a heteropolysaccharide and optionally ethanol; and
(ii) granulating the mixture obtained in step (i).

Preferably, the process further comprises the steps of
(iii) screening the granules obtained in step (ii) through a sieve having a mesh size of preferably 1,000 μm; and
(iv) drying the screened granules obtained in step (iii); and
(v) filling the dried granules obtained in step (iv) in a capsule; and
(vi) optionally providing a film coating.

In another preferred embodiment, the granules preferably obtained in any of steps (ii) to (iv), preferably in combination with an outer matrix material, are compressed into tablets.

In still another preferred embodiment, the dosage form or, when it is particulate, the particles that contain the pharmacologically active ingredient are preferably thermoformed, preferably by melt-extrusion, although also other methods of thermoforming may be useful, such as press-molding at elevated temperature or heating of compacts that were manufactured by conventional compression in a first step and then heated above the softening temperature of the matrix material, in a second step to form break resistant, hardened compacts, i.e. monolithic dosage forms or particles, respectively. In this regard, thermoforming preferably means the forming or molding of a mass after, before or during the application of heat. Preferably, thermoforming is performed by hot-melt extrusion.

In a preferred embodiment, when the dosage form is particulate and the particles are hot-melt extruded, the dosage form is a filled capsule.

In a preferred embodiment, hot-melt extrusion is performed by means of a twin-screw-extruder. Melt extrusion preferably provides a melt-extruded strand that is preferably cut into monoliths, which are then optionally compressed and formed. Preferably, compression is achieved by means of a die and a punch, preferably from a monolithic mass obtained by melt extrusion. If obtained via melt extrusion, the compressing step is preferably carried out with a monolithic mass exhibiting ambient temperature, that is, a temperature in the range from 20 to 25° C.

When the dosage forms and particles, respectively, are manufactured by thermoforming, they may be produced by different processes. Several suitable processes have already been described in the prior art. In this regard it can be referred to, e.g., WO 2005/016313, WO 2005/016314, WO 2005/063214, WO 2005/102286, WO 2006/002883, WO 2006/002884, WO 2006/002886, WO 2006/082097, and WO 2006/082099.

In a preferred embodiment, when the dosage form is in form of a tablet, it is prepared by compression. Thus, when the dosage form is particulate, the particles as hereinbefore defined are preferably mixed, e.g. blended and/or granulated (e.g. wet granulated), with outer matrix material and the resulting mix (e.g. blend or granulate) is then compressed, preferably in molds, to form dosage forms. It is also envisaged that the particles herein described may be incorporated into a matrix using other processes, such as by melt granulation (e.g. using fatty alcohols and/or water-soluble waxes and/or water-insoluble waxes) or high shear granulation, followed by compression.

When the dosage forms according to the invention are manufactured by means of an eccentric press, the compression force is preferably within the range of from 5 to 15 kN. When the dosage forms according to the invention are manufactured by means of a rotating press, the compression force is preferably within the range of from 5 to 40 kN, in certain embodiments >25 kN, in other embodiments about 13 kN.

Another aspect of the invention relates to a dosage form which is obtainable by any of the processes described above.

Preferably, the release profile, the pharmacologically active ingredient, the alkyl cellulose, the heteropolysaccharide and optionally present pharmaceutical excipients are stable upon storage, preferably upon storage at elevated temperature, e.g. 40° C., for 3 months in sealed containers.

In connection with the release profile "stable" preferably means that when comparing the initial release profile with the release profile after storage, at any given time point the release profiles deviate from one another by not more than 20%, more preferably not more than 15%, still more preferably not more than 10%, yet more preferably not more than 7.5%, most preferably not more than 5.0% and in particular not more than 2.5%.

In connection with the pharmacologically active ingredient, the alkyl cellulose, the heteropolysaccharide, the optionally present further pharmacologically active ingredient and the optionally present pharmaceutical excipients "stable" preferably means that the dosage forms satisfy the requirements of EMEA concerning shelf-life of pharmaceutical products.

Preferably, after storage for 4 weeks, more preferably 6 months, at 40° C. and 75% rel. humidity, the content of the pharmacologically active ingredient, preferably the opioid in the dosage form according to the invention amounts to at least 98.0%, more preferably at least 98.5%, still more preferably at least 99.0%, yet more preferably at least 99.2%, most preferably at least 99.4% and in particular at least 99.6%, of its original content before storage.

In a preferred embodiment, the dosage form according to the invention contains no substances which irritate the nasal passages and/or pharynx, i.e. substances which, when administered via the nasal passages and/or pharynx, bring about a physical reaction which is either so unpleasant for the patient that he/she does not wish to or cannot continue administration, for example burning, or physiologically counteracts taking of the corresponding active compound, for example due to increased nasal secretion or sneezing. Further examples of substances which irritate the nasal passages and/or pharynx are those which cause burning, itching, urge to sneeze, increased formation of secretions or a combination of at least two of these stimuli. Corresponding substances and the quantities thereof which are conventionally to be used are known to the person skilled in the art. Some of the substances which irritate the nasal passages and/or pharynx are accordingly based on one or more constituents or one or more plant parts of a hot substance drug. Corresponding hot substance drugs are known per se to the person skilled in the art and are described, for example, in "Pharmazeutische Biologie—Drogen und ihre Inhaltsstoffe" by Prof. Dr. Hildebert Wagner, 2nd., revised edition, Gustav Fischer Verlag, Stuttgart-New York, 1982, pages 82 et seq. The corresponding description is hereby introduced as a reference and is deemed to be part of the disclosure.

The dosage form according to the invention furthermore preferably contains no antagonists for the pharmacologically active ingredient, preferably the opioid and the optionally present further pharmacologically active ingredient, preferably no antagonists against psychotropic substances, in particular no antagonists against opioids. Antagonists suitable for a given pharmacologically active ingredient are known to the person skilled in the art and may be present as such or in the form of corresponding derivatives, in particular esters or ethers, or in each case in the form of corresponding physiologically acceptable compounds, in particular in the form of the salts or solvates thereof. The dosage form according to the invention preferably contains no antagonists selected from among the group comprising naloxone, naltrexone, nalmefene, nalide, nalmexone, nalorphine or naluphine, in each case optionally in the form of a corresponding physiologically acceptable compound, in particular in the form of a base, a salt or solvate; and no neuroleptics, for example a compound selected from among the group comprising haloperidol, promethacine, fluphenazine, perphenazine, levomepromazine, thioridazine, perazine, chlorpromazine, chlorprothixine, zuclopenthixol, flupentixol, prothipendyl, zotepine, benperidol, pipamperone, melperone and bromperidol.

The dosage form according to the invention furthermore preferably contains no emetic. Emetics are known to the person skilled in the art and may be present as such or in the form of corresponding derivatives, in particular esters or ethers, or in each case in the form of corresponding physiologically acceptable compounds, in particular in the form of the salts or solvates thereof. The dosage form according to the invention preferably contains no emetic based on one or more constituents of ipecacuanha (ipecac) root, for example based on the constituent emetine, as are, for example, described in "Pharmazeutische Biologie—Drogen and ihre Inhaltsstoffe" by Prof. Dr. Hildebert Wagner, 2nd, revised edition, Gustav Fischer Verlag, Stuttgart, N.Y., 1982. The corresponding literature description is hereby introduced as a reference and is deemed to be part of the disclosure. The dosage form according to the invention preferably also contains no apomorphine as an emetic.

Finally, the dosage form according to the invention preferably also contains no bitter substance. Bitter substances and the quantities effective for use may be found in US 2003/0064099 A1, the corresponding disclosure of which should be deemed to be the disclosure of the present application and is hereby introduced as a reference. Examples of bitter substances are aromatic oils, such as peppermint oil, eucalyptus oil, bitter almond oil, menthol, fruit aroma substances, aroma substances from lemons, oranges, limes, grapefruit or mixtures thereof, and/or denatonium benzoate.

The dosage form according to the invention accordingly preferably contains neither substances which irritate the nasal passages and/or pharynx, nor antagonists for the pharmacologically active ingredient, nor emetics, nor bitter substances.

In a preferred embodiment, the dosage form according to the invention is adapted for administration once daily, preferably orally. In another preferred embodiment, the dosage form according to the invention is adapted for administration twice daily, preferably orally. In still another preferred embodiment, the dosage form according to the invention is adapted for administration thrice daily, preferably orally. In yet another preferred embodiment, the dosage form according to the invention is adapted for administration more frequently than thrice daily, for example 4 times daily, 5 times daily, 6 times daily, 7 times daily or 8 times daily, in each case preferably orally.

For the purpose of the specification, "twice daily" means equal or nearly equal time intervals, i.e., about every 12 hours, or different time intervals, e.g., 8 and 16 hours or 10 and 14 hours, between the individual administrations.

For the purpose of the specification, "thrice daily" means equal or nearly equal time intervals, i.e., about every 8 hours, or different time intervals, e.g., 6, 6 and 12 hours; or 7, 7 and 10 hours, between the individual administrations.

The dosage forms according to the invention may be used in medicine, e.g. as an analgesic. The dosage forms are therefore particularly suitable for the treatment or management of pain.

A further aspect of the invention relates to the dosage form as described above for use in the treatment of pain.

A further aspect of the invention relates to the use of a pharmacologically active ingredient, preferably an opioid for the manufacture of a dosage form as described above for treating pain.

A further aspect of the invention relates to a method of treating pain comprising the administration of the dosage form as described above to a subject in need thereof.

A further aspect according to the invention relates to the use of a dosage form as described above for avoiding or hindering the unintentional overdose of the pharmacologically active ingredient, preferably the opioid contained therein.

In this regard, the invention also relates to the use of a dosage form as described above for the prophylaxis and/or the treatment of a disorder, thereby preventing an overdose of the pharmacologically active ingredient, preferably the opioid, particularly due to dose dumping in aqueous ethanol.

In a particularly preferred embodiment, the dosage form is particulate and in form of a filled capsule, wherein
  the pharmacologically active ingredient is selected from the group consisting of oxycodone, oxymorphone, hydrocodone, hydromorphone, tramadol, tapentadol, morphine, buprenorphine and the physiologically acceptable salts thereof; and
  the alkyl cellulose is ethyl cellulose; and
  the heteropolysaccharide is xanthan gum; and
  the relative weight ratio of xanthan gum to ethyl cellulose is within the range of from 1:18 to 1:1.

In a particularly preferred embodiment
  the weight ratio of heteropolysaccharide to alkyl cellulose is within the range of from 1:18 to 1:1; and/or
  the total content of alkyl cellulose and heteropolysaccharide is at least 95 wt.-%, relative to the total weight of the matrix material, or the matrix material consists of the alkyl cellulose and the heteropolysaccharide; and/or
  the alkyl cellulose is selected from unsubstituted $C_{1-6}$-alkyl celluloses; and/or
  the alkyl cellulose is ethyl cellulose having an ethoxyl content of from 40 wt.-% to 60 wt.-%; and/or having a solution viscosity within the range of from 70 mPa·s to 130 mPa·s, measured in a 5 wt.-% solution of 80 wt.-% toluene and 20 wt.-% ethanol at 25° C. in an Ubbelohde viscosimeter; and/or
  the content of the alkyl cellulose in the matrix material is at most 90 wt.-%, relative to the total weight of the matrix material; and/or
  the content of the alkyl cellulose is within the range of from 45 to 89 wt.-%, relative to the total weight of the dosage form; and/or
  the heteropolysaccharide is selected from acidic heteropolysaccharides; and/or
  the heteropolysaccharide is xanthan gum; and/or
  the content of the heteropolysaccharide in the matrix material is at least 10 wt.-%, relative to the total weight of the matrix material; and/or
  the content of the heteropolysaccharide is within the range of from 8 to 27 wt.-%, relative to the total weight of the dosage form; and/or
  the dosage form contains only one pharmacologically active ingredient selected from the group consisting of oxycodone, oxymorphone, hydrocodone, hydromorphone, tramadol, tapentadol, morphine, buprenorphine and the physiologically acceptable salts thereof; and/or
  the pharmacologically active ingredient, preferably the opioid is present in the dosage form in a therapeutically effective amount; and/or
  apart from the pharmacologically active ingredient, preferably the opioid, the dosage form does not contain any further pharmacologically active ingredient; and/or
  the dosage form has a breaking strength of less than 200 N, or, when the dosage form is particulate, the particles have a breaking strength of less than 200 N; and/or
  at any given time point the in vitro release of the pharmacologically active ingredient, preferably the opioid from the dosage form in 0.1 N HCl/ethanol (40 vol.-%)

relatively deviates from the in vitro release in 0.1 N HCl by not more than +1%; or by at least −1%; and/or the dosage form provides prolonged release of the pharmacologically active ingredient, preferably the opioid; and/or the dosage form is particulate, wherein the particles have been manufactured by granulation; and/or the dosage form is a filled capsule; and/or the dosage form and, when the dosage form is particulate, the particles is/are not coated; and/or the dosage form does not contain any outer matrix material.

EXAMPLES

General Procedure:

Mixtures of the ingredients in powder form (Tramadol HCl, Ethylcellulose Ph. Eur. (Ethocel Standard 100 Premium), Xanthan Gum Type 602) were granulated with 70% (v/v) ethanol by using a mortar and pestle. The moist granulate was screened (mesh size 1,000 μm) and the thus obtained particles were dried in a drying cabinet for 17 to 18 hours. Thereafter, the particles were filled into capsules (DBcaps AA).

The xanthan gum was found to have a viscosity of 281 mPa·s, measured in a 1% aqueous solution at a shear rate of 50 s$^{-1}$ rotationally at 20° C. after 1 minute equilibration using a 6 cm acrylic cone (1°), wherein the shear was ramped up linearly from 1 to 50 s$^{-1}$ in 25 steps over 29 s.

The release profiles were determined in 0.1 N HCl with and without addition of 40% (v/v) ethanol in a USP Apparatus 2 (paddle) at 75 rpm in 600 mL of media at 37° C. with a LabSwiss sinker, using a HPLC method. The mobile phase consisted of 1460 mL potassium dihydrogenphosphate buffer pH 2.7 with 540 mL methanol with a flow rate of 2.5 mL/min. The stationary phase was a Supelcosil LC-8 DB 5 μm 150*4.6 mm chromatographic column conditioned at 35° C. Injected volume was 30 μL, detection was performed by UV absorption at a wavelength of 215 nm.

The obtained release data were normalized in that always the highest value measured after quickly stirring for a longer time was taken as 100% value ("infinity value").

Example 1

Capsules having the composition summarized in Table 1 below were prepared according to the general procedure:

TABLE 1

|  | m in mg (per capsule) | m in wt.-% |
|---|---|---|
| Tramadol HCl | 50.0 | 10.0 |
| Ethylcellulose Ph. Eur. (Ethocel Standard 100 Premium) | 400.0 | 80.0 |
| Xanthan Gum Type 602 | 50.0 | 10.0 |
| total | 500.0 | 100.0 |
| relative weight ratio of xanthan gum to ethyl cellulose |  | 1:8 |
| total content of ethyl cellulose and xanthan gum |  | 90.0 |

FIG. 1 shows the release profile of the capsules in 0.1 N HCl and in a mixture of 0.1 N HCl and 40% ethanol, respectively.

As can be seen from FIG. 1, the release of the active ingredient is prolonged and is not influenced by the addition of ethanol.

Example 2

Capsules having the composition summarized in Table 2 below were prepared according to the general procedure:

TABLE 2

|  | m in mg (per capsule) | m in wt.-% |
|---|---|---|
| Tramadol HCl | 25.0 | 5.0 |
| Ethylcellulose Ph. Eur. (Ethocel Standard 100 Premium) | 422.0 | 84.4 |
| Xanthan Gum Type 602 | 53.0 | 10.6 |
| total | 500.0 | 100.0 |
| relative weight ratio of xanthan gum to ethyl cellulose |  | 1:8 |
| total content of ethyl cellulose and xanthan gum |  | 95.0 |

Figure 2:
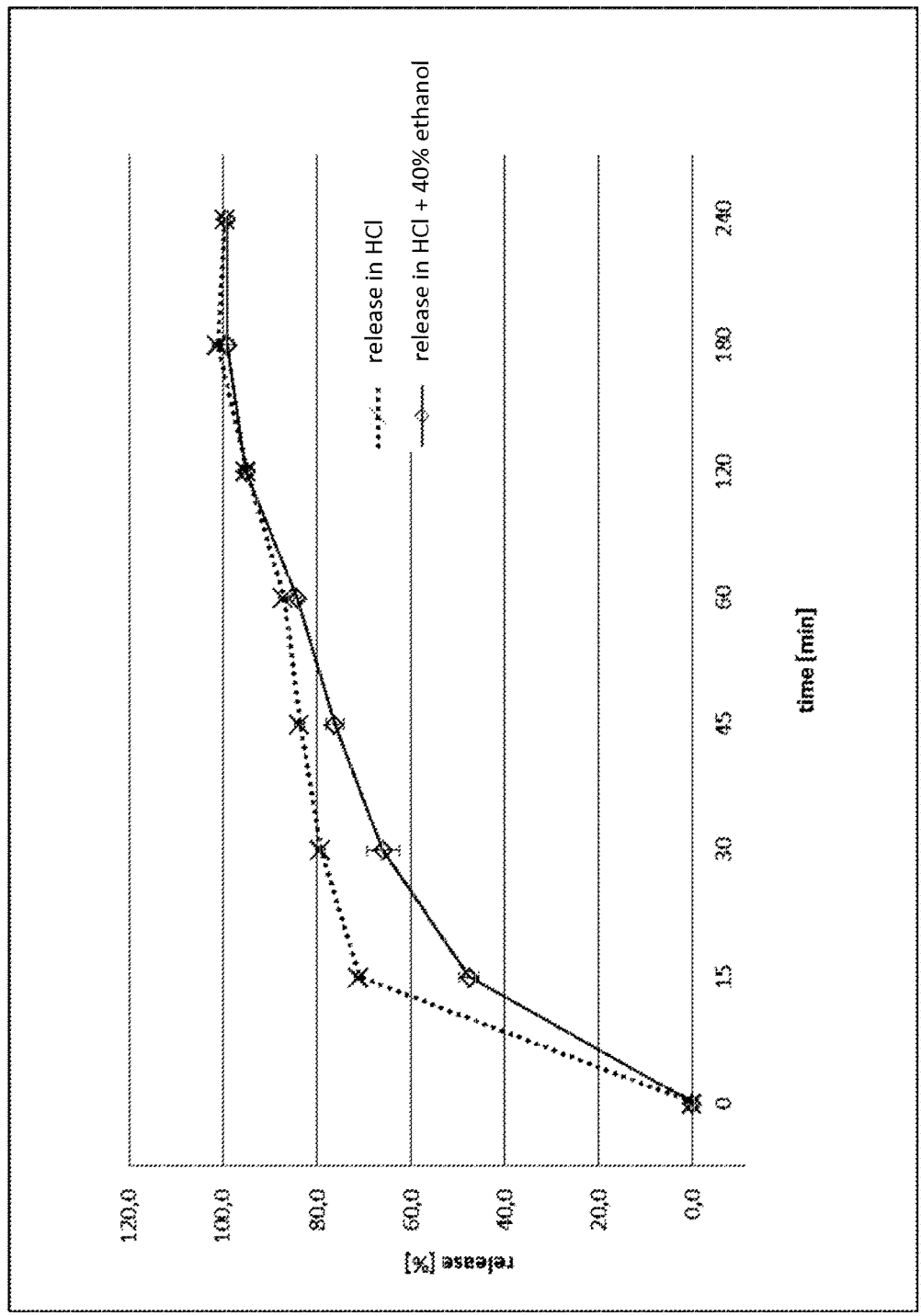
FIG. 2 shows the release profile of the capsules of Example 2 in 0.1 N HCl and in a mixture of 0.1 N HCl and 40% ethanol, respectively.

FIG. 2 shows the release profile of the capsules in 0.1 N HCl and in a mixture of 0.1 N HCl and 40% ethanol, respectively. The data are also summarized in Table 10.

As can be seen from FIG. 2, the release of the active ingredient is slightly prolonged and the addition of ethanol has a retarding influence on the release.

Example 3

Capsules having the composition summarized in Table 3 below were prepared according to the general procedure:

TABLE 3

|  | m in mg (per capsule) | m in wt.-% |
|---|---|---|
| Tramadol HCl | 75.0 | 15.0 |
| Ethylcellulose Ph. Eur. (Ethocel Standard 100 Premium) | 378.0 | 75.6 |
| Xanthan Gum Type 602 | 47.0 | 9.4 |
| total | 500.0 | 100.0 |
| relative weight ratio of xanthan gum to ethyl cellulose |  | 1:8 |
| total content of ethyl cellulose and xanthan gum |  | 85.0 |

Figure 3:
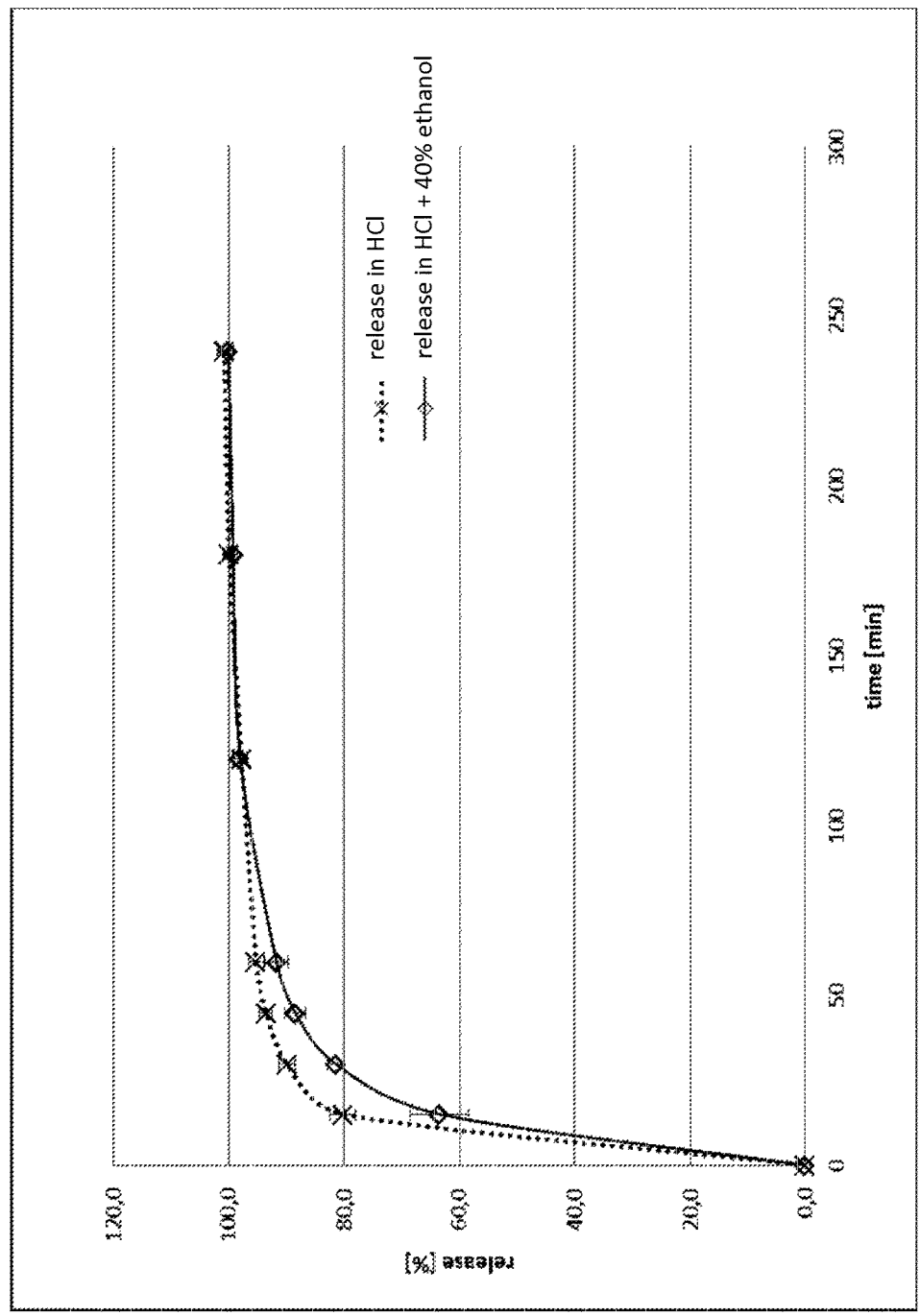
FIG. 3 shows the release profile of the capsules of Example 3 in 0.1 N HCl and in a mixture of 0.1 N HCl and 40% ethanol, respectively.

FIG. 3 shows the release profile of the capsules in 0.1 N HCl and in a mixture of 0.1 N HCl and 40% ethanol, respectively. The data are also summarized in Table 10.

As can be seen from FIG. 3, the release of the active ingredient is not prolonged. However, the addition of ethanol has a retarding influence on the release.

Example 4

Capsules having the composition summarized in Table 4 below were prepared according to the general procedure:

TABLE 4

|  | m in mg (per capsule) | m in wt.-% |
|---|---|---|
| Tramadol HCl | 50.0 | 10.0 |
| Ethylcellulose Ph. Eur. (Ethocel Standard 100 Premium) | 337.5 | 67.5 |
| Xanthan Gum Type 602 | 112.5 | 22.5 |
| total | 500.0 | 100.0 |
| relative weight ratio of xanthan gum to ethyl cellulose |  | 1:3 |
| total content of ethyl cellulose and xanthan gum |  | 90.0 |

Figure 4:
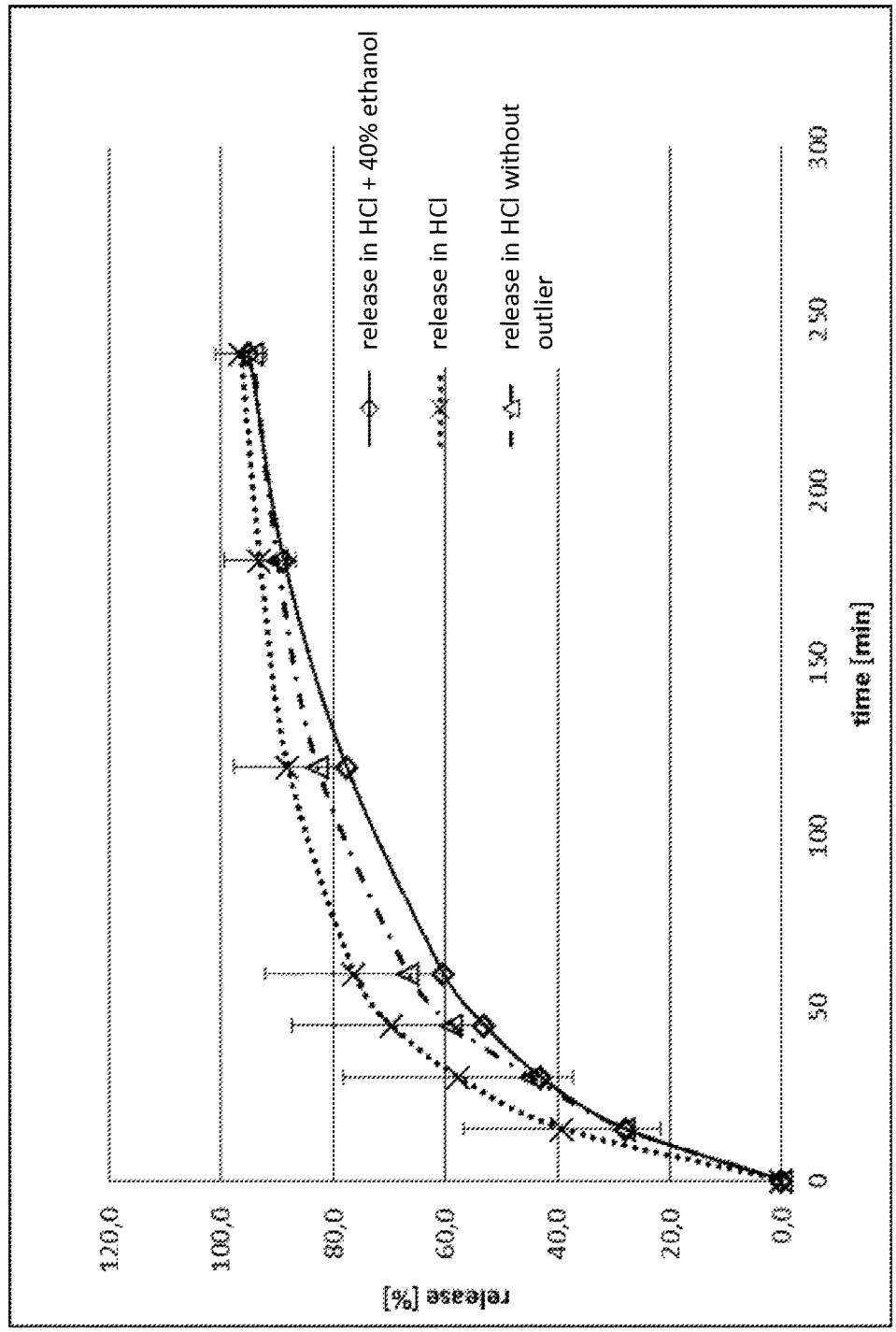
FIG. 4 shows the release profile of the capsules of Example 4 in 0.1 N HCl and in a mixture of 0.1 N HCl and 40% ethanol, respectively.

FIG. 4 shows the release profile of the capsules in 0.1 N HCl and in a mixture of 0.1 N HCl and 40% ethanol, respectively. The data are also summarized in Table 10.

As can be seen from FIG. 4, in both media the release of the active ingredient is distinctly prolonged and is further retarded by addition of ethanol.

Example 5

Capsules having the composition summarized in Table 5 below were prepared according to the general procedure:

TABLE 5

|  | m in mg (per capsule) | m in wt.-% |
|---|---|---|
| Tramadol HCl | 50.0 | 10.0 |
| Ethylcellulose Ph. Eur. (Ethocel Standard 100 Premium) | 382.5 | 76.5 |
| Xanthan Gum Type 602 | 67.5 | 13.5 |
| total | 500.0 | 100.0 |
| relative weight ratio of xanthan gum to ethyl cellulose |  | 1:5.7 |
| total content of ethyl cellulose and xanthan gum |  | 90.0 |

Figure 5:
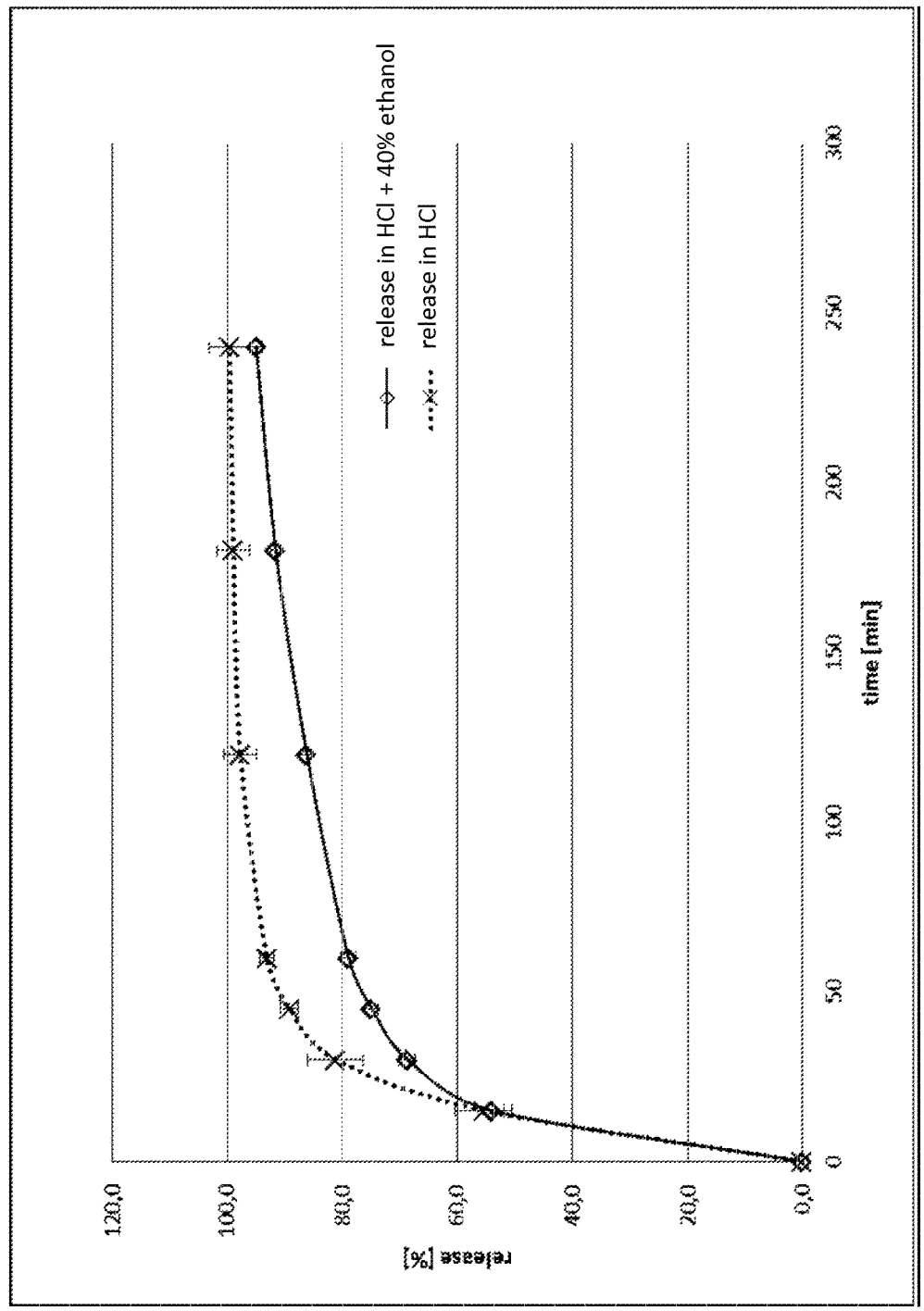
FIG. 5 shows the release profile of the capsules of Example 5 in 0.1 N HCl and in a mixture of 0.1 N HCl and 40% ethanol, respectively.

FIG. 5 shows the release profile of the capsules in 0.1 N HCl and in a mixture of 0.1 N HCl and 40% ethanol, respectively. The data are also summarized in Table 10.

As can be seen from FIG. 5, the release in 0.1 N HCl is not prolonged (i.e. immediate release). However, in the presence of ethanol, the release is distinctly prolonged.

Summing up, an extended release profile was not observed in all Examples 1 to 5. However, in all Examples the release was further retarded by the addition of ethanol. This result was completely unexpected because of the solubility of the matrix material ethylcellulose in ethanol.

An optimum extended release profile was observed in Example 4.

Example 6

Capsules having the composition summarized in Table 6 below were prepared according to the general procedure:

TABLE 6

|  | m in mg (per capsule) | m in wt.-% |
|---|---|---|
| Tramadol HCl | 45.0 | 10.0 |
| Ethylcellulose Ph. Eur. (Ethocel Standard 100 Premium) | 382.5 | 85.0 |
| Xanthan Gum Type 602 | 22.5 | 5.0 |
| total | 450.0 | 100.0 |
| relative weight ratio of xanthan gum to ethyl cellulose |  | 1:17 |
| total content of ethyl cellulose and xanthan gum |  | 90.0 |

The data obtained from dissolution tests in 0.1 N HCl and in a mixture of 0.1 N HCl and 40% ethanol, respectively, are summarized in Table 10.

Example 7

Capsules having the composition summarized in Table 7 below were prepared according to the general procedure:

TABLE 7

|  | m in mg (per capsule) | m in wt.-% |
|---|---|---|
| Tramadol HCl | 45.0 | 10.0 |
| Ethylcellulose Ph. Eur. (Ethocel Standard 100 Premium) | 292.5 | 65.0 |
| Xanthan Gum Type 602 | 112.5 | 25.0 |
| total | 450.0 | 100.0 |
| relative weight ratio of xanthan gum to ethyl cellulose |  | 1:2.6 |
| total content of ethyl cellulose and xanthan gum |  | 90.0 |

The data obtained from dissolution tests in 0.1 N HCl and in a mixture of 0.1 N HCl and 40% ethanol, respectively, are summarized in Table 10.

Example 8

Capsules having the composition summarized in Table 8 below were prepared according to the general procedure:

TABLE 8

|  | m in mg (per capsule) | m in wt.-% |
|---|---|---|
| Tramadol HCl | 45.0 | 10.0 |
| Ethylcellulose Ph. Eur. (Ethocel Standard 100 Premium) | 360.0 | 80.0 |
| Xanthan Gum Type 602 | 45.0 | 10.0 |
| total | 450.0 | 100.0 |
| relative weight ratio of xanthan gum to ethyl cellulose |  | 1:8 |
| total content of ethyl cellulose and xanthan gum |  | 90.0 |

The data obtained from dissolution tests in 0.1 N HCl and in a mixture of 0.1 N HCl and 40% ethanol, respectively, are summarized in Table 10.

Process Parameters

The process parameters are summarized in Table 9 below.

TABLE 9

| Process parameter granule: | Example 2 | Example 3 | Example 4 | Example 5 | Example 6 | Example 7 | Example 8 |
|---|---|---|---|---|---|---|---|
| Blending time [min] (granulated material) | 2 | 2 | 2 | 2 | 2 | 2 | 2 |
| Granulation time [min] (granulated material) | 6 | 5 | 6 | 6 | 16 | 16 | 12 |
| Amount of 70% ethanol [g] (granulated material) | 108.1 | 91.85 | 72.3 | 90.7 | 68.9 | 57.7 | 61.6 |
| Drying time/ Drying temperature (granulated material) | 17 h 50 min/50° C. | 17 h 50 min/50° C. | 17 h 50 min/50° C. | 17h 50 min/50° C. | 18 h 03 min/50° C. | 18 h 03 min/50° C. | 18 h 03 min/50° C. |
| Loss on drying [%] (granulated material) | −2.59 | −2.56 | −4.31 | −2.98 | −1.70 | −2.54 | −1.49 |
| Granule weight on capsule [mg] (granulate in capsule) | 453 | 456 | 454 | 457 | 457 | 456 | 458 |

Release Profiles

The data obtained from the dissolution tests in 0.1 N HCl and in a mixture of 0.1 N HCl and 40% ethanol, respectively, are summarized in Table 10 below.

TABLE 10

| In brackets: normalized values | Example 2 | Example 3 | Example 4 | Example 5 | Example 6 | Example 7 | Example 8 |
|---|---|---|---|---|---|---|---|
| Dissolution 0.1N HCl [%] (n = 3) | | | | | | | |
| after 15 min | 38 (71) | 68 (80) | 25 (28) | 46 (55) | 40 (49) | 55 (72) | 41 (58) |
| after 30 min | 43 (79) | 76 (89) | 39 (45) | 68 (81) | 52 (64) | 64 (84) | 50 (70) |
| after 45 min | 45 (84) | 79 (93) | 51 (59) | 75 (89) | 59 (73) | 68 (89) | 55 (77) |
| after 60 min | 47 (87) | 80 (94) | 58 (67) | 78 (93) | 63 (78) | 71 (93) | 58 (81) |
| after 120 min | 51 (95) | 83 (98) | 73 (83) | 82 (98) | 74 (90) | 74 (97) | 66 (92) |
| after 180 min | 54 (101) | 84 (99) | 79 (90) | 83 (99) | 78 (95) | 76 (100) | 69 (98) |
| after 240 min | 54 (100) | 85 (100) | 83 (95) | 83 (100) | 79 (97) | 75 (99) | 71 (99) |
| Infinity value (30 min 250 rpm) [%] | 54 (100) | 85 (100) | 88 (100) | 84 (100) | 82 (100) | 76 (100) | 71 (100) |
| Dissolution 0.1N HCl + 40% Ethanol [%] (n = 3) | | | | | | | |
| after 15 min | 47 (47) | 63 (64) | 24 (28) | 53 (54) | 53 (54) | 18 (24) | 34 (37) |
| after 30 min | 66 (66) | 81 (82) | 37 (43) | 68 (69) | 68 (69) | 29 (39) | 45 (49) |
| after 45 min | 76 (76) | 87 (89) | 46 (53) | 74 (75) | 74 (75) | 36 (48) | 52 (57) |
| after 60 min | 84 (84) | 91 (92) | 52 (60) | 78 (79) | 78 (79) | 42 (56) | 59 (65) |
| after 120 min | 95 (95) | 97 (98) | 67 (78) | 85 (86) | 85 (86) | 55 (74) | 71 (77) |
| after 180 min | 99 (98) | 98 (99) | 77 (90) | 90 (92) | 90 (92) | 70 (93) | 80 (88) |
| after 240 min | 99 (99) | 99 (100) | 82 (96) | 93 (95) | 93 (95) | 71 (95) | 83 (91) |
| Infinity value (30 min 250 rpm) [%] | 101 (100) | 99 (100) | 86 (100) | 98 (100) | 98 (100) | 75 (100) | 91 (100) |

The invention claimed is:

1. An oral pharmaceutical dosage form comprising a pharmacologically active ingredient embedded in a matrix material, wherein:

the pharmacologically active ingredient is one selected from pharmacologically active ingredients classified in Anatomical Therapeutic Chemical Classification System (ATC), class Nervous System;

the matrix material comprises a mixture of an alkyl cellulose and a heteropolysaccharide;

the alkyl cellulose is present in the dosage form in an amount of at least 50 wt.-% relative to the total weight of the dosage form;

the heteropolysaccharide is present in the dosage form in an amount of below 50 wt.-% relative to the total weight of the dosage form;

the total content of alkyl cellulose and heteropolysaccharide is at least 60 wt.-% relative to the total weight of the dosage form;

the pharmaceutical dosage form releases by 60 minutes more than 60% of the pharmacologically active ingredient when release of the pharmacologically active ingredient from the pharmaceutical dosage form is measured with a paddle apparatus at 50 rpm, at 37±5° C., in 900 mL 0.1 M HCl (pH 1.0) or simulated intestinal fluid at pH 6.8 (phosphate buffer) or pH 4.5; and the pharmaceutical dosage form provides resistance against dose dumping in aqueous ethanol.

2. The dosage form according to claim 1, wherein
the alkyl cellulose is ethyl cellulose; and/or
the heteropolysaccharide is xanthan gum.

3. The dosage form according to claim 1, which provides prolonged release of the pharmacologically active ingredient.

4. The dosage form according to claim 1, wherein the content of the heteropolysaccharide is below 45 wt.-%, relative to the total weight of the dosage form.

5. The dosage form according to claim 4, wherein the content of the heteropolysaccharide is below 30 wt.-%, relative to the total weight of the dosage form.

6. The dosage form according to claim 1, wherein the total content of alkyl cellulose and heteropolysaccharide is at least 70 wt.-%, relative to the total weight of the dosage form.

7. The dosage form according to claim 1, wherein the alkyl cellulose is ethyl cellulose having an ethoxyl content of from 40 wt.-% to 60 wt.-%.

8. The dosage form according to claim 1, wherein the alkyl cellulose is ethyl cellulose having a solution viscosity within the range of from 70 mPa·s to 130 mPa·s, measured in a 5 wt.-% solution of 80 wt.-% toluene and 20 wt.-% ethanol at 25° C. in an Ubbelohde viscosimeter.

9. The dosage form according to claim 1, wherein the pharmacologically active ingredient is an opioid.

10. The dosage form according to claim 9, wherein the pharmacologically active ingredient is selected from the group consisting of oxycodone, oxymorphone, hydrocodone, hydromorphone, tramadol, tapentadol, morphine, buprenorphine, and the physiologically acceptable salts thereof.

11. The dosage form according to claim 1, which is particulate.

12. The dosage form according to claim 1, which is a filled capsule or a tablet.

13. The dosage form according to claim 1, which is particulate and in form of a filled capsule, wherein
the pharmacologically active ingredient is selected from the group consisting of oxycodone, oxymorphone, hydrocodone, hydromorphone, tramadol, tapentadol, morphine, buprenorphine, and the physiologically acceptable salts thereof; and
the alkyl cellulose is ethyl cellulose; and
the heteropolysaccharide is xanthan gum; and
the relative weight ratio of xanthan gum to ethyl cellulose is within the range of from 1:18 to 1:1.

14. A method for treating pain in a patient in need thereof, said method comprising administering to said patient an effective amount therefor of a dosage form according to claim 1.

15. The dosage form according to claim 1, wherein the content of the alkyl cellulose is at least 63 wt.-%, relative to the total weight of the dosage form.

16. The dosage form according to claim 1, which releases by 3 hours at least 90% of the pharmacologically active ingredient.

* * * * *